US012016935B2

(12) United States Patent
Liu et al.

(10) Patent No.: US 12,016,935 B2
(45) Date of Patent: Jun. 25, 2024

(54) METHODS FOR DETECTING CCR2 RECEPTORS

(71) Applicants: Yongjian Liu, Chesterfield, MO (US); Robert Gropler, St. Louis, MO (US); Steven Brody, St. Louis, MO (US); Daniel Kreisel, St. Louis, MO (US)

(72) Inventors: Yongjian Liu, Chesterfield, MO (US); Robert Gropler, St. Louis, MO (US); Steven Brody, St. Louis, MO (US); Daniel Kreisel, St. Louis, MO (US)

(73) Assignee: Washington University, St. Louis, MO (US)

( * ) Notice: Subject to any disclaimer, the term of this patent is extended or adjusted under 35 U.S.C. 154(b) by 69 days.

(21) Appl. No.: 17/001,857

(22) Filed: Aug. 25, 2020

(65) Prior Publication Data

US 2020/0405889 A1 Dec. 31, 2020

Related U.S. Application Data

(62) Division of application No. 15/611,577, filed on Jun. 1, 2017, now abandoned.

(60) Provisional application No. 62/344,677, filed on Jun. 2, 2016.

(51) Int. Cl.
*A61K 51/08* (2006.01)
*A61K 51/02* (2006.01)
*A61K 51/12* (2006.01)

(52) U.S. Cl.
CPC .............. *A61K 51/08* (2013.01); *A61K 51/02* (2013.01); *A61K 51/088* (2013.01); *A61K 51/1244* (2013.01)

(58) Field of Classification Search
CPC ............ A61K 2121/00; A61K 2123/00; A61K 51/00; A61K 51/08; A61K 51/088; A61K 51/1244; A61K 51/02
USPC .......... 424/1.11, 1.49, 1.65, 1.69, 1.81, 1.85, 424/1.89, 9.1, 9.2, 9.3, 9.4, 9.5, 9.6; 534/7, 10–16; 514/1, 1.1, 21.4, 21.6, 514/21.7, 21.8, 21.9; 530/300
See application file for complete search history.

(56) References Cited

U.S. PATENT DOCUMENTS

| | | | |
|---|---|---|---|
| 7,566,539 B2 | 7/2009 | LaRosa | |
| 9,434,766 B2 | 9/2016 | Combadiere et al. | |
| 2013/0344070 A1 | 12/2013 | Huang | |
| 2015/0011477 A1* | 1/2015 | Combadiere | A61P 1/02 514/19.3 |
| 2015/0147276 A1* | 5/2015 | Ingber | A61P 7/00 424/9.5 |

FOREIGN PATENT DOCUMENTS

| | | | |
|---|---|---|---|
| WO | WO-2007/024715 | 4/2006 | |
| WO | WO-2013000922 A1 * | 1/2013 | ......... A61K 38/1793 |

OTHER PUBLICATIONS

Abdi et al. (2004)—Differential role of CCR2 in islet and heart allograft rejection: tissue specificity of chemokine/chemokine receptor function in vivo, J Immunol, 172, 2, pp. 767-775.
Alam et al. (1996)—Increased MCP-1, Rantes, and MIP-1alpha in bronchoalveolar lavage fluid of allergic asthmatic patients, American journal of respiratory and critical care medicine, 153, 4 Pt 1, pp. 1398-404.
Alanis et al. (2014)—Two nested developmental waves demarcate a compartment boundary in the mouse lung, Nature communications, 5, May, pp. 3923.
An et al. (2009)—Immunohistochemical detection of CCR2 and CX3CR1 in sepsis-induced lung injury, Forensic Science International, 192, 1-3, pp. 21-25.
Anderson et al. (2001)—64Cu-TETA-octreotide as a PET imaging agent for patients with neuroendocrine tumors, Journal of nuclear medicine : official publication, Society of Nuclear Medicine, 42, 2, pp. 213-221.
Anderson, Ferdani (2009)—Copper-64 radiopharmaceuticals for PET imaging of cancer: advances in preclinical and clinical research, Cancer biotherapy & radiopharmaceuticals, 24, 4, pp. 379-393.
Arispe, Diaz, Flora (2008)—Efficiency of histidine-associating compounds for blocking the Alzheimer's Abeta channel activity and cytotoxicity, Biophysical journal, 95, 10, pp. 4879-4889.
Audi et al. (2016)—99MTc-Hexamethylpropyleneamine Oxime Imaging for Early Detection of Acute Lung Injury in Rats Exposed to Hyperoxia or Lipopolysaccharide Treatment, Shock, 46, 4, pp. 420-430.
Auvynet et al. (2016)—ECL1i, d(LGTFLKC), a novel, small peptide that specifically inhibits CCL2-dependent migration, FASEB Journal, 30, 6, pp. 2370-2381.
Awad et al. (2011)—Monocyte / macrophage chemokine receptor CCR2 mediates diabetic renal injury, American journal of physiology. Renal physiology, 301, pp. 1358-1366.
Barrow et al. (2015)—Oscar Is a Receptor for Surfactant Protein D That Activates TNF-alpha Release from Human CCR2+ Inflammatory Monocytes, The Journal of Immunology, 194, 7, pp. 3317-3326.
Belperio et al. (2001)—Critical role for the chemokine MCP-1/CCR2 in the pathogenesis of bronchiolitis obliterans syndrome, Journal of Clinical Investigation, 108(4), pp. 547-556.
Bharat et al. (2008)—Immunological link between primary graft dysfunction and chronic lung allograft rejection, The Annals of Thoracic Surgery, 86(1), pp. 189-197.
Bhatia, Zemans, Jeyaseelan (2012)—Role of chemokines in the pathogenesis of acute lung injury, American Journal of Respiratory Cell and Molecular Biology, 46(5), pp. 566-572.
Boring et al. (1998)—Decreased lesion formation in CCR2-/-mice reveals a role for chemokines in the initiation of atherosclerosis., Nature, 394(6696), pp. 894-897.

(Continued)

*Primary Examiner* — D. L. Jones

(57) ABSTRACT

Among the various aspects of the present disclosure is the provision of compositions of imaging agents and methods for use in detecting, monitoring, and evaluating CCR2 associated diseases, disorders, and conditions.

24 Claims, 33 Drawing Sheets

Specification includes a Sequence Listing.

(56) References Cited

OTHER PUBLICATIONS

Boswell et al. (2004)—Comparative in Vivo Stability of Copper-64-Labeled Cross-Bridged and Conventional Tetraazamacrocyclic Complexes, Journal of Medicinal Chemistry, 47(6), pp. 1465-1474.
Boyko (1994)—Ruling Out or Ruling In Disease with the Most sensitive or Specific Diagnostic Test: Short Cut or Wrong Turn?, Medical Decision Making, 14(2), pp. 175-179.
Burnett et al. (2004)—Conditional macrophage ablation in transgenic mice expressing a Fas-based suicide gene, Journal of Leukocyte Biology, 75, 4, pp. 612-623.
Byers, Holtzman (2011)—Alternatively activated macrophages and airway disease, Chest, 140(3), pp. 768-774.
Byers et al. (2013)—Long-term IL-33-producing epithelial progenitor cells in chronic obstructive lung disease, The Journal of clinical investigation, 123(9), pp. 3967-3982.
Capelli et al. (1999)—Increased MCP-1 and MIP-1beta in bronchoalveolar lavage fluid of chronic bronchitis, The European respiratory journal : official journal of the European Society for Clinical Respiratory Physiology, 14(1), pp. 160-165.
Carmo et al. (2014)—Plasmin Induces In Vivo Monocyte Recruitment through Protease-Activated Receptor-1, MEK/ERK-, and CCR2-Mediated Signaling, Journal of Immunology, 193(7), pp. 3654-3663.
Carter (2013)—Progress in the discovery of CC chemokine receptor 2 antagonists, 2009-2012, Expert opinion on therapeutic patents, 23(5), pp. 549-568.
Charo, Peters (2003)—Chemokine Receptor 2 (CCR2) in Atherosclerosis, Infectious Diseases, and Regulation of T-Cell Polarization, Microcirculation, 10, pp. 259-264.
Charo, Ransohoff (2006)—The Many Roles of Chemokines and Chemokine Receptors in Inflammation, New England Journal of Medicine, 354(6), pp. 610-621.
Chen, Schuster (2006)—Imaging pulmonary inflammation with positron emission tomography: A biomarker for drug development, Molecular Pharmaceutics, 3(5), pp. 488-495.
Chen et al. (2006)—FDG-PET imaging of pulmonary inflammation in healthy volunteers after airway instillation of endotoxin, Journal of applied physiology (Bethesda, MD. : 1985), 100, pp. 1602-1609.
Chen, Lin, Gunn (2007)—Role of CCR2 + Monocyte-derived Cells in LPS- induced Acute Lung Injury ( B113 ), Journal of immunology, 178(1 Supplement), pp. LB24.
Chen et al. (2009)—[18F]fluorodeoxyglucose positron emission tomography for lung antiinflammatory response evaluation, American Journal of Respiratory and Critical Care Medicine, 180(6), pp. 533-539.
Chen, Chen (2010)—Design and development of molecular imaging probes, Current topics in medicinal chemistry, 10(12), pp. 1227-1236.
Chen et al. (2013)—Increased T cell glucose uptake reflects acute rejection in lung grafts, American Journal of Transplantation, 13(10), pp. 2540-2549.
Cherney et al. (2008)—Discovery of disubstituted cyclohexanes as a new class of CC chemokine receptor 2 antagonists, Journal of Medicinal Chemistry, 51(4), pp. 721-724.
Christensen et al. (2004)—Expression and functional implications of CCR2 expression on murine alveolar epithelial cells, Am. J. Physiol Lung Cell Mol. Physiol, 286(1), pp. L68-L72.
Churg, Sin, Wright (2011)—Everything prevents emphysema: Are animal models of cigarette smoke-induced chronic obstructive pulmonary disease any use?, American Journal of Respiratory Cell and Molecular Biology, 45(6), pp. 1111-1115.
Combadiere et al. (1995)—Monocyte chemoattractant protein-3 is a functional ligand for CC chemokine receptors 1 and 2B, Journal of Biological Chemistry, 270(50), pp. 29671-29675.
Daly et al. (2015)—Use of [18 F]FDG PET to Monitor The Development of Cardiac Allograft Rejection, Transplantation, 99(9), pp. e132-e139.

Daud et al. (2007)—Impact of immediate primary lung allograft dysfunction on bronchiolitis obliterans syndrome, American Journal of Respiratory and Critical Care Medicine, 175(5), pp. 507-513.
De Boer et al. (2000)—Monocyte chemoattractant protein I, interleukin 8, and chronic airways inflammation in COPD, American Journal of Pathology, 190, pp. 619-626.
De Prost, Tucci, Vidal Melo (2010)—Assessment of Lung Inflammation With 18F-FDG PET During Acute Lung Injury, AJR Am J Roentgenol, 195(2), pp. 292-300.
Decristoforo, Schwarz (2011)—Radiopharmacy: Regulations and legislations in relation to human applications, Drug Discovery Today: Technologies, 8(2-4), pp. e71-e77.
Dehdashti et al. (2012)—Assessment of progesterone receptors in breast carcinoma by PET with 21-18F-fluoro-16α, 17α-[(R)-(1'-α-furylmethylidene)dioxy]-19-norpregn-4-ene-3,20-dione., Journal of Nuclear Medicine, 53(3), pp. 363-370.
Dehdashti et al. (2013)—Assessment of cellular proliferation in tumors by PET using 18F-ISO-1., Journal of Nuclear Medicine, 54(3), pp. 350-357.
Deshane et al. (2015)—Subsets of airway myeloid-derived regulatory cells distinguish mild asthma from COPD, Journal of Allergy and Clinical Immunology, 135(2), pp. 413-424.
Dimitrijevic et al. (2007)—Absence of the chemokine receptor CCR2 protects against cerebral ischemia/reperfusion injury in mice, Stroke, 38(4), pp. 1345-1353.
Emad, Emad (2007)—Elevated levels of MCP-1, MIP-αand MIP-1β in the bronchoalveolar lavage (BAL) fluid of patients with mustard gas-induced pulmonary fibrosis, Toxicology, 240(1-2), pp. 60-69.
Eriksson et al. (2009)—Positron emission tomography in clinical islet transplantation, American Journal of Transplantation, 9(12), pp. 2816-2824.
Fani, Maecke, Okarvi (2012)—Radiolabeled peptides: Valuable tools for the detection and treatment of cancer, Theranostics, 2(5), pp. 481-501.
Gamble et al. (2009)—the Systemic and Pulmonary Lps Binding Protein Response to Intratracheal Lipopolysaccharide, Shock, 31(2), pp. 212-217.
Gavrilin et al. (2005)—Site-directed mutagenesis of CCR2 identified amino acid residues in transmembrane helices 1, 2, and 7 important for MCP-1 binding and biological functions, Biochemical and Biophysical Research Communications, 327(2), pp. 533-540.
Geissmann et al. (2010)—Development of monocytes, macrophages, and dendritic cells, Science (New York, NY), 327(5966), pp. 656-661.
Gelman et al. (2010)—CCR2 regulates monocyte recruitment as well as CD4+ T h1 allorecognition after lung transplantation, American Journal of Transplantation, 10(5), pp. 1189-1199.
Gonzalo et al. (1998)—The coordinated action of CC chemokines in the lung orchestrates allergic inflammation and airway hyperresponsiveness, The Journal of experimental medicine, 188(1), pp. 157-167.
Han et al. (2015)—Molecular imaging of folate receptor Beta-positive macrophages during acute lung inflammation, American Journal of Respiratory Cell and Molecular Biology, 53(1), pp. 50-59.
Hanefeld et al. (2012)—Orally-Administered Chemokine Receptor CCR2 Antagonist CCX140-B in Type 2 Diabetes: A Pilot Double-Blind, Randomized Clinical Trial, Diabetes and Metabolism, 3(225).
Hartl et al. (2005)—A role for MCP-1/CCR2 in interstitial lung disease in children, Respiratory research, 6, pp. 93.
Hatori et al. (2012)—PET Imaging of Lung Inflammation with [18F]FEDAC, a Radioligand for Translocator Protein (18 kDa), PLoS ONE, 7(9), e45065.
Hayashida et al. (1992)—Favorable biodistribution of 99mTc-ECD for brain SPECT comparing with 123I-IMP using alternative body scan, Annals of Nuclear Medicine, 6(4), pp. 229-233.
Herold et al. (2011)—Exudate macrophages attenuate lung injury by the release of IL-1 receptor antagonist in gram-negative pneumonia, American Journal of Respiratory and Critical Care Medicine, 183(10), pp. 1380-1390.
Herrero et al. (2012)—Feasibility and dosimetry studies for 18F-NOS as a potential PET radiopharmaceutical for inducible nitric oxide synthase in humans, Journal of nuclear, 53(6), pp. 994-1001.

(56) References Cited

OTHER PUBLICATIONS

Hildebrandt et al. (2004)—A critical role for CCR2 / MCP-1 interactions in the development of idiopathic pneumonia syndrome after allogeneic bone marrow transplantation, Blood, 103(6), pp. 2417-2427.
Hoffman et al. (2009)—Plasma Cytokines and Chemokines in Primary Graft Dysfunction Post-Lung Transplantation, American Journal of Transplantation, 9(2), pp. 389-396.
Huang et al. (2015)—Imaging pulmonary inducible nitric oxide synthase expression with PET, Journal of Nuclear Medicine, 56(1), pp. 76-81.
Izikson et al. (2000)—Resistance to experimental autoimmune encephalomyelitis in mice lacking the CC chemokine receptor (CCR)2, Journal of Experimental Medicine, 192(7), pp. 1075-1080.
Jacobson, Weiss (2013)—CXCR4 Chemokine Receptor Overview: Biology, Pathology and Applications in Imaging and Therapy, Theranostics, 3(1), pp. 1-2.
Jalbert et al. (2013)—Sequential staining improves detection of CCR2 and CX3CR1 on monocytes when simultaneously evaluating CCR5 by multicolor flow cytometry, Cytometry Part A, 83 A(3), pp. 280-286.
Jones et al. (2004)—Use of 18FDG-PET to Discriminate Between Infection and Rejection in Lung Transplant Recipients, Transplantation, 77(9), pp. 1462-1464.
Kaikita et al. (2004)—Targeted deletion of CC chemokine receptor 2 attenuates left ventricular remodeling after experimental myocardial infarction, The American journal of pathology, 165(2), pp. 439-447.
Kallinich et al. (2005)—Chemokine-receptor expression on T cells in lung compartments of challenged asthmatic patients, Clinical and Experimental Allergy, 35(1), pp. 26-33.
Kapoor, Thiemermann (2011)—Targeting CCR2: a novel therapeutic strategy for septic shock? American Journal of Respiratory and Critical Care Medicine, 183(2), pp. 150-151.
Kim et al. (2008)—Persistent activation of an innate immune response translates respiratory viral infection into chronic lung disease, Nature medicine, 14(6), pp. 633-640.
Kim et al. (2014)—IL-33-Induced Hematopoietic Stem and Progenitor Cell Mobilization Depends upon CCR2, Journal of immunology, 193(7), pp. 3792-3802.
Kledal et al. (1997)—A broad-spectrum chemokine antagonist encoded by Kaposi's sarcoma-associated herpesvirus, Science, 277(5332), pp. 1656-1659.
Kredel et al. (2011)—High-content analysis of CCR2 antagonists on human primary monocytes, Journal of biomolecular screening, 16(7), pp. 683-693.
Kreisel et al. (2010)—In vivo two-photon imaging reveals monocyte-dependent neutrophil extravasation during pulmonary inflammation, Proc Natl Acad Sci U S A, 107(42), pp. 18073-18078.
Kreisel et al. (2011)—Short- and long-term outcomes of 1000 adult lung transplant recipients at a single center, The Journal of thoracic and cardiovascular surgery, 141(1), pp. 215-222.
Kreisel et al. (2011)—Emergency granulopoiesis promotes neutrophil-dendritic cell encounters that prevent mouse lung allograft acceptance, Blood, 118(23), pp. 6172-6182.
Kruger et al. (2015)—Time course of cigarette smoke-induced changes of systemic inflammation and muscle structure, Am J Physiol Lung Cell Mol Physiol, 309, pp. L119-L128.
Laforest et al. (2005)—Dosimetry of 60/61/62/64Cu-ATSM: A hypoxia imaging agent for PET, European Journal of Nuclear Medicine and Molecular Imaging, 32(7), pp. 764-770.
Lambrecht, Hammad (2015)—The immunology of asthma, Nature Immunology, 16(1), pp. 45-56.
Landsman, Jung (2007)—Lung Macrophages Serve as Obligatory Intermediate between Blood Monocytes and Alveolar Macrophages, The Journal of Immunology, 179(6), pp. 3488-3494.
Lee et al. (2014)—Recruited alveolar macrophages, in response to airway epithelial-derived monocyte chemoattractant protein 1/CCL2, regulate airway inflammation and remodeling in allergic asthma, American Journal of Respiratory Cell and Molecular Biology, 52(6), pp. 772-784.
Leuschner et al. (2011)—Therapeutic siRNA silencing in inflammatory monocytes in mice, Nature Biotechnology, 29(11), pp. 1005-1010.
Lewis et al. (2000)—Comparative dosimetry of copper-64 and yttrium-90-labeled somatostatin analogs in a tumor-bearing rat model, Cancer biotherapy & radiopharmaceuticals, 15(6), pp. 593-604.
Li et al. (2008)—The chemokine receptors CCR2 and CX3CR1 mediate monocyte/macrophage trafficking in kidney ischemia-reperfusion injury, Kidney international, 74(12), pp. 1526-1537.
Liehn et al. (2010)—A new monocyte chemotactic protein-1/chemokine cc motif ligand-2 competitor limiting neointima formation and myocardial ischemia/reperfusion injury in mice, Journal of the American College of Cardiology, 56(22), pp. 1847-1857.
Lin et al. (2008)—CCR2+Monocyte-Derived Dendritic Cells and Exudate Macrophages Produce Influenza-Induced Pulmonary Immune Pathology and Mortality, The Journal of Immunology, 180(4), pp. 2562-2572.
Liu et al. (2009)—Impact of hydrogel nanoparticle size and functionalization on in vivo behavior for lung imaging and therapeutics, Molecular Pharmaceutics, 6(6), pp. 1891-1902.
Liu et al. (2010)—Molecular imaging of atherosclerotic plaque with (64)Cu-labeled natriuretic peptide and PET., Journal of nuclear medicine, 51(1), pp. 85-91.
Liu et al. (2011)—Targeting Angiogenesis Using a C-Type Atrial Natriuretic Factor-Conjugated Nanoprobe and PET, Journal of Nuclear Medicine, 52(12), pp. 1956-1963.
Liu, Welch (2012)—Nanoparticles labeled with positron emitting nuclides: Advantages, methods, and applications, Bioconjugate Chemistry, 23(4), pp. 671-682.
Liu et al. (2013)—PET Imaging of Chemokine Receptors in Vascular Injury-Accelerated Atherosclerosis, Journal of Nuclear Medicine, 54(7), pp. 1135-1141.
Liu et al. (2016)—Noninvasive Imaging of CCR2+ Cells in Ischemia-Reperfusion Injury After Lung Transplantation, American Journal of Transplantation, 16(10), pp. 3016-3023.
Liu et al. (2017)—PET-based imaging of chemokine receptor 2 in experimental and disease-related lung inflammation, Radiology, 283(3), pp. 758-768.
Lockhart et al. (2015)—Phase 1 Evaluation of [64Cu]DOTA-Patritumab to Assess Dosimetry, Apparent Receptor Occupancy, and Safety in Subjects with Advanced Solid Tumors, Molecular Imaging and Biology, 18(3), pp. 446-453.
Look et al. (2001)—Effects of paramyxoviral infection on airway epithelial cell foxj1 expression, ciliogenesis, and mucociliary function, American Journal of Pathology, 159(6), pp. 2055-2069.
Lu et al. (2007)—CCR2 expression correlates with prostate cancer progression, Journal of Cellular Biochemistry, 101(3), pp. 676-685.
Lu, Kang (2009)—Chemokine (C-C Motif) ligand 2 engages CCR2+ stromal cells of monocytic origin to promote breast cancer metastasis to lung and bone, Journal of Biological Chemistry, 284(42), pp. 29087-29096.
Luehmann et al. (2014)—PET/CT imaging of chemokine receptor CCR5 in vascular injury model using targeted nanoparticle., Journal of Nuclear Medicine, 55(4), pp. 629-634.
Luehmann et al. (2016)—PET/CT Imaging of Chemokine Receptors in Inflammatory Atherosclerosis Using Targeted Nanoparticles, Journal of Nuclear Medicine, 57(7), pp. 1124-1129.
Lundien et al. (2002)—Induction of MCP-1 expression in airway epithelial cells: Role of CCR2 receptor in airway epithelial injury, Journal of Clinical Immunology, 22(3), pp. 144-152.
Lüttichau et al. (2000)—A highly selective CC chemokine receptor (CCR)8 antagonist encoded by the poxvirus molluscum contagiosum, The Journal of experimental medicine, 191(1), pp. 171-180.
Majmudar et al. (2013)—Monocyte-directed RNAi targeting CCR2 improves infarct healing in atherosclerosis-prone mice, Circulation, 127(20), pp. 2038-2046.
Martinu et al. (2014)—Role of C-C motif ligand 2 and C-C motif receptor 2 in murine pulmonary graft-versus-host disease after

(56) References Cited

OTHER PUBLICATIONS lipopolysaccharide inhalations, American Journal of Respiratory Cell and Molecular Biology, 51(6), pp. 810-821.

Matute-Bello, Frevert, Martin (2008)—Animal models of acute lung injury, Am J Physiol Lung Cell Mol Physiol, 295, pp. 379-399.

Maus et al. (2002)—The role of CC chemokine receptor 2 in alveolar monocyte and neutrophil immigration in intact mice, American Journal of Respiratory and Critical Care Medicine, 166(3), pp. 268-273.

Maus et al. (2003)—Monocytes Are Potent Facilitators of Alveolar Neutrophil Emigration During Lung Inflammation: Role of the CCL2-CCR2 Axis, The Journal of Immunology, 170(6), pp. 3273-3278.

Maus et al. (2005)—CCR2-positive monocytes recruited to inflamed lungs downregulate local CCL2 chemokine levels, American journal of physiology. Lung cellular and molecular physiology, 288(2), pp. L350-L358.

McAleer, Kolls (2014)—Directing traffic: IL-17 and IL-22 coordinate pulmonary immune defense, Immunological Reviews, 260(1), pp. 129-144.

Meloni et al. (2003)—Monocyte chemoattractant protein-1 levels in bronchoalveolar lavage fluid of lung-transplanted patients treated with tacrolimus as rescue treatment for refractory acute rejection, Transplantation Proceedings, 35(4), pp. 1523-1526.

Mirzadegan et al. (2000)—Identification of the binding site for a novel class of CCR2b chemokine receptor antagonists. Binding to a common chemokine receptor motif within the helical bundle, Journal of Biological Chemistry, 275(33), pp. 25562-25571.

Moore et al. (2005)—CCR2-mediated recruitment of fibrocytes to the alveolar space after fibrotic injury, Am J Pathol, 166(3), pp. 675-684.

Murray, Wynn (2011)—Protective and pathogenic functions of macrophage subsets, Nature Reviews Immunology, 11(11), pp. 723-737.

Nava et al. (2010)—Two-photon microscopy in pulmonary research, Seminars in Immunopathology, 32(3), pp. 297-304.

Norenberg, Schwarz, Vanbrocklin (2011)—FDA cGMP Requirements for PET Drugs, Journal of Nuclear Medicine, 52(5), pp. 16N.

Okazaki et al. (2007)—A mouse model of orthotopic vascularized aerated lung transplantation, American Journal of Transplantation, 7(6), pp. 1672-1679.

Okuma et al. (2004)—C—C chemokine receptor 2 (CCR2) deficiency improves bleomycin-induced pulmonary fibrosis by attenuation of both macrophage infiltration and production of macrophage-derived matrix metalloproteinases, Journal of Pathology, 204(5), pp. 594-604.

Osterholzer et al. (2008)—CCR2 mediates conventional dendritic cell recruitment and the formation of bronchovascular mononuclear cell infiltrates in the lungs of mice infected with Cryptococcus neoformans, Journal of immunology, 181(1), pp. 610-20.

Pajares et al. (2014)—Diagnostic yield of transbronchial cryobiopsy in interstitial lung disease: A randomized trial, Respirology, 19(6), pp. 900-906.

Pan et al. (2007)—RhoA-mediated apical actin enrichment is required for ciliogenesis and promoted by Foxj1., Journal of cell science, 120(Pt 11), pp. 1868-1876.

Penton-Rol et al. (1999)—Up-regulation of CCR2 chemokine receptor expression and increased susceptibility to the multitropic HIV strain 89.6 in monocytes exposed to glucocorticoid hormones, Journal of immunology, 163(6), pp. 3524-3529.

Philipp-Abbrederis et al. (2015)—In vivo molecular imaging of chemokine receptor CXCR4 expression in patients with advanced multiple myeloma, EMBO molecular medicine, 7(4), pp. 477-87.

Pienta et al. (2013)—Phase 2 study of carlumab (CNTO 888), a human monoclonal antibody against CC-chemokine ligand 2 (CCL2), in metastatic castration-resistant prostate cancer, Investigational New Drugs, 31(3), pp. 760-768.

Prado et al. (2015)—Attenuation of experimental asthma by mycobacterial protein combined with CpG requires a TLR9-dependent IFN-γ-CCR2 signalling circuit, Clinical and Experimental Allergy, 45(9), pp. 1459-1471.

Richmond et al. (1996)—Intrasubject variability in airway inflammation in biopsies in mild to moderate stable asthma, American Journal of Respiratory and Critical Care Medicine, 153(3), pp. 899-903.

Robays et al. (2007)—Chemokine Receptor CCR2 but Not CCR5 or CCR6 Mediates the Increase in Pulmonary Dendritic Cells during Allergic Airway Inflammation, The Journal of Immunology, 178(8), pp. 5305-5311.

Rogers et al. (2003)—MicroPET Imaging of a Gastrin-Releasing Peptide Receptor-Positive Tumor in a Mouse Model of Human Prostate Cancer Using a 64 Cu-Labeled Bombesin Analogue, Bioconjugate Chemistry, 14, pp. 756-763.

Rose, Sung, Fu (2003)—Significant Involvement of CCL2 (MCP-1) in Inflammatory Disorders of the Lung, Microcirculation, 10(3-4), pp. 273-288.

Rosseau et al. (2000)—Phenotypic characterization of alveolar monocyte recruitment in acute respiratory distress syndrome, American journal of physiology. Lung cellular and molecular physiology, 279(1), pp. L25-L35.

Saederup et al. (2010)—Selective chemokine receptor usage by central nervous system myeloid cells in CCR2-red fluorescent protein knock-in mice, PLoS ONE, 5(10), pp. e13693.

Schmall et al. (2015)—Macrophage and cancer cell cross-talk via CCR2 and CX3CR1 is a fundamental mechanism driving lung cancer, American Journal of Respiratory and Critical Care Medicine, 191(4), pp. 437-447.

Schneider, Rasband, Eliceiri (2012)—NIH Image to ImageJ: 25 years of image analysis, Nature Methods, 9(7), pp. 671-675.

Schwarz et al. (2013)—The Future of USP Monographs for PET Drugs, Journal of Nuclear Medicine, 54(3), pp. 472-475.

Schwarz et al. (2014)—Regulatory Requirements for PET Drug Production, Journal of Nuclear Medicine, 55(7), pp. 1132-1137.

Schwarz, Oyama (2015)—The Role of Exploratory Investigational New Drugs for Translating Radiopharmaceuticals into First-in-Human Studies, J Nucl Med, 56, pp. 497-500.

Serbina, Pamer (2006)—Monocyte emigration from bone marrow during bacterial infection requires signals mediated by chemokine receptor CCR2, Nature immunology, 7(3), pp. 311-317.

Shah et al. (2012)—Plasma monocyte chemotactic protein-1 levels at 24 hours are a biomarker of primary graft dysfunction after lung transplantation, Translational Research, 160(6), pp. 435-442.

Sharif-Paghaleh et al. (2015)—Noninvasive Imaging of Activated Complement in Ischemia-Reperfusion Injury Post-Cardiac Transplant, American Journal of Transplantation, 15(9), pp. 2483-2490.

Shen, Wang, Wang (2011)—Role of CCR2 and IL-8 in acute lung injury: a new mechanism and therapeutic target, Expert Rev Respir Med, 5(1), pp. 107-114.

Shiels et al. (2014)—Cigarette smoking and variations in systemic immune and inflammation markers, Journal of the National Cancer Institute, 106(11), pp. 1-8.

Sousa et al. (1994)—Increased expression of the monocyte chemoattractant protein-1 in bronchial tissue from asthmatic subjects, American Journal of Respiratory Cell and Molecular Biology, 10, pp. 142-147.

Speyer et al. (2004)—Novel chemokine responsiveness and mobilization of neutrophils during sepsis, The American journal of pathology, 165(6), pp. 2187-96.

Stafford et al. (1997)—Monocyte chemotactic protein-3 (MCP-3)/fibroblast-induced cytokine (FIC) in eosinophilic inflammation of the airways and the inhibitory effects of an anti-MCP-3/FIC antibody, The Journal of Immunology, 158, pp. 4953-4960.

Steinmüller et al. (2006)—Endotoxin induced peritonitis elicits monocyte immigration into the lung: implications on alveolar space inflammatory responsiveness, Respiratory research, 7, pp. 30.

Stockhofe et al. (2014)—Radiolabeling of nanoparticles and polymers for PET imaging, Pharmaceuticals, 7(4), pp. 392-418.

Struthers, Pasternak (2010)—CCR2 Antagonists, Current Topics in Medicinal Chemistry, 10(13), pp. 1278-1298.

(56) References Cited

OTHER PUBLICATIONS

Su, Shoghi (2008)—Wavelet Denoising in Voxel Based Parametric Estimation of Small Animal PET Images: A Systematic Evaluation of Spatial Constraints and Noise Reduction Algorithms, Physics in Medicine & Biology, 53(21), pp. 5899-5915.

Su, Shoghi (2010)—Single-input-dual-output modeling of image-based input function estimation, Molecular Imaging and Biology, 12(3), pp. 286-294.

Sullivan et al. (2013)—CCR2 antagonist CCX140-B provides renal and glycemic benefits in diabetic transgenic human CCR2 knockin mice, American journal of physiology. Renal physiology, 305(9), pp. F1288-F1297.

Sun et al. (2011)—New concepts of IL-10-induced lung fibrosis: fibrocyte recruitment and M2 activation in a CCL2 / CCR2 axis, Am J Physiol Lung Cell Mol Physiol, 300, pp. L341-L353.

Swirski et al. (2009)—Identification Monocytes Inflammatory of Splenic Reservoir and Their Deployment Sites, Science, 325(5940), pp. 612-616.

Tacke, Randolph (2006)—Migratory fate and differentiation of blood monocyte subsets, Immunobiology, 211(6-8), pp. 609-618.

Thomas et al. (1999)—MIRD Pamphlet No. 14: a dynamic urinary bladder model for radiation dose calculations, Journal of Nuclear Medicine, 40, 4, pp. 102S-123S.

Tomankova, Kriegova, Liu (2015)—Chemokine receptors and their therapeutic opportunities in diseased lung: far beyond leukocyte trafficking, American journal of physiology. Lung cellular and molecular physiology, 308(7), pp. L603-L618.

Traves et al. (2002)—Increased levels of the chemokines GROalpha and MCP-1 in sputum samples from patients with COPD, Thorax, 57(7), pp. 590-595.

Tsou et al. (2007)—Critical roles for CCR2 and MCP-3 in monocyte mobilization from bone marrow and recruitment to inflammatory sites, Journal of Clinical Investigation, 117(4), pp. 902-909.

Tyner et al. (2006)—Blocking airway mucous cell metaplasia by inhibiting EGFR antiapoptosis and IL-13 transdifferentiation signals, Journal of Clinical Investigation, 116(2), pp. 309-321.

Valenca et al. (2005)—Sodium pertechnetate (Na99mTcO4) biodistribution in mice exposed to cigarette smoke, BMC nuclear medicine, 5(1), pp. 1-5.

Van Rooijen, Sanders (1994)—Liposome mediated depletion of macrophages: mechanism of action, preparation of liposomes and applications, Journal of Immunological Methods, 174, pp. 83-93.

Vergunst et al. (2008)—Modulation of CCR2 in rheumatoid arthritis: A double-blind, randomized, placebo-controlled clinical trial, Arthritis and Rheumatism, 58(7), pp. 1931-1939.

Volpe et al. (2012)—CCR2 acts as scavenger for CCL2 during monocyte chemotaxis, PLoS ONE, 7(5), e37208.

Walter et al. (2001)—Interleukin 12 p40 production by barrier epithelial cells during airway inflammation., The Journal of experimental medicine, 193(3), pp. 339-351.

Wang et al. (2012)—In vivo imaging implicates CCR2+monocytes as regulators of neutrophil recruitment during arthritis, Cell Immunology, 278, pp. 103-112.

Weiss, Jacobson (2013)—Molecular imaging of chemokine receptor CXCR4, Theranostics, 3(1), pp. 76-84.

Werengowska-Cietwierz et al. (2015)—The Chemistry of Bioconjugation in Nanoparticles-Based Drug Delivery System, Advances in Condensed Matter Physics, 2015, pp. 1-27.

Wester et al. (2015)—Disclosing the CXCR4 expression in lymphoproliferative diseases by targeted molecular imaging, Theranostics, 5(6), pp. 618-630.

Yang et al. (2010)—Roles of CC chemokine receptors (CCRs) on lipopolysaccharide-induced acute lung injury, Respiratory physiology & neurobiology, 170(3), pp. 253-259.

Zhao et al. (2014)—Facile synthesis, pharmacokinetic and systemic clearance evaluation, and positron emission tomography cancer imaging of $^{64}Cu$—Au alloy nanoclusters, Nanoscale, 6(22), pp. 13501-13509.

* cited by examiner

SEQUENCE LISTING

<160> NUMBER OF SEQ ID NOS: 30

<210> SEQ ID NO 1
<211> LENGTH: 5
<212> TYPE: PRT
<213> ORGANISM: Artificial Sequence
<220> FEATURE:
<223> OTHER INFORMATION: synthetic peptide

<400> SEQUENCE: 1

Thr Phe Leu Lys Cys
1               5

<210> SEQ ID NO 2
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: "Xaa in position 1" is absent, is glycine or
      represents an amino acid sequence selected from the group
      consisting of LG, YLG, and HYLG
<220> FEATURE:
<221> NAME/KEY: MISC_FEATURE
<222> LOCATION: (7)..(7)
<223> OTHER INFORMATION: "Xaa in position 7" independently is absent, is
      methionine, or represents an amino acid sequence selected from the
      group consisting of MA, MAN, MANG, MANGF, MANGFV, MANGFVW,
      MANGFVWE, and MANGFVWEN

<400> SEQUENCE: 2

Xaa Thr Phe Leu Lys Cys Xaa
1               5

<210> SEQ ID NO 3
<211> LENGTH: 7
<212> TYPE: PRT
<213> ORGANISM: Artificial Sequence
<220> FEATURE:
<223> OTHER INFORMATION: Peptide

<400> SEQUENCE: 3

Leu Gly Thr Phe Leu Lys Cys
1               5

<210> SEQ ID NO 4
<211> LENGTH: 11
<212> TYPE: PRT
<213> ORGANISM: Artificial Sequence
<220> FEATURE:
<223> OTHER INFORMATION: synthetic peptide

<400> SEQUENCE: 4

His Tyr Leu Gly Thr Phe Leu Lys Cys Met Ala
1               5                   10

<210> SEQ ID NO 5
<211> LENGTH: 9
<212> TYPE: PRT
<213> ORGANISM: Artificial Sequence
<220> FEATURE:
<223> OTHER INFORMATION: synthetic peptide

<400> SEQUENCE: 5

Leu Gly Thr Phe Leu Lys Cys Met Ala
1               5

<210> SEQ ID NO 6
<211> LENGTH: 9
<212> TYPE: PRT
<213> ORGANISM: Artificial Sequence
<220> FEATURE:
<223> OTHER INFORMATION: synthetic peptide

```
<400> SEQUENCE: 6

His Tyr Leu Gly Thr Phe Leu Lys Cys
1               5

<210> SEQ ID NO 7
<211> LENGTH: 11
<212> TYPE: PRT
<213> ORGANISM: Artificial Sequence
<220> FEATURE:
<223> OTHER INFORMATION: synthetic peptide

<400> SEQUENCE: 7

Gly Thr Phe Leu Lys Cys Met Ala Asn Gly Phe
1               5                   10

<210> SEQ ID NO 8
<211> LENGTH: 11
<212> TYPE: PRT
<213> ORGANISM: Artificial Sequence
<220> FEATURE:
<223> OTHER INFORMATION: synthetic peptide

<400> SEQUENCE: 8

Thr Phe Leu Lys Cys Met Ala Asn Gly Phe Val
1               5                   10

<210> SEQ ID NO 9
<211> LENGTH: 18
<212> TYPE: PRT
<213> ORGANISM: Artificial Sequence
<220> FEATURE:
<223> OTHER INFORMATION: synthetic peptide

<400> SEQUENCE: 9

His Tyr Leu Gly Thr Phe Leu Lys Cys Met Ala Asn Gly Phe Val Trp
1               5                   10                  15

Glu Asn

<210> SEQ ID NO 10
<211> LENGTH: 7
<212> TYPE: PRT
<213> ORGANISM: Artificial Sequence
<220> FEATURE:
<223> OTHER INFORMATION: synthetic peptide

<400> SEQUENCE: 10

Cys Lys Leu Phe Thr Gly Leu
1               5

<210> SEQ ID NO 11
<211> LENGTH: 5
<212> TYPE: PRT
<213> ORGANISM: Artificial Sequence
<220> FEATURE:
<223> OTHER INFORMATION: synthetic peptide

<400> SEQUENCE: 11

Leu Phe Thr Lys Cys
1               5

<210> SEQ ID NO 12
<211> LENGTH: 5
<212> TYPE: PRT
<213> ORGANISM: Artificial Sequence
<220> FEATURE:
<223> OTHER INFORMATION: synthetic peptide
```

<400> SEQUENCE: 12

Cys Lys Thr Phe Leu
1               5

<210> SEQ ID NO 13
<211> LENGTH: 7
<212> TYPE: PRT
<213> ORGANISM: Artificial Sequence
<220> FEATURE:
<223> OTHER INFORMATION: synthetic peptide

<400> SEQUENCE: 13

His Thr Leu Met Arg Asn Leu
1               5

<210> SEQ ID NO 14
<211> LENGTH: 7
<212> TYPE: PRT
<213> ORGANISM: Artificial Sequence
<220> FEATURE:
<223> OTHER INFORMATION: synthetic peptide

<400> SEQUENCE: 14

Leu Asn Arg Met Leu Thr His
1               5

<210> SEQ ID NO 15
<211> LENGTH: 7
<212> TYPE: PRT
<213> ORGANISM: Artificial Sequence
<220> FEATURE:
<223> OTHER INFORMATION: synthetic peptide

<400> SEQUENCE: 15

Leu Asn Thr Phe Gln Glu Phe
1               5

<210> SEQ ID NO 16
<211> LENGTH: 7
<212> TYPE: PRT
<213> ORGANISM: Artificial Sequence
<220> FEATURE:
<223> OTHER INFORMATION: synthetic peptide

<400> SEQUENCE: 16

Phe Glu Gln Phe Thr Asn Leu
1               5

<210> SEQ ID NO 17
<211> LENGTH: 4
<212> TYPE: PRT
<213> ORGANISM: Artificial Sequence
<220> FEATURE:
<223> OTHER INFORMATION: synthetic peptide

<400> SEQUENCE: 17

Thr Phe Leu Lys
1

<210> SEQ ID NO 18
<211> LENGTH: 6
<212> TYPE: PRT
<213> ORGANISM: Artificial Sequence
<220> FEATURE:
<223> OTHER INFORMATION: synthetic peptide
<220> FEATURE:

```
<221> NAME/KEY: MISC_FEATURE
<222> LOCATION: (1)..(1)
<223> OTHER INFORMATION: "Xaa in position 1" is absent, is glycine or
      represents an amino acid sequence selected from the group
      consisting of AG, LG, YLG and HYLG
<220> FEATURE:
<221> NAME/KEY: MISC_FEATURE
<222> LOCATION: (6)..(6)
<223> OTHER INFORMATION: "Xaa in position 6" independently is absent or
      is alanine

<400> SEQUENCE: 18

Xaa Thr Phe Leu Lys Xaa
1               5

<210> SEQ ID NO 19
<211> LENGTH: 6
<212> TYPE: PRT
<213> ORGANISM: Artificial Sequence
<220> FEATURE:
<223> OTHER INFORMATION: synthetic peptide

<400> SEQUENCE: 19

Leu Gly Thr Phe Leu Lys
1               5

<210> SEQ ID NO 20
<211> LENGTH: 7
<212> TYPE: PRT
<213> ORGANISM: Artificial Sequence
<220> FEATURE:
<223> OTHER INFORMATION: synthetic peptide

<400> SEQUENCE: 20

Ala Gly Thr Phe Leu Lys Cys
1               5

<210> SEQ ID NO 21
<211> LENGTH: 7
<212> TYPE: PRT
<213> ORGANISM: Artificial Sequence
<220> FEATURE:
<223> OTHER INFORMATION: synthetic peptide

<400> SEQUENCE: 21

Leu Gly Thr Phe Leu Lys Ala
1               5

<210> SEQ ID NO 22
<211> LENGTH: 5
<212> TYPE: PRT
<213> ORGANISM: Artificial Sequence
<220> FEATURE:
<223> OTHER INFORMATION: synthetic peptide

<400> SEQUENCE: 22

Gly Thr Phe Leu Lys
1               5

<210> SEQ ID NO 23
<211> LENGTH: 7
<212> TYPE: PRT
<213> ORGANISM: Artificial Sequence
<220> FEATURE:
<223> OTHER INFORMATION: synthetic peptide

<400> SEQUENCE: 23

Ala Gly Thr Phe Leu Lys Ala
```

```
1               5

<210> SEQ ID NO 24
<211> LENGTH: 4
<212> TYPE: PRT
<213> ORGANISM: Artificial Sequence
<220> FEATURE:
<223> OTHER INFORMATION: synthetic peptide

<400> SEQUENCE: 24

Met Ala Asn Gly
1

<210> SEQ ID NO 25
<211> LENGTH: 5
<212> TYPE: PRT
<213> ORGANISM: Artificial Sequence
<220> FEATURE:
<223> OTHER INFORMATION: synthetic peptide

<400> SEQUENCE: 25

Met Ala Asn Gly Phe
1               5

<210> SEQ ID NO 26
<211> LENGTH: 6
<212> TYPE: PRT
<213> ORGANISM: Artificial Sequence
<220> FEATURE:
<223> OTHER INFORMATION: synthetic peptide

<400> SEQUENCE: 26

Met Ala Asn Gly Phe Val
1               5

<210> SEQ ID NO 27
<211> LENGTH: 7
<212> TYPE: PRT
<213> ORGANISM: Artificial Sequence
<220> FEATURE:
<223> OTHER INFORMATION: synthetic peptide

<400> SEQUENCE: 27

Met Ala Asn Gly Phe Val Trp
1               5

<210> SEQ ID NO 28
<211> LENGTH: 8
<212> TYPE: PRT
<213> ORGANISM: Artificial Sequence
<220> FEATURE:
<223> OTHER INFORMATION: synthetic peptide

<400> SEQUENCE: 28

Met Ala Asn Gly Phe Val Trp Glu
1               5

<210> SEQ ID NO 29
<211> LENGTH: 9
<212> TYPE: PRT
<213> ORGANISM: Artificial Sequence
<220> FEATURE:
<223> OTHER INFORMATION: synthetic peptide

<400> SEQUENCE: 29

Met Ala Asn Gly Phe Val Trp Glu Asn
1               5
```

```
<210> SEQ ID NO 30
<211> LENGTH: 4
<212> TYPE: PRT
<213> ORGANISM: Artificial Sequence
<220> FEATURE:
<223> OTHER INFORMATION: synthetic peptide

<400> SEQUENCE: 30

His Tyr Leu Gly
1
```

METHODS FOR DETECTING CCR2 RECEPTORS

CROSS-REFERENCE TO RELATED APPLICATIONS

This application is a Divisional of U.S. Nonprovisional application Ser. No. 15/611,577 filed on 1 Jun. 2017 which claims priority from U.S. Provisional Application Ser. No. 62/344,677 filed on 2 Jun. 2016, which is incorporated herein by reference in its entirety.

STATEMENT REGARDING FEDERALLY SPONSORED RESEARCH OR DEVELOPMENT

This invention was made with government support under grant number HHSN268201000046C, HL131908, HL094601, and HL139714 awarded by National Institutes of Health. The government has certain rights in the invention. This work was supported by the U.S. Department of Veterans Affairs, and the Federal Government has certain rights in this invention.

MATERIAL INCORPORATED-BY-REFERENCE

The Sequence Listing, which is a part of the present disclosure, includes a computer readable form comprising nucleotide and/or amino acid sequences of the present invention. The subject matter of the Sequence Listing is incorporated herein by reference in its entirety.

FIELD OF THE INVENTION

The present disclosure generally relates to compositions of imaging agents and methods of making and detection thereof.

SUMMARY OF THE INVENTION

Among the various aspects of the present disclosure is the provision of compositions of imaging agents for use in detecting, monitoring, and evaluating CCR2 associated diseases, disorders, and conditions.

Briefly, therefore, the present disclosure is directed to compositions and methods to detect, monitor, and evaluate conditions associated with CCR2 upregulation or overexpression.

The present disclosure provides for compositions for imaging agents.

The present disclosure provides for pharmaceutical composition comprising the imaging agents.

The present disclosure provides for methods for imaging inflammation associated with diseases, disorders, and conditions associated with CCR2.

The present disclosure provides for imaging agents comprising a CCR2 binding peptide; a radiolabel; and a nanoparticle, a chelator, or a linker.

In some embodiments, the imaging agent further comprises a linker.

In some embodiments, the CCR2 binding peptide comprises a linear ECL1 peptide or a cyclized ECL1i peptide; an amino acid sequence Thr-Phe-Leu-Lys (SEQ ID NO: 17); SEQ ID NO: 17 comprising one or more chemical modifications that confer resistance to proteolysis; SEQ ID NO: 17 comprising one or more conservative substitutions; Thr-Phe-Leu-Lys-Cys (SEQ ID NO: 1); SEQ ID NO: 1 comprising one or more chemical modifications that confer resistance to proteolysis; SEQ ID NO: 1 comprising one or more conservative substitutions; X1-TFLKC-X2 (SEQ ID NO: 2), wherein X1 is absent, is glycine, or represents an amino acid sequence selected from the group consisting of AG, LG, YLG, and HYLG; and X2 independently is absent, is methionine, or represents an amino acid sequence selected from the group consisting of MA, MAN, MANG, MANGF, MANGFV, MANGFVW, MANGFVWE, and MANGFV-WEN; SEQ ID NO: 2 comprising one or more chemical modifications that confer resistance to proteolysis; SEQ ID NO: 2 comprising one or more conservative substitutions; X1-TFLK-X3 (SEQ ID NO: 18), wherein X1 is absent, is glycine, or represents an amino acid sequence selected from the group consisting of AG, LG, YLG, and HYLG; and X3 independently is absent or is alanine; SEQ ID NO: 18 comprising one or more chemical modifications that confer resistance to proteolysis; or SEQ ID NO: 18 comprising one or more conservative substitutions.

In some embodiments, the CCR2 binding peptide comprises amino acids and all or a portion of the amino acids are in L configuration or in D configuration; the imaging agent is stored in a physiological pH, optionally, at about pH of 7.4; the CCR2 binding peptide is covalently linked to the nanoparticle; or the CCR2 binding peptide is no more than 18 amino acids in length.

In some embodiments, the CCR2 binding peptide is selected from the group consisting of: LGTFLKC (SEQ ID NO: 3); HYLGTFLKCMA (SEQ ID NO: 4); LGTFLKCMA (SEQ ID NO: 5); HYLGTFLKC (SEQ ID NO: 6); GTFLKCMANGF (SEQ ID NO: 7); TFLKCMANGFV (SEQ ID NO: 8); HYLGTFLKCMANGFVWEN (SEQ ID NO: 9); LGTFLK (SEQ ID NO: 19); AGTFLKC (SEQ ID NO: 20); LGTFLKA (SEQ ID NO: 21); GTFLK (SEQ ID NO: 22); AGTFLKA (SEQ ID NO: 23); a sequence deriving from any of SEQ ID NO: 3 to 10, or 19 to 23 by one or more chemical modifications that confer resistance to proteolysis; or a sequence deriving from any of SEQ ID NO: 3 to 9 or 19 to 23 by one or more conservative substitutions.

In some embodiments, the CCR2 binding peptide consists of LGTFLKC (SEQ ID NO: 3).

In some embodiments, the radiolabel comprises $^2$H (D or deuterium), $^3$H (T or tritium), $^{11}$C, $^{13}$C, $^{14}$C, $^{64}$Cu, $^{67}$Cu, $^{177}$Lu, $^{13}$N, $^{15}$N, $^{15}$O, $^{17}$O, $^{18}$O, $^{18}$F, $^{89}$Sr, $^{35}$S, $^{153}$Sm, $^{36}$Cl, $^{82}$Br, $^{75}$Br, $^{76}$Br, $^{77}$Br, $^{123}$I, $^{124}$I, $^{125}$I, $^{131}$I, $^{111}$In, $^{67}$Ga, $^{68}$Ga, $^{177}$Lu $^{186}$Re, $^{188}$Re, $^{201}$Tl $^{99m}$Tc, $^{90}$Y, or $^{89}$Zr; the radiolabel comprises oxygen-15 water, nitrogen-13 ammonia, [$^{82}$Rb] rubidium-82 chloride, [$^{11}$C], [$^{11}$C] 25B-NBOMe, [$^{18}$F] Altanserin, [$^{11}$C] Carfentanil, [$^{11}$C] DASB, [$^{11}$C] DTBZ, [$^{18}$F] Fluoropropyl-DTBZ, [$^{11}$C] ME@HAPTHI, [$^{18}$F] Fallypride, [$^{18}$F] Florbetaben, [$^{18}$F] Flubatine, [$^{18}$F] Fluspidine, [$^{18}$F] Florbetapir, [$^{18}$F] or [$^{11}$C] Flumazenil, [$^{18}$F] Flutemetamol, [$^{18}$F] Fluorodopa, [$^{18}$F] Desmethoxyfallypride, [$^{18}$F] Mefway, [$^{18}$F] MPPF, [$^{18}$F] Nifene, Pittsburgh compound B, [$^{11}$C] Raclopride, [$^{18}$F] Setoperone, [$^{18}$F] or [$^{11}$C] N-Methylspiperone, [$^{11}$C] Verapamil, [$^{11}$C] Martinostat, Fludeoxyglucose ($^{18}$F)(FDG)-glucose analogue, [$^{11}$C] Acetate, [$^{11}$C] Methionine, [$^{11}$C] Choline, [$^{18}$F] Fluciclovine, [$^{18}$F] Fluorocholine, [$^{18}$F] FET, [$^{18}$F] FMISO, [$^{18}$F] 3'-fluoro-3'-deoxythymidine, [$^{68}$Ga] DOTA-pseudopeptides, [$^{68}$Ga] PSMA, or [$^{18}$F] Fluorodeoxysorbitol (FDS); the chelator comprises NHS-MAG3, MAG3, DTPA, 3p-C-NE3TA, 3p-C-NOTA, 3p-C-DE4TA, ATSM, tetraazamacrocyclic ligands (e.g., DOTA (1,4,7,10-tetraazacyclododecane-1,4,7,10-tetraacetic acid), DOTA-NHS, pSCN-Bn-DOTA, pNH$_2$-Bn-DOTA, TETA (1,4,8,11-tetraazacyclotetradecane-1,4,8,11-tetraacetic acid, TETA-octreotide (OC)), hexaazamacrobicyclic cage-type ligands (e.g., Sarcophogine chelators), cross-bridged tetraamine ligands (e.g., CB-TE2A (4,11-bis(carboxymethyl)-1,4,8,11-tetraazabicyclo[6.6.2]hexadecane)), 6-Hydrazinopyridine-3-carboxylic acid (Hynic), NHS-Hynic, 2,2',2"-(10-(2-((2-(2,5-dioxo-2,5-dihydro-1H-pyrrol-1-yl)ethyl)amino)-2-oxoethyl)-1,4,7,10-tetraazacyclododecane-1,4,7-triyl) triacetic acid (Maleimido-mono-amide-DOTA); or the nanoparticle comprises a nanocluster or nanostructure; organic, inorganic, or lipid nanostructures; the nanoparticle comprises iron oxide, gold, gold nanoclusters (AuNC), gold nanorods (AuNR), copper (Cu), quantum dots, carbon nanotubes, carbon nanohorn, gadolinium (Gd), dendrimers, dendrons, polyelectrolyte complex (PEC) nanoparticles, calcium phosphate nanoparticles, perfluorocarbon nanoparticles (PFCNPs), lipid-based nanoparticles, liposomes, or micelles; or the linker comprises a chemical or physical bond; PEG, TA-PEG-Maleimide, TA-PEG-OMe, TA-PEG, an isothiocyanate group, a carboxylic acid or carboxylate groups, a dendrimer, a dendron, Fmoc-protected-2,3-diaminopropanoic acid, ascorbic acid, a silane linker, minopropyltrimethoxysilane (APTMS), dopamine, 2 thiol groups, 2 primary amines, a carboxylic acid and primary amine, maleimide and thiol, hydrazide and aldehyde, or a primary amine and aldehyde, an amide, a thioether, a disulfide, an acetyl-hydrazone group, a polycyclic group, a click chemistry (CC) group.

In some embodiments, the chelator is conjugated to the CCR2 binding peptide and the chelator is radiolabeled; or the CCR2 binding peptide is conjugated to a nanoparticle.

In some embodiments, the radiolabel is $^{64}$Cu.

In some embodiments, the CCR2 binding peptide is conjugated to a nanoparticle comprising a gold nanocluster.

In some embodiments, the gold nanocluster is loaded with a radiolabel.

In some embodiments, the chelator comprises a tetraazamacrocyclic ligand; DOTA; TETA; or 2,2',2"-(10-(2-((2-(2,5-dioxo-2,5-dihydro-1H-pyrrol-1-yl)ethyl)amino)-2-oxoethyl)-1,4,7,10-tetraazacyclododecane-1,4,7-triyl) triacetic acid (Maleimido-mono-amide-DOTA).

In some embodiments, the chelator is conjugated to a cysteine residue of the CCR2 binding peptide.

In some embodiments, the imaging agent comprises: a $^{64}$Cu-DOTA-ECL1i PET or SPECT imaging agent; an ECL1i peptide conjugated to a gold nanocluster, wherein the gold nanocluster is loaded with $^{64}$Cu; $^{64}$Cu-DOTA-ECL1i; $^{64}$CuAuNCs-ECL1i; a multivalent imaging agent (optionally, $^{64}$CuAuNCs-ECL1i), exhibiting extended pharmacokinetics for long-term CCR2 receptor detection and targeted theranostics; or a monovalent (optionally, $^{64}$Cu-DOTA-ECL1i), exhibiting fast pharmacokinetics for efficiently for rapid or serial imaging of CCR2 receptors.

In some embodiments, the imaging agent is a PET imaging agent; is a SPECT imaging agent; targets CCR2 receptors; detects CCR2 receptor up-regulation; or detects elevated CCR2 expression.

Another aspect of the present disclosure provides for a method of detecting a CCR2 receptor comprising administering to a subject an imaging agent or detecting the imaging agent.

In some embodiments, the detecting of the CCR2 receptor comprises positron emission tomography (PET) imaging, and single photon emission computed tomography (SPECT) imaging, mass spectrometry, gamma imaging, magnetic resonance imaging (MRI), magnetic resonance spectroscopy, fluorescence spectroscopy, CT, ultrasound, or X-ray.

In some embodiments, the method detects a CCR2 associated disease, disorder, or condition is selected from the group consisting of: atherosclerosis; abdominal aortic aneurysm; acquired metabolic disease; acute cystitis; acute lung injury; acute proliferative glomerulonephritis; acute or chronic sinusitis; age-related macular degeneration; alcoholic hepatitis; allergic asthma; allergic conjunctivitis; allergic rhinitis; alveolitis; angiostenosis; anthracosis; ariboflavinosis; arteriosclerosis; artery disease; arthritis; asthma; atherogenesis; atheroma; atherosclerosis; atopic dermatitis; autoimmune disease; autoinflammation; bacterial infection; bacteriuria; bladder cancer; bone cancer; bone inflammation disease; brain trauma; breast cancer; bronchiolitis; bronchiolitis obliterans syndrome; cancer; cardiac infarction; cardiovascular disease; carotid artery disease; CCR2 associated neurological disorders; Cd3zeta deficiency; central nervous system disease; cerebral aneurysms; cervical cancer; chagas disease; chorioamnionitis; chronic heart failure; chronic lung disease; chronic lymphocytic leukemia; chronic myelocytic leukemia; chronic obstructive pulmonary disease (COPD); chronic respiratory viral infection; chronic urticaria; colitis; colon cancer; complex regional pain syndrome; coronary artery aneurysm; crescentic glomerulonephritis; Crohn's Disease; cystitis; cytomegalovirus retinitis; degeneration of macula and posterior pole; demyelinating disease; dengue shock syndrome; denture stomatitis; dermatosis syndrome; diabetes; diabetes mellitus, noninsulin-dependent; diabetic angiopathy; diabetic complications; diabetic macular edema; diabetic microangiopathy; diabetic nephropathy; diabetic retinitis; diabetic retinopathy; diastolic cardiomyopathies; encephalitis; endocervicitis; endometrial stromal sarcoma; endometriosis; Erdheim-Chester disease; extrapulmonary tuberculosis; extrinsic cardiomyopathy; eye disease; fibroid lung; fungal pneumonia; gingivitis; glomerulonephritis; gum disease; Hamman-Rich syndrome; head and neck cancer, herpes simplex virus keratitis; HIV-1; Hodgkin's disease; hyperhomocysteinemia; idiopathic anterior uveitis; idiopathic interstitial pneumonia; idiopathic pulmonary fibrosis; inflammation after cataract surgery; inflammatory bowel diseases; inflammatory disease; influenza; interstitial lung disease; invasive staphyloccocia; ischemia of lower members of the heart; ischemia-reperfusion injury; Israeli tick typhus; Kawasaki disease; keratitis; kidney disease; leptospirosis; limb ischemia; lipid pneumonia; lipodystrophy; lipoid nephrosis; lung cancer; lung disease; lung injury; lung transplantation; macular degeneration, age-related, 1; macular holes; malaria; malignant myeloma; mast-cell leukemia; meningitis; mesangial proliferative glomerulonephritis; metabolic disease; microvascular complications of diabetes 1; monocytic leukemia; multiple myeloma; multiple sclerosis; *Mycobacterium tuberculosis*; myocardial infarction; myocarditis; necrosis; neovascular inflammatory disease; nephritis; nephrosclerosis; neural tube defects; neuritis; neuroinflammation; nonspecific interstitial pneumonia; obesity; ophthalmic disorder; organ allograft rejection; overnutrition; pain; pain from a sciatic nerve; papillary conjunctivitis; pelvic inflammatory disease; periodontitis; periodontal diseases; periodontitis; peripheral artery disease; peripheral pain; peritonitis; pleural tuberculosis; pleurisy; pneumoconiosis; pneumonia; post-thrombotic syndrome; primary graft dysfunction (PGD) (a reperfusion injury after transplant); proliferative glomerulonephritis; prostate cancer; psoriasis; psoriatic arthritis; pulmonary alveolar proteinosis; pulmonary fibrosis; pulmonary sarcoidosis; purulent labyrinthitis; pyelonephritis; radiculopathy; renal fibrosis; renal insufficiency; reperfusion disorders; respiratory system disease; restenosis; retinal degeneration; retinal vascular occlusion; retinal vasculitis; retinal vein occlusion; rheumatoid arthritis; rhinoscleroma; sarcoidosis; sarcoidosis 1; scleritis; secondary progressive multiple sclerosis; severe acute respiratory syndrome; silicosis; solid tumor; stachybotrys chartarum; stomach cancer; stromal keratitis; systemic lupus erythematosus; transient cerebral ischemia; transplant arteriosclerosis; trypanosomiasis; tuberculosis; tuberculous meningitis; type II diabetes; ulcerative colitis; ureteral disease; urinary system disease; urinary tract obstruction; uveitis; vangl1-related neural tube defect; vascular disease; vascular permeability and attraction of immune cells during metastasis; vasculitis; verruciform xanthoma of skin; viral infection; viral encephalitis; viral meningitis; vitreoretinopathy; or xanthogranulomatous pyelonephritis; acute lung injury; inflammation; primary graft dysfunction (PGD); asthma; pulmonary fibrosis; COPD; atherosclerosis; lung transplant; lung injury; COPD; atherosclerosis; cancer; prostate cancer; organ transplant; metabolic disease, type II diabetes; multiple sclerosis; rheumatoid arthritis; pain; pulmonary fibrosis; or reperfusion in a lung transplant; inflammation associated with a CCR2 associated disease, disorder, or condition; or inflammation associated with lung injury, graft transplantation, atherosclerosis, tumor cells, or cancer.

In some embodiments, the method further comprises evaluating or monitoring a CCR2 associated disease, disorder, or condition; or administering a CCR2 antagonist to a subject.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

(FIG. 2A) HPLC profiles of DOTA-ECL1i (UV, black) and $^{64}$Cu-DOTA-ECL1i (radioactivity, green); (FIG. 2B) Mass spectrometry spectrum of Cu-DOTA-CCR2 (arrow).

(FIG. 3A) Arterial paO$_2$ levels 6 h after transplantation of B6 wild type (WT) lungs into B6 wild type (n=4) or B6 CCR2-deficient (CCR2$^{-/-}$) (n=4) recipients. **p<0.05. Contour plots depicting recipient (CD45.2) versus donor (CD45.1) hematopoietic cells in B6 CD45.1 lung grafts 6 hours after transplantation into (FIG. 3B) B6 CD45.2 wild type or (FIG. 3C) B6 CD45.2 CCR2-deficient hosts. Monocytes (CD11b$^+$Ly6C$^{hi}$) are gated on recipient (CD45.2) (top panels) or donor (CD45.1) (bottom) hematopoietic cells. Numbers are percentages in respective gates. Histograms depict CCR2 expression on recipient (CD45.2) (top) or donor (CD45.1) (bottom) monocytes. Solid line: CCR2; shaded: isotype control). Plots in (FIG. 3A) and (FIG. 3B) are representative of at least 3 independent experiments in each group. Lung grafts were stored in low potassium dextran solution at 4° C. for 18 hours prior to transplantation.

(FIG. 5A) Synthetic scheme of $^{64}$CuAuNCs-ECL1i. (FIG. 5B) Transmission electron microscopy and (FIG. 5C) dynamic light scattering of decayed CuAuNCs-ECL1i.

(FIG. 6A) $^{64}$Cu-DOTA-ECL1i showed rapid renal clearance at 1 hour and (FIG. 6B) $^{64}$CuAuNCs-ECL1i showed extended pharmacokinetics at 1, 4, and 24 hours (n=4/group).

(FIG. 7A) Representative $^{15}$O-water PET image at 1 hour following B6 wild type→B6 wild type lung transplantation showing comparable signals in both lungs. The PET imaging was performed as a 0-10 dynamic scan immediately after the injection of $^{15}$O-water. (FIG. 7B) Quantitative uptake of $^{15}$O-water in native lungs and donor grafts showing comparable signals (n=4).

(FIG. 8A) Representative $^{64}$CuDOTA-ECL1i PET/CT images in B6 wild type→B6 wild type and B6 wild type→B6 CCR2-deficient lung transplant combinations at 1, 4 and 24 hours after transplantation. Tracer uptake was observed in the donor lungs in both models. Quantitative uptake analysis in lung grafts and native lungs after (FIG. 8B) B6 wild type→B6 CCR2-deficient and (FIG. 8C) B6 wild type→B6 wild type pulmonary transplantation. L: liver, K: kidney, B: bladder. Circle: donor lung (n=4/group).

(FIG. 10A) Representative $^{64}$Cu-DOTA-ECL1i PET blocking image during a 0-60 min dynamic scan. PET imaging was performed at 1 hour after B6 wild type→B6 wild type lung transplantation with the co-injection of non-radiolabeled ECL1i and $^{64}$Cu-DOTA-ECL1i at 1000:1 molar ratio. Circle outlines uptake in donor graft. (FIG. 10B) Quantitative uptake of $^{64}$Cu-DOTA-ECL1i in native lungs and donor grafts showing comparable accumulation. (FIG. 10C) Bar graph shows donor graft/native lung SUV uptake ratio (n=4).

(FIG. 11A) Representative $^{18}$F-FDG PET image obtained at 1 hour after lung transplantation showing uptake in the donor lung after B6 wild type→B6 wild type lung transplantation. (FIG. 11B) Quantitative uptake of $^{18}$F-FDG in native lungs and donor grafts (n=4).

(FIG. 12A) Representative $^{64}$CuAuNCs-ECL1i and $^{64}$CuAuNCs nanoclusters PET/CT images in B6 wild type→B6 wild type lung transplantation model at 24 hours following engraftment. The targeted nanocluster showed significant uptake in the donor lung while the non-targeted counterpart showed minimum non-specific retention. Quantitative uptake analysis of (FIG. 12B) $^{64}$CuAuNCs and (FIG. 12C) $^{64}$CuAuNCs-ECL1i in lung grafts and native lungs after B6 wild type→B6 wild type pulmonary transplantation and (FIG. 12D) Donor graft/native lung uptake ratios for $^{64}$CuAuNCs-ECL1i and $^{64}$CuAuNCs PET after B6 wild type→B6 wild type pulmonary transplantation. Circle: donor lung (n=4/group).

(FIG. 13A) PET images of mice post intratracheal PBS or LPS, injected with i.v. $^{64}$Cu-DOTA-vMIP-II for PET at 3-144 h later. White arrow indicates the vMIP-II lung signal. (FIG. 13B) Standardized uptake value (SUV) of lung images. n=3-8 mice/time point. (FIG. 13C) Mean fluorescent intensity (MFI) of cell types from lung digests co-localized DOTA-vMIP-II-Dylight550 by flow cytometry. Mice were injected with DOTA-vMIP-II-Dylight550 at 24 or 48 h post PBS or LPS. n=4 experiments, *p<0.05 compared to PBS.

(FIG. 14A, FIG. 14B) Immunostaining for CCR2. (FIG. 14C, FIG. 14D) PET/CT images of mice injected with i.v. $^{64}$Cu-DOTA-ECL1i at 24 h. White arrow indicates lung signal. (FIG. 14E) Quantitation of lung images at 24-144 h post-LPS. (FIG. 14F) Dose-response (20-fold) and non-PBS controls, naïve and CCR2 null mice. Blocked were mice treated with excess cold tracer. n=3-8 mice/time point. (FIG. 14G) Biodistribution at 24 h. *p<0.05 LPS compared to PBS treatment.

(FIG. 16A) Immunostaining for CCR2, bar, 50 µm B. Quantitation of A, p<0.05. (FIG. 16C) Autoradiography of $^{64}$Cu-DOTA-ECL1i binding of lung tissues sections on glass slides. (FIG. 16D) Flow cytometry of CD45$^+$ ECL1i-647$^+$ cells from a digested COPD lung sample.

(FIG. 19A) Peptide labeling and stability. (FIG. 19B) Mouse imaging studies. The number of mice in each treatment group is indicated. Bold boxes indicate in vivo PET/CT imaging studies. Time-activity analysis was performed on a subgroup of PET images obtained at 24 h post-treatment. (FIG. 19C) Human lung tissues studies. A subgroup of lung tissues from subjects with COPD displaying elevated levels of CCR2 positive cells was analyzed for $^{64}$Cu-DOTA-ECL1i binding using autoradiography followed by blocking (n=6).

(FIG. 20A) Mass spectrometry of DOTA-ECL1i (arrow). (FIG. 20B) DOTA-ECL1i was labeled with $^{64}$Cu and assayed for chemical purity and radiochemical purity determined by HPLC. Shown are profiles of DOTA-ECL1i (UV, black) and $^{64}$Cu-DOTA-ECL1i (radioactivity, green).

(FIG. 22A) Immunostaining for CCR2, 24 h after intratracheal PBS or LPS delivery. Tissues were counterstained with hematoxylin. Images were captured at 400× magnification, bar=50 µm. (FIG. 22B) Biodistribution of $^{64}$Cu-DOTA-ECL1i at 24 h, compared to the PBS and naive groups. Shown is the mean±SD, n=4/group, *P<0.001 by two-way ANOVA with Tukey's test.

FIG. 23A. Representative PET images of maximum intensity projections (MIP) reconstructed PET/CT (center) and from indicated planes acquired at 24 h post-treatment and after injection with $^{64}$Cu-DOTA-ECL1i. White arrows point to labeled organs. (FIG. 23B) Time activity curves of $^{64}$Cu-DOTA-ECL1i in heart and lungs 0-60 min, n=3/group from a subgroup described in FIG. 23C. *P<0.001 by unpaired, two-tailed t-test comparing lung PBS and LPS groups. (FIG. 23C) $^{64}$Cu-DOTA-ECL1i lung uptake acquired at indicated time post-treatment (PBS, n=5; LPS n=7 at 24 h, n=3 at 48 h, n=3 at 144 h). (FIG. 23D) Uptake in lung after delivery of low (n=3), intermediate (n=7) and high dose (n=3) LPS. The intermediate dose activity is the same data as shown in C for comparison. Data in FIG. 23B, FIG. 23C, FIG. 23D are the mean±SD. *P<0.001 compared to PBS in FIG. 23C and *P<0.001 and **P=0.006 compared to low dose LPS in FIG. 23D, by one-way ANOVA with Tukey's test FIG. 24A (FIG. 24B) Quantification of lung activity after the treatment described in A. Data are the mean±SD. *P<0.001 compared to LPS-treated WT mice injected with $^{64}$Cu-DOTA-ECL1i, by one-way ANOVA with Tukey's test.

(FIG. 26A) Photomicrograph of CCR2 immunostaining in lung tissue from non-COPD lung donors, and a subject with severe COPD demonstrating a high number of CCR2-expressing cells. Captured at 100× magnification; bar=100 μm; CCR2, red; DAPI, blue. (FIG. 26B) Quantification of CCR2 staining area relative to DAPI in lung sections from donor (n=11) and COPD (n=16) subjects, from photographs acquired at 200×. (FIG. 26C) Representative autoradiography of $^{64}$Cu-DOTA-ECL1i binding to lung tissues sections on glass slides. (FIG. 26D) Quantification of autoradiography of lung sections from subjects with COPD. The counts in each blocked sample were compared to those non-blocked tissues, which were set as 1.0, n=6. Bars in B and D describe the median value, and are significantly different between groups, *P=0.002 in B and D by the Mann-Whitney test for non-parametric data.

DETAILED DESCRIPTION OF THE INVENTION

Figure 1:
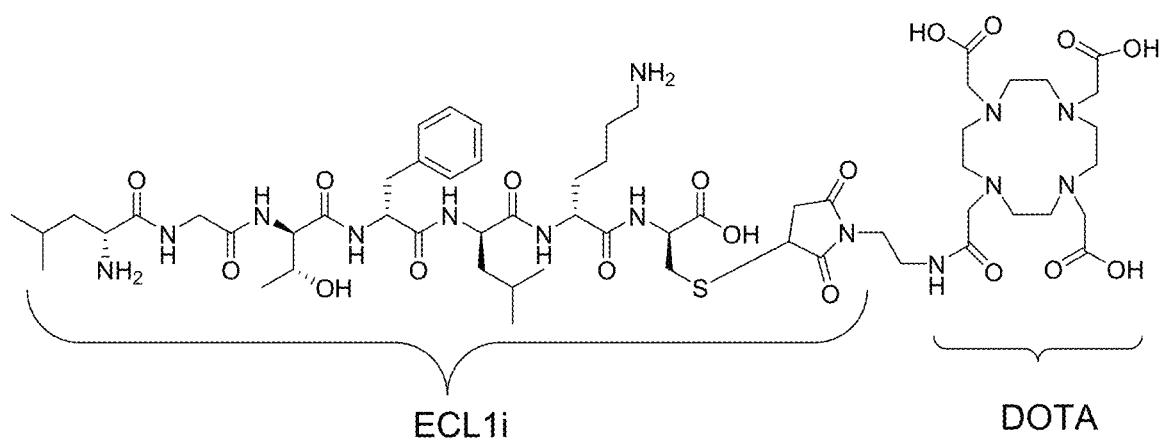
FIG. 1 is a structure of DOTA-ECL1i (synthetic methods are described in Examples 1, 2, and 3).

The present disclosure is based, at least in part, on the discovery that a CCR2 binding peptide adapted as a PET probe can detect CCR2 receptors or inflammation in a mouse model and human tissues.

As described herein, a $^{64}$Cu-radiolabeled ECL1i peptide radiotracer ($^{64}$Cu-DOTA-ECL1i) and ECL1i-conjugated gold nanoclusters doped with $^{64}$Cu ($^{64}$CuAuNCs-ECL1i) showed specific detection of CCR2. Due to its fast pharmacokinetics $^{64}$Cu-DOTA-ECL1i functioned efficiently for rapid and serial imaging of CCR2. The multivalent $^{64}$CuAuNCs-ECL1i with extended pharmacokinetics is favored for long-term CCR2 detection and potential targeted theranostics.

As described herein, the developed imaging agents (e.g., PET tracer of $^{64}$Cu-DOTA-ECL1i) have shown the specific and sensitive detection of CCR2 receptor up-regulated at inflammatory sites in multiple animal models. The biological characterization and confirmation of CCR2 receptor in these models show support for the robust PET imaging agent disclosed herein for clinical use.

As described herein, CCR2 binding peptide, ECL1i, adapted as a positron emission tomography (PET) radiotracer can be used to detect a 3.5-fold greater activity in the lungs of mice injured after intratracheal delivery of lipopolysaccharide compared to the saline control group (P<0.001).

As described herein, levels of CCR2$^+$ cells varied in human lung tissue among subjects with chronic obstructive lung disease (range 1.62 to 24.11 percent cells per tissue sample).

As described herein, the radiotracer $^{64}$Cu-DOTA-ECL1i can be used to detect inflammation in human lung tissue from subjects with COPD using autoradiography (specificity determined by non-radioactive blockade, 54.5%: P=0.002), suggesting clinical application if approved for in vivo human use.

Also described herein are detailed methods for mouse studies (see e.g., Example 4); hCCR2 binding assay (see e.g., Example 5); lung tissue binding (see e.g., Example 5); toxicology and dosimetry (see e.g., Example 6A); manufacturing and controls (CMC) and standard operating procedures (SOPs) for $^{64}$Cu-DOTA-ECL1i production (see e.g., Example 6B); and methods for phase 0 and early phase 1 clinical trials (see e.g., Example 6C).

Imaging Agent/CCR Molecular Probes

In these studies, the use of CCR2-specific molecular probes or imaging agents are reported.

As described herein, a novel imaging agent was developed through the conjugation of a novel targeting peptide for positron emission tomography (PET) imaging in mouse models of CCR2 associated diseases, disorders, and conditions (e.g., lung injury using lipopolysaccachride (LPS), transplant-mediated ischemia reperfusion injury, atherosclerosis, prostate cancer).

The presently disclosed work provides a powerful tool for the sensitive and specific detection of CCR2 to track inflammatory monocytes in various pathological conditions and lay the foundation for new approaches for the diagnosis and treatment of immune-mediated processes (e.g., ischemia reperfusion injury and rejection in transplant recipients) using imaging modalities (e.g., PET).

As described herein, an imaging agent can comprise a radiolabel, a CCR2 binding peptide, a nanoparticle, and/or a chelator. The imaging agent can further comprise a linker group. An imaging agent can be formulated to be detected by any method of imaging known in the art. For example, the imaging agent can be detected using a PET scanner (i.e., the imaging agent is a PET imaging agent or tracer). As another example, the imaging modality used to detect the imaging agent can comprise PET, SPECT, mass spectrometry, MRI, NMR, fluorescence spectroscopy, computed tomography (CT), ultrasound, or X-ray.

The present disclosure provides the first known imaging probe available for CCR2 detection. Currently, there are no known available methods for the non-invasive imaging of CCR2. To fill this gap, the present disclosure provides for CCR2 receptor imaging agents (e.g., a radiolabeled positron emission tomography (PET) tracer) have been developed based on the ECL1i peptide (DLeu-Gly-DThr-DPhe-DLeu-DLys-DCys).

Provided herein are positron emission tomography (PET) and single photon emission computed tomography (SPECT) imaging probes using a CCR2 binding peptide (e.g., the ECL1 (C) inverso peptide (LGTFLKC) to image the up-regulation of chemokine receptor CCR2 in both in vitro cell studies and a range of animal disease models. The peptide can be conjugated with macrocyclic chelator for radiolabeling with various radionuclides or grafted on a nanostructure with controlled physicochemical properties. The conjugation strategy and compositions of developed imaging probes have been optimized for enhanced binding affinity and improved in vivo pharmacokinetics.

PET imaging has been performed in animal disease models to non-invasively track the specific cell population expressing CCR2 receptor at site-of-interest. In other studies, fluorescent or other tags can be conjugated on the peptide to track the probe for non-radioactive studies.

For example, the present disclosure describes a $^{64}$Cu-DOTA-ECL1i tracer developed for PET imaging of CCR2 receptor up-regulation associated with inflammation in multiple models of disease including a murine lung transplant model, a murine lung lipopolysaccharide (LPS) injury model, an apolipoprotein E-deficient (ApoE$^{-/-}$) mouse atherosclerosis model, and a prostate cancer xenograft mouse model.

As described herein, the CCR2 imaging specificity and sensitivity have been well characterized in pre-clinical studies.

Lung Transplantation Model.

The CCR2 targeting specificity has been confirmed by using CCR2 knock-out (CCR2$^{-/-}$) mice in the lung transplantation model.

Specifically, strong PET signal was observed in the donor lung of wild type to wild type mouse lung transplantation model. In the wild type to CCR2$^{-/-}$ lung transplantation model, PET signal was only detected in the donor lung, not the recipient lung, which demonstrated the CCR2 targeting specificity of $^{64}$Cu-DOTA-ECL1i. The characterization of CCR2 receptor was confirmed using flow cytometry and immunohistochemistry. The CCR2 imaging specificity was also verified by performing a competitive receptor blocking study through the co-injection of $^{64}$Cu-DOTA-ECL1i and excess amount of ECL1i peptide (ECL1i vs. $^{64}$Cu-DOTA-ECL1i molar ratio=500:1) in the wild type to wild type mouse lung transplantation model. Quantitative PET data analysis showed significantly blocked signal at donor lung compared to uptake in the donor lung without the blocking agent, indicating the CCR2 specific tracer uptake.

LPS Injury Model.

The CCR2 targeting specificity has been confirmed by using CCR2 knock-out (CCR2$^{-/-}$) mice in the lung LPS injury model.

The imaging sensitivity of $^{64}$Cu-DOTA-ECL1i was characterized in the lung LPS injury model. Specifically, following the administration of LPS at low, intermediate and high dose level to generate different levels of injury, $^{64}$Cu-DOTA-ECL1i PET imaging was performed at 24 h post injury following the same imaging protocol. The PET signal intensities in the lungs correlated with the injury level, which demonstrated the sensitivity of this PET tracer detecting inflammation.

Atherosclerosis Model.

In mouse apoE$^{-/-}$ atherosclerosis model, the $^{64}$Cu-DOTA-ECL1i tracer clearly showed the detection of plaque at aortic arch and great potential to track the progression of disease.

Prostate Cancer Model.

In a mouse PC3 prostate cancer model, the $^{64}$Cu-DOTA-ECL1i tracer demonstrated sensitive and specific detection of tumor cells. Experiments are being performed to correlate the PET imaging data to the progression of tumors.

As such, the applicability of $^{64}$Cu-DOTA-ECL1i in detecting CCR2 has been demonstrated herein in multiple animal models of CCR2 associated diseases, disorders, and conditions. CCR2 is an interesting target for numerous diseases (e.g., atherosclerosis, metabolic disease (type II diabetes), cancer, multiple sclerosis, rheumatoid arthritis, pain, pulmonary fibrosis). The disclosed imaging agents can be useful for the evaluation of the treatment for CCR2 associated diseases, disorders, or conditions to optimize the treatment strategy and to improve the therapeutic efficacy.

The imaging agent, as described herein, can be a biocompatible imaging agent. As such, the imaging agent can be stored in or prepared in a buffer of a physiologically relevant pH. For example, the pH can be about 1 to 3 (e.g., for stomach); about 4 to 7 (e.g., for small intestine); about 7-8.5 (e.g., for large intestine); about 7.4 (e.g., for blood pH); about 7.35 (e.g., for CSF); or about 5 to 6 (e.g., for urine pH). As another example, the pH can be about 1; about 1.5; about 2; about 2.5; about 3; about 3.5; about 4; about 4.5; about 5; about 5.5; about 6; about 6.5; about 6.6; about 6.7; about 6.8; about 6.9; about 7; about 7.1; about 7.2; about 7.3; about 7.4; about 7.5; about 8; or about 8.5.

CCR2 Binding Peptide

As described herein, the imaging agent comprises a CCR2 binding peptide. The CCR2 binding peptide can be any peptide with CCR2 activity. For example, the CCR2 binding peptide can be a CCR2 non-competitive antagonist peptide. As another example, the CCR2 binding peptide can be a cyclized CCR2 binding peptide.

As described herein, monocyte chemo-attractant protein chemokines are secreted by a wide variety of cell types under a range of inflammatory conditions such as atherosclerosis, neurodegenerative disease, and various forms of cancer (among various other diseases and conditions). One of the most prominent chemokines is monocyte chemoattractant protein-1 (MCP-1), now called CCL2, which significantly regulates migration and infiltration of monocytes to the site of inflammation, predominantly through CC-chemokine receptor 2 (CCR2).

CCR2 binding peptides can be any CCR2 peptide known, such as those described in US Pat Pub No. 2015/0011477, incorporated herein by reference in its entirety. The imaging agent as described herein comprises a CCR2 binding peptide. For example, the CCR2 binding peptide can comprise an ECL1i peptide, as described in US Pat Pub No. 2015/0011477, incorporated herein by reference. Because CCR2$^+$ cells migrate in response to CCL2, CCR2 can be a surrogate marker for CCR2. As such, CCL2 and CCR2 can be used interchangeably.

For example, the binding peptide can comprise ECL1i. An ECL1i peptide can be of the sequence DLeu-Gly-DThr-DPhe-DLeu-DLys-DCys (SEQ ID NO: 3). As another example, a CCR2 binding peptide can be a peptide comprising the following amino acid sequence Thr-Phe-Leu-Lys or Thr-Phe-Leu-Lys-Cys, useful as a CCR2 non-competitive antagonist peptide. As another example, the ECL1i peptide can be a cyclized ECL1i peptide (e.g., Cyclo-(Orn-LGT-FLK)).

Among all the peptides tested, the heptapeptide LGT-FLKC, named ECL1 (C) inverso, presented interesting properties as a CCR2 non-competitive antagonist peptide. This peptide corresponds to an inverted sequence in the third transmembrane domain of CCR2, more precisely in the juxtamembranous and N-terminal region of the third transmembrane domain. In some embodiments, all or part of the amino acids are in a D configuration.

As another example, as described in US Pat Pub No. 2015/0011477 (incorporated by reference, herein), the CCR2 binding peptide can be:

TABLE 5

CCR2 binding peptides

| SEQ ID NO: | Description | Peptide Sequence | Comments |
|---|---|---|---|
| 1 | | Thr Phe Leu Lys Cys | |
| 2 | | Xaa Thr Phe Leu Lys Cys Xaa | Xaa in position 1 is absent, is glycine or represents an amino acid sequence selected from the group consisting of LG, YLG, and HYLG; "Xaa in |

TABLE 5-continued

CCR2 binding peptides

| SEQ ID NO: | Description | Peptide Sequence | Comments |
|---|---|---|---|
| | | | position 7" independently is absent, is methionine, or represents an amino acid sequence selected from the group consisting of MA, MAN, MANG, MANGF, MANGFV, MANGFVW, MANGFVWE, and MANGFVWEN |
| 3 | ECL1 (C) inverso; ECL1i | Leu Gly Thr Phe Leu Lys Cys | |
| 4 | | His Tyr Leu Gly Thr Phe Leu Lys Cys Met Ala | |
| 5 | | Leu Gly Thr Phe Leu Lys Cys Met Ala | |
| 6 | | His Tyr Leu Gly Thr Phe Leu Lys Cys | |
| 7 | | Gly Thr Phe Leu Lys Cys Met Ala Asn Gly Phe | |
| 8 | | Thr Phe Leu Lys Cys Met Ala Asn Gly Phe Val | |
| 9 | | His Tyr Leu Gly Thr Phe Leu Lys Cys Met Ala Asn Gly Phe Val Trp | |
| 10 | ECL1 (C) | Cys Lys Leu Phe Thr Gly Leu | |
| 11 | ECL2 (N) | Leu Phe Thr Lys Cys | |
| 12 | ECL2 (N) inverso | Cys Lys Thr Phe Leu | |
| 13 | ECL3 (C) | His Thr Leu Met Arg Asn Leu | |
| 14 | ECL3 (C) inverso | Leu Asn Arg Met Leu Thr His | |
| 15 | ECL3 (N) | Leu Asn Thr Phe Gln Glu Phe | |
| 16 | ECL3 (N) inverso | Phe Glu Gln Phe Thr Asn Leu | |
| 17 | | Thr Phe Leu Lys | |
| 18 | | Xaa Thr Phe Leu Lys Xaa | Xaa in position 1 is absent, is glycine or represents an amino acid sequence selected from the group consisting of AG, LG, YLG and HYLG; "Xaa in position 6" independently is absent or is alanine |
| 19 | | Leu Gly Thr Phe Leu Lys | |
| 20 | | Ala Gly Thr Phe Leu Lys Cys | |
| 21 | | Leu Gly Thr Phe Leu Lys Ala | |

TABLE 5-continued

CCR2 binding peptides

| SEQ ID NO: | Description | Peptide Sequence | Comments |
|---|---|---|---|
| 22 | | Gly Thr Phe Leu Lys | |
| 23 | | Ala Gly Thr Phe Leu Lys Ala | |
| 24 | | Met Ala Asn Gly | |
| 25 | | Met Ala Asn Gly Phe | |
| 26 | | Met Ala Asn Gly Phe Val | |
| 27 | | Met Ala Asn Gly Phe Val Trp | |
| 28 | | Met Ala Asn Gly Phe Val Trp Glu | |
| 29 | | Met Ala Asn Gly Phe Val Trp Glu Asn | |
| 30 | | His Tyr Leu Gly | |

The CCR2 binding peptide as described herein can comprise an amino acid length of about 4 amino acids to about 200 amino acids or about 4 amino acids to about 50 amino acids. For example, the CCR2 biding peptide can comprise an amino acid length of no more than 4 amino acids; 5 amino acids; 6 amino acids; 7 amino acids; 8 amino acids; 9 amino acids; 10 amino acids; 11 amino acids; 12 amino acids; 13 amino acids; 14 amino acids; 15 amino acids; 16 amino acids; 17 amino acids; 18 amino acids; 19 amino acids; 20 amino acids; 21 amino acids; 22 amino acids; 23 amino acids; 24 amino acids; 25 amino acids; 26 amino acids; 27 amino acids; 28 amino acids; 29 amino acids; 30 amino acids; 31 amino acids; 32 amino acids; 33 amino acids; 34 amino acids; 35 amino acids; 36 amino acids; 37 amino acids; 38 amino acids; 39 amino acids; 40 amino acids; 41 amino acids; 42 amino acids; 43 amino acids; 44 amino acids; 45 amino acids; 46 amino acids; 47 amino acids; 48 amino acids; 49 amino acids; 50 amino acids; 51 amino acids; 52 amino acids; 53 amino acids; 54 amino acids; 55 amino acids; 56 amino acids; 57 amino acids; 58 amino acids; 59 amino acids; 60 amino acids; 61 amino acids; 62 amino acids; 63 amino acids; 64 amino acids; 65 amino acids; 66 amino acids; 67 amino acids; 68 amino acids; 69 amino acids; 70 amino acids; 71 amino acids; 72 amino acids; 73 amino acids; 74 amino acids; 75 amino acids; 76 amino acids; 77 amino acids; 78 amino acids; 79 amino acids; 80 amino acids; 81 amino acids; 82 amino acids; 83 amino acids; 84 amino acids; 85 amino acids; 86 amino acids; 87 amino acids; 88 amino acids; 89 amino acids; 90 amino acids; 91 amino acids; 92 amino acids; 93 amino acids; 94 amino acids; 95 amino acids; 96 amino acids; 97 amino acids; 98 amino acids; 99 amino acids; 100 amino acids; 101 amino acids; 102 amino acids; 103 amino acids; 104 amino acids; 105 amino acids; 106 amino acids; 107 amino acids; 108 amino acids; 109 amino acids; 110 amino acids; 111 amino acids; 112 amino acids; 113 amino acids; 114 amino acids; 115 amino acids; 116 amino acids; 117 amino acids; 118 amino acids; 119 amino acids; 120 amino acids; 121 amino acids; 122 amino acids; 123 amino acids; 124 amino acids; 125 amino acids; 126 amino acids; 127 amino acids; 128 amino acids; 129 amino acids; 130 amino acids; 131 amino acids; 132 amino acids; 133 amino acids; 134 amino acids; 135 amino acids; 136 amino acids; 137 amino acids; 138 amino acids; 139 amino acids; 140 amino acids; 141 amino acids; 142 amino acids; 143 amino acids; 144 amino acids; 145 amino acids; 146 amino acids; 147 amino acids; 148 amino acids; 149 amino acids; 150 amino acids; 151 amino acids; 152 amino acids; 153 amino acids; 154 amino acids; 155 amino acids; 156 amino acids; 157 amino acids; 158 amino acids; 159 amino acids; 160 amino acids; 161 amino acids; 162 amino acids; 163 amino acids; 164 amino acids; 165 amino acids; 166 amino acids; 167 amino acids; 168 amino acids; 169 amino acids; 170 amino acids; 171 amino acids; 172 amino acids; 173 amino acids; 174 amino acids; 175 amino acids; 176 amino acids; 177 amino acids; 178 amino acids; 179 amino acids; 180 amino acids; 181 amino acids; 182 amino acids; 183 amino acids; 184 amino acids; 185 amino acids; 186 amino acids; 187 amino acids; 188 amino acids; 189 amino acids; 190 amino acids; 191 amino acids; 192 amino acids; 193 amino acids; 194 amino acids; 195 amino acids; 196 amino acids; 197 amino acids; 198 amino acids; 199 amino acids; or 200 amino acids. Recitation of each of these discrete values is understood to include ranges between each value. Recitation of each of a range is understood to include discrete values within the range.

Radiolabel

The imaging agent, as described herein, comprises a radiolabel (also known as a radionuclide). Radiolabeling processes are well known and also described in Example 1; see e.g. Fani et al. *Theranostics* 2012; 2(5):481-501. doi: 10.7150/thno.4024. Except as otherwise noted herein, therefore, the process of the present disclosure can be carried out in accordance with such processes.

One embodiment of the present disclosure provides for a radiolabeled peptide. According to another embodiment, the radiolabeled compound can be an imaging agent.

References herein to "radiolabeled" include a compound where one or more atoms are replaced or substituted by an atom having an atomic mass or mass number different from the atomic mass or mass number typically found in nature (i.e., naturally occurring). One non-limiting exception is $^{19}$F, which allows detection of a molecule which contains this element without enrichment to a higher degree than what is naturally occurring. Compounds carrying the substituent $^{19}$F may thus also be referred to as "labelled" or the like. The term radiolabeled may be interchangeably used with "isotopically-labelled", "labelled", "isotopic tracer group", "isotopic marker", "isotopic label", "detectable isotope", or "radioligand".

In one embodiment, the compound comprises one or more radiolabeled groups.

Examples of suitable, non-limiting radiolabel groups can include: $^2$H (D or deuterium), $^3$H (T or tritium), $^{11}$C, $^{13}$C, $^{14}$C, $^{64}$Cu, $^{67}$Cu, $^{177}$Lu, $^{13}$N, $^{15}$N, $^{15}$O, $^{17}$O, $^{18}$O, $^{18}$F, $^{89}$Sr, $^{35}$S, $^{153}$Sm, $^{36}$Cl, $^{82}$Br, $^{75}$Br, $^{76}$Br, $^{77}$Br, $^{123}$I, $^{124}$I, $^{125}$I, $^{131}$I, $^{111}$In, $^{67}$Ga, $^{68}$Ga, $^{177}$Lu, $^{186}$Re, $^{188}$Re, $^{201}$Tl $^{99m}$Tc, $^{90}$Y, or $^{89}$Zr. It is to be understood that an isotopically labeled compound needs only to be enriched with a detectable isotope to, or above, the degree which allows detection with a technique suitable for the particular application, e.g., in a detectable compound labeled with $^{11}$C, the carbon-atom of the labeled group of the labeled compound may be constituted by $^{12}$C or other carbon-isotopes in a fraction of the molecules. The radionuclide that is incorporated in the radiolabeled compounds will depend on the specific application of that radiolabeled compound. For example, "heavy" isotope-labeled compounds (e.g., compounds containing deuterons/heavy hydrogen, heavy nitrogen, heavy oxygen, heavy carbon) can be useful for mass spectrometric and NMR based studies. As another example, for in vitro labelling or in competition assays, compounds that incorporate $^3$H, $^{14}$C, or $^{125}$I can be useful. For in vivo imaging applications $^{11}$C, $^{13}$C, $^{18}$F, $^{19}$F, $^{120}$I, $^{123}$I, $^{131}$I, $^{75}$Br, or $^{76}$Br can generally be useful. In one embodiment, the radiolabel is $^{64}$Cu.

As another example, the imaging agent comprising a radiolabel can comprise Oxygen-15 water, Nitrogen-13 ammonia, [$^{82}$Rb] Rubidium-82 chloride, [$^{11}$C], [$^{11}$C] 25B-NBOMe, [$^{18}$F] Altanserin, [$^{11}$C] Carfentanil, [$^{11}$C] DASB, [$^{11}$C] DTBZ, [$^{18}$F]Fluoropropyl-DTBZ, [$^{11}$C] ME@HAPTHI, [$^{18}$F] Fallypride, [$^{18}$F] Florbetaben, [$^{18}$F] Flubatine, [$^{18}$F] Fluspidine, [$^{18}$F] Florbetapir, [$^{18}$F] or [$^{11}$C] Flumazenil, [$^{18}$F] Flutemetamol, [$^{18}$F] Fluorodopa, [$^{18}$F] Desmethoxyfallypride, [$^{18}$F] Mefway, [$^{18}$F] MPPF, [$^{18}$F] Nifene, Pittsburgh compound B, [$^{11}$C] Raclopride, [$^{18}$F] Setoperone, [$^{18}$F] or [$^{11}$C] N-Methylspiperone, [$^{11}$C] Verapamil, [$^{11}$C] Martinostat, Fludeoxyglucose ($^{18}$F)(FDG)-glucose analogue, [$^{11}$C] Acetate, [$^{11}$C] Methionine, [$^{11}$C] Choline, [$^{18}$F] Fluciclovine, [$^{18}$F] Fluorocholine, [$^{18}$F] FET, [$^{18}$F] FMISO, [$^{18}$F] 3'-fluoro-3'-deoxythymidine, [$^{68}$Ga] DOTA-pseudopeptides, [$^{68}$Ga] PSMA, or [$^{18}$F] Fluorodeoxysorbitol (FDS).

Chelator

As described herein, radionuclides can be chelated by any method known in the art.

Processes of chelating a radioligand are well known; see e.g. Anderson et al., Cancer Biother Radiopharm. 2009 August; 24(4): 379-393; Stockholf et al., Pharmaceuticals (Basel). 2014 April; 7(4): 392-418. Except as otherwise noted herein, therefore, the process of the present disclosure can be carried out in accordance with such processes. For example, chelators for a radiolabel (e.g., $^{64}$Cu) can be any of those known in the art (e.g., a macrocyclic chelator). As another example, the chelator can comprise NHS-MAG$_3$, MAG$_3$, DTPA, 3p-C-NE3TA, 3p-C-NOTA, 3p-C-DE4TA, ATSM, tetraazamacrocyclic ligands (e.g., DOTA (1,4,7,10-tetraazacyclododecane-1,4,7,10-tetraacetic acid), DOTA-NHS, pSCN-Bn-DOTA, pNH$_2$-Bn-DOTA, TETA (1,4,8,11-tetraazacyclotetradecane-1,4,8,11-tetraacetic acid, TETA-octreotide (OC)), hexaazamacrobicyclic cage-type ligands (e.g., Sarcophogine chelators), cross-bridged tetraamine ligands (e.g., CB-TE2A (4,11-bis(carboxymethyl)-1,4,8,11-tetraazabicyclo[6.6.2]hexadecane)), 6-Hydrazinopridine-3-carboxylic acid (Hynic), or NHS-Hynic. As another example, a radiolabelled (e.g., $^{64}$Cu) chelator can be 2,2', 2''-(10-(2-((2-(2,5-dioxo-2,5-dihydro-1H-pyrrol-1-yl)ethyl) amino)-2-oxoethyl)-1,4,7,10-tetraazacyclododecane-1,4,7-triyl)triacetic acid (Maleimido-mono-amide-DOTA).

Nanoparticle

As described herein, a radiolabel can be doped in or on a nanoparticle, or a radiolabel can be conjugated to a nanoparticle.

The imaging agent, as described herein can comprise any nanoparticle known in the art suitable for use as an imaging agent. Nanoparticles for use in molecular probes and imaging agents are well known; see e.g., Chen et al., Molecular Imaging Probes for Cancer Research, 2012.

Labeling of nanoparticles are well known; see e.g., Yongjian Liu, Michael J Welch, Nanoparticles labeled with positron emission nuclides: advantages, methods, and applications, Bioconjugate Chemistry, 2012, 23, 671-682; Stockholf et al., Pharmaceuticals (Basel). 2014 April; 7(4): 392-418. Except as otherwise noted herein, therefore, the process of the present disclosure can be carried out in accordance with such processes.

For example, a nanoparticle can be a nanocluster or any other type of nanostructures including organic, inorganic, or lipid nanostructures.

As another example, the nanoparticle can comprise Au or Cu. As another example, the nanoparticle can comprise iron oxide, gold, gold nanoclusters (AuNC), gold nanorods (AuNR), copper (Cu), quantum dots, carbon nanotubes, carbon nanohorn, gadolinium (Gd), dendrimers, dendrons, polyelectrolyte complex (PEC) nanoparticles, calcium phosphate nanoparticles, perfluorocarbon nanoparticles (PFCNPs), or lipid-based nanoparticles, such as liposomes and micelles.

Linker

Described herein are linkers used to attach peptides to a portion of an imaging agent (e.g., a core, a nanoparticle, a radiolabel, a chelator, another peptide). A linker can be any composition used for conjugation, for example to a nanoparticle or chelator.

A linker group can be any linker group suitable for use in an imaging agent. Linker groups for imaging agents (e.g., molecular probes) are well known (see e.g., Werengowska-Ciećwierz et al., Advances in Condensed Matter Physics, Vol. 2015 (2015); Chen et al., Curr Top Med Chem. 2010; 10(12): 1227-1236). Except as otherwise noted herein, therefore, the processes of the present disclosure can be carried out in accordance with such processes.

For example, the linker can conjugate a nanoparticle to a CCR2 biding peptide. For example, the CCR2 binding peptide can be covalently attached to the linker. For example, the linker can comprise a poly(ethylene glycol) (PEG) derivative. As another example, the linker can comprise PEG, TA-PEG-Maleimide, TA-PEG-OMe, or TA-PEG. As another example, a linker can comprise an isothiocyanate group, a carboxylic acid or carboxylate groups, a dendrimer, a dendron, Fmoc-protected-2,3-diaminopropanoic acid, ascorbic acid, a silane linker, minopropyltrimethoxysilane (APTMS), or dopamine. Other covalent coupling methods can use employ the use of 2 thiol groups, 2 primary amines, a carboxylic acid and primary amine, maleimide and thiol, hydrazide and aldehyde, or a primary amine and aldehyde. For example, the linker can be an amide, a thioether, a disulfide, an acetyl-hydrazone group, a polycyclic group, a click chemistry (CC) group (e.g., cycloadditions, for example, Huisgen catalytic cycloaddition; nucleophilic substitution chemistry, for example, ring opening of heterocyclic electrophiles; carbonyl chemistry of the "nonaldol" type, for example, formation of ureas, thioureas, and hydrazones; additions to carbon-carbon multiple bonds, for example, epoxidation and dihydroxylation); or a physical or chemical bond.

Detecting CCR2/CCL2 (MCP-1) Associated Disease, Disorders, or Conditions

As described herein, the present disclosure provides for methods of detecting or imaging CCR2 receptors or evaluating or monitoring a CCR2 associated disease, disorder, or condition. CCR2 receptors are upregulated in CCR2 associated disease, disorders, or conditions.

CCR2/CCL2

Because of the relationship between CCL2 and CCR2, a CCR2 associated disease can also be a disease associated with CCL2 (MCP-1).

Chemokines, or chemotactic cytokines, are small heparin-binding proteins that constitute a large family of peptides (60-100 amino acids) structurally related to cytokines, whose main function is to regulate cell trafficking, particularly that of immune cells, and thus are of relevance to this BRTC application.

Chemokines can be classified into four subfamilies on the basis of the number and location of the cysteine residues at the N-terminus of the molecule and are named CXC, CC, CX3C, and C. They initiate their cellular effects via interaction with a specific G protein-coupled receptor. Monocyte chemo-attractant protein chemokines are secreted by a wide variety of cell types under a range of inflammatory conditions such as atherosclerosis, neurodegenerative disease and various forms of cancer. One of the most prominent of these is monocyte chemoattractant protein-1 (MCP-1), now called CCL2, which significantly regulates migration and infiltration of monocytes to the site of inflammation, predominantly through CC-chemokine receptor 2 (CCR2). In the case of the monocyte subsets mentioned above CD16-/Ly6Chi pro-inflammatory monocytes exhibit high CCR2 expression, whereas the CD16+/Ly6Clo low-inflammatory monocytes do not. This interplay and its impact on monocyte trafficking and tissue inflammation really highlight the importance of CCR2 imaging to identify the critical pro-inflammatory monocyte subset as well as potentially track its migration from hematopoietic sites to sites of inflammation in both pre-clinical and clinical research.

CCR2 Associated Diseases, Disorders, or Conditions

A CCR2 associated disease can be any disease, disorder, or condition in which CCR2 is involved; the disease disorder, or condition is associated with CCR2; or a CCR2 mediated syndrome. CCR2 is implicated in atherosclerosis, prostate cancer, lung transplantation, and lung injury, for example. CCR2 associated diseases can be an inflammatory diseases or cancer. For example, a CCR2 associated disease can be an inflammatory disease, metabolic disease (e.g., type II diabetes), necrosis, atherosclerosis, cancer (e.g., prostate cancer), multiple sclerosis, atheroma, monocytic leukemia, kidney diseases (e.g., glomerularnephritis), Hamman-Rich syndrome, endometriosis, rheumatoid arthritis, bronchiolitis, asthma, systemic lupus erythematosus, inflammatory bowel diseases (e.g., colitis), alveolitis, restinosis, brain trauma, psoriasis, idiopathic pulmonary fibrosis, transplant arteriosclerosis, vascular permeability and attraction of immune cells during metastasis, a number of different neurological disorders, autoimmune disease, obesity, multiple sclerosis, rheumatoid arthritis, pain, or pulmonary fibrosis.

As another example, the CCR2 associated disease, disorder, or condition can be an ophthalmic disorder, uveitis, atherosclerosis, abdominal aortic aneurysm, rheumatoid arthritis, psoriasis, psoriatic arthritis, atopic dermatitis, multiple sclerosis, Crohn's Disease, ulcerative colitis, nephritis, organ allograft rejection, fibroid lung, renal insufficiency, diabetes and diabetic complications, diabetic nephropathy, diabetic retinopathy, diabetic retinitis, diabetic microangiopathy, tuberculosis, chronic obstructive pulmonary disease, sarcoidosis, invasive staphyloccocia, inflammation after cataract surgery, allergic rhinitis, acute or chronic sinusitis allergic conjunctivitis, chronic urticaria, asthma, allergic asthma, periodontal diseases, periodontis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, head and neck, lung, prostate, or stomach.

As another example, the CCR2 mediated syndrome, disorder, or disease can be age-related macular degeneration or retinal degeneration. As another example, the CCR2 mediated syndrome, disorder, or disease can be a cardiovascular disease, especially ischemia of lower members or of the heart, or atherogenesis. As another example, the CCR2 mediated syndrome, disorder, or disease can be pain, in particular peripheral pain, such as pain from the sciatic nerve. As another example, the CCR2 mediated syndrome, disorder, or disease can be acute and chronic lung diseases—acute lung injury, primary graft dysfunction (PGD) (a reperfusion injury after transplant), COPD, asthma, pulmonary fibrosis, bronchiolitis obliterans syndrome, and fungal pneumonia.

CCL2 is also associated with the neuroinflammatory processes that take place in various diseases of the central nervous system (CNS), which are characterized by neuronal degeneration. CCL2 expression in glial cells is increased in epilepsy, brain ischemia Alzheimer's disease experimental autoimmune encephalomyelitis (EAE), and traumatic brain injury.

As another example, CCR2 has been shown to be associated with idiopathic anterior uveitis; HIV-1; Cd3zeta deficiency; cytomegalovirus retinitis; rhinoscleroma; secondary progressive multiple sclerosis; lipid pneumonia; rheumatoid arthritis; or macular degeneration, age-related, 1.

As another example, CCL2 has been shown to be associated with neural tube defects; vangl1-related neural tube defect; HIV-1; *Mycobacterium tuberculosis*, susceptibility to *Mycobacterium tuberculosis*, protection against, included; proliferative glomerulonephritis; arthritis; rheumatoid arthritis; herpes simplex virus keratitis; anthracosis; crescentic glomerulonephritis; peritonitis; acute cystitis; arteriosclerosis; xanthogranulomatous pyelonephritis; mast-cell leukemia; psoriasis; trypanosomiasis; retinal vasculitis; diabetic macular edema; mesangial proliferative glomerulonephritis; Chagas disease; demyelinating disease; renal fibrosis; cerebral aneurysms; denture stomatitis; Kawasaki disease; verruciform xanthoma of skin; interstitial lung disease; severe acute respiratory syndrome; diabetic angiopathy; Erdheim-Chester disease; pulmonary alveolar proteinosis; uveitis; extrapulmonary tuberculosis; encephalitis; pneumonia; endometriosis; carotid artery disease; pneumoconiosis; retinal vein occlusion; abdominal aortic aneurysm; viral meningitis; glomerulonephritis; idiopathic interstitial pneumonia; nephrosclerosis; acute proliferative glomerulonephritis; viral encephalitis; pulmonary sarcoidosis; postthrombotic syndrome; vascular disease; alcoholic hepatitis; papillary conjunctivitis; hyperhomocysteinemia; scleritis; radiculopathy; pulmonary fibrosis; lipoid nephrosis; pleural tuberculosis; autoinflammation, lipodystrophy, and dermatosis syndrome; pleurisy; complex regional pain syndrome; pyelonephritis; endocervicitis; leptospirosis; microvascular complications of diabetes 1; dengue shock syndrome; peripheral artery disease; chorioamnionitis; silicosis; pelvic inflammatory disease; vitreoretinopathy, neovascular inflammatory disease; purulent labyrinthitis; stachybotrys chartarum; transient cerebral ischemia; neuritis; keratitis; tuberculous meningitis; nonspecific interstitial pneumonia; limb ischemia; secondary progressive multiple sclerosis; retinal vascular occlusion; Israeli tick typhus; bacteriuria; pulmonary fibrosis, idiopathic; stromal keratitis; bone cancer; sarcoidosis 1; malaria; ureteral disease; coronary artery aneurysm; lung disease; macular holes; urinary tract obstruction; extrinsic cardiomyopathy; periodontitis; systemic lupus erythematosus; vasculitis; ariboflavinosis; eye disease; meningitis; artery disease; cystitis; central nervous system disease; macular degeneration, age-related, 1; obesity; multiple sclerosis, disease progression, modifier of; diabetes mellitus, noninsulin-dependent; urinary system disease; endometrial stromal sarcoma; myocardial infarction; degeneration of macula and posterior pole; overnutrition; respiratory system disease; acquired metabolic disease; or bone inflammation disease.

CCR2 Associated Lung Disease

Lung diseases are often characterized by the nature of immune or inflammatory cells that are found within the tissues and airways. Chemokines guide the migration and function of inflammatory cells harboring their cognate receptor. In the lung, the chemokine CCL2 (monocyte chemoattractant protein-1, MCP-1), is frequently elevated in acute and chronic lung disease. CCL2 is the major ligand for the chemokine receptor CCR2, which is found largely on immune cells and notably on monocytes, dendritic cells (DCs), and T cells. As such, the imaging agent, as described herein can be used to image CCR2 in the lung to guide diagnosis and therapy.

As described herein, CCL2/CCR2 is elevated in lung disease. The CCL2/CCR2 axis is demonstrated to be active in acute and chronic lung diseases. CCR2 function is supported by deletion or antagonism in related mouse models. Diseases include those for which specific therapies are currently limited:

Acute Lung Injury.

Excessive recruitment of CCR2-dependent leukocytes impacts the pathogenesis of acute lung injury in human ARDS and mouse models, shaping the magnitude and duration of disease. Endotoxin (LPS) triggers CCR2-depedent migration of monocytes to the lung when administered intratracheally and also influences subsequent neutrophil recruitment in lung.

PGD.

Reperfusion injury immediately following lung transplant, known as primary graft dysfunction (PGD), is marked by elevated CCL2 levels in BAL fluid, while clinical improvement occurs as CCL2 levels fall. It was observed that CCR2 is required for mobilization of $CD11b^+$ $Ly6C^{hi}$ monocytes and accumulation into lung allographs in a mouse lung transplant model of PGD.

COPD.

Human studies of CCL2/CCR2 in COPD show increased levels of CCL2 in the sputum, BAL fluid and lungs (including ex-smokers) and expression of CCR2 on leukocytes and epithelia. It was recently reported that increased CCR2 was observed on interstitial monocytes from COPD lung tissue.

Asthma.

In human subjects with asthma studied by segmental allergy bronchoprovocation, CCL2 and CCR2 were increased in BAL. Blocking or genetic deletion of CCL2/CCR2 in mouse models of airway allergen sensitization prevents monocyte and dendritic cell migration and allergic responses.

Pulmonary Fibrosis and Others.

Human and mouse studies have also implicated the CCL2/CCR2 axis in the pathogenesis of pulmonary fibrosis, bronchiolitis obliterans syndrome, and fungal pneumonia.

Ischemia-Reperfusion Injury.

Ischemia reperfusion injury-mediated primary graft dysfunction substantially hampers short- and long-term outcomes after lung transplantation. This condition continues to be diagnosed based on oxygen exchange parameters as well as radiological appearance, and therapeutic strategies are mostly supportive in nature. Identifying patients who may benefit from targeted therapy would therefore be highly desirable.

Recruitment of innate immune cells to lungs shortly after reperfusion plays a key role in mediating tissue injury. It is reported herein that in addition to their well-recognized role in promoting acute injury, neutrophils can enhance adaptive immune responses after pulmonary transplantation. Interestingly, it has recently been demonstrated that monocytes facilitate the extravasation of neutrophils into reperfused lungs. It thus seems that for lung graft dysfunction, monocytes play a critical role in orchestrating tissue injury. These observations may be more generalizable as $CCR2^+$ monocytes promote the transendothelial migration of neutrophils in murine models of arthritis. Mouse monocytes are heterogeneous with $CD11b^+Ly6C^{high}CCR2^{high}$ monocytes considered to be an inflammatory subset. Experiments using CCR2-deficient mice have demonstrated that CCR2 signaling contributes to myocardial, renal and cerebral ischemia reperfusion injury. Attenuation of injury was associated with reductions of monocytic and neutrophilic infiltration into the affected tissues.

Here, it has been shown that CCR2 expression in murine lung transplant recipients promotes monocyte infiltration into pulmonary grafts and mediates graft dysfunction. The development of the new positron emission tomography imaging agents using a CCR2 binding peptide ECL1i that can be used to monitor inflammatory responses after organ transplantation has been shown herein. Both $^{64}$Cu-radiolabeled ECL1i peptide radiotracer ($^{64}$Cu-DOTA-ECL1i) and ECL1i-conjugated gold nanoclusters doped with $^{64}$Cu ($^{64}$CuAuNCs-ECL1i) showed specific detection of CCR2, which is up-regulated during ischemia-reperfusion injury after lung transplantation. Due to its fast pharmacokinetics $^{64}$Cu-DOTA-ECL1i functioned efficiently for rapid and serial imaging of CCR2. The multivalent $^{64}$CuAuNCs-ECL1i with extended pharmacokinetics is favored for long-term CCR2 detection and potential targeted theranostics. This imaging can be applicable for diagnostic and therapeutic purposes for a wide variety of immune-mediated diseases.

Lung Injury.

The imaging sensitivity of $^{64}$Cu-DOTA-ECL1i was characterized in the lung LPS injury model. Specifically, following the intratracheal administration of LPS at low, intermediate and high dose levels to create different levels of injury and inflammation in the lungs, $^{64}$Cu-DOTA-ECL1i PET imaging was performed at 24 h post injury following the same imaging protocol. PET images showed strong signals in all the inflammatory lungs. The quantitative uptake analysis of the lungs correlated with the LPS dose levels, which demonstrated the sensitivity of this PET tracer detecting inflammation.

Atherosclerosis.

Atherosclerosis is a chronic, inflammatory disease, which is the underlying basis for cardiovascular disease. In the mouse apoE$^{-/-}$ atherosclerosis model, $^{64}$Cu-DOTA-ECL1i PET image clearly showed the specific uptake at aortic arch where the atherosclerotic plaque was located. Longitudinal studies using this PET tracer to track the progression of plaque have been performed.

CCR2 Antagonists

The CCR2 antagonists, as described herein can be any CCR2 antagonist known in the art (see e.g., Struthers M, Pasternak A. CCR2 antagonists. Curr Top Med Chem. 2010; 10(13):1278-98).

Several CCR2 antagonists (see e.g., Example 2 and 3) including small molecules and antibodies have been used as inhibitors in various inflammatory diseases, both experimentally and in clinical trials. However, clinical trials have yielded equivocal or negative results. This may be due to recruitment of anti-inflammatory monocyte populations or other chemokine receptors contributing to inflammation. Moreover, inadequate dosing or duration of therapy due to concerns for toxicity or impedance of the essential role of CCR2 for immune surveillance may cloud the benefit of antagonists. It would therefore be desirable to devise a non-invasive CCR2 imaging technique, which is not only able to monitor the degree of receptor occupancy to aid in dose selection, but also to determine the therapeutic response in real time.

For example, a CCR2 antagonist can be NCT01215279; BMS-741672; BMS22; RS504393 (Tocris); BMS CCR2 28; CCX140-B; sc-202525; ucb-102405; benzimidazoles; SB-380732; AZD-6942; 3-aminopyrrolidines; INCB-003284; PF-6309; PF-04136309; PF-04634817; cenicriviroc; AZD2423; or CCR2 antibodies. As another example, the CCR2 antagonists can be an antagonist selected from the compounds below.

| Company | Compound |
|---|---|
| Roche/Iconix | 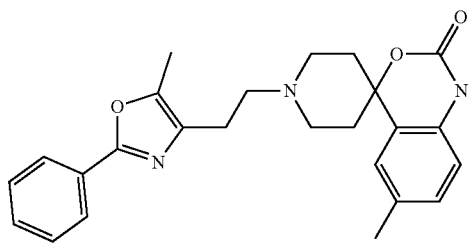 |
| | RS-504393 |
| Millennium/Pfizer | 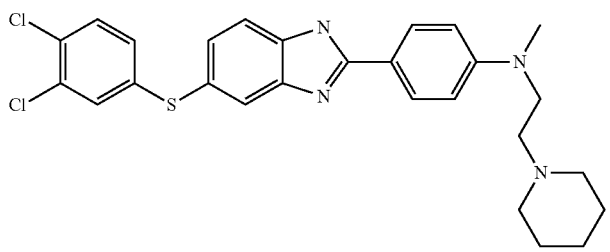 |
| | Benzimidazoles |
| SmithKline | 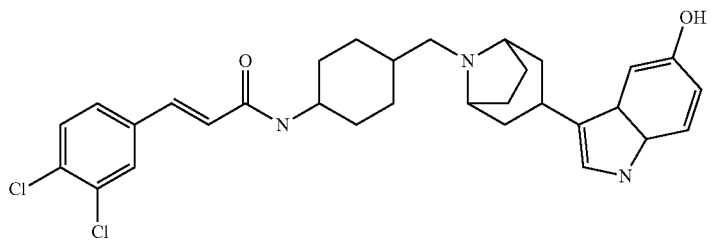 |
| | SB-380732 |

-continued
| Company | Compound |
|---|---|
| AstraZeneca | AZD-6942 |
| Merck | 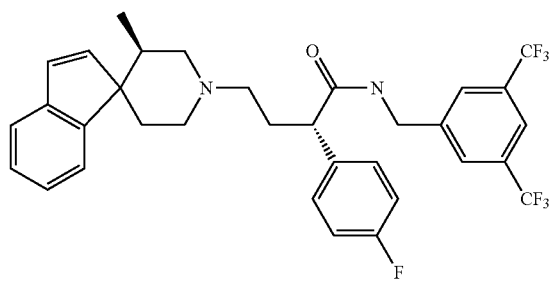 [SMILES: C[C@H]1CN(CC[C@H](C(=O)NCc2cc(C(F)(F)F)cc(C(F)(F)F)c2)c2ccc(F)cc2)CCC12C=Cc1ccccc12] |
| Teijin/BMS | 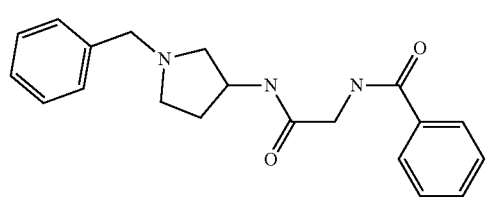
3-Aminopyrrolidines |
| Telik | 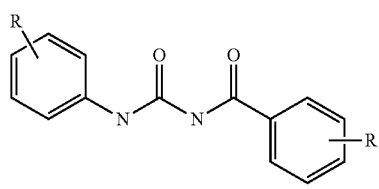 |
| Incyte | 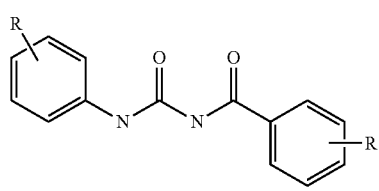
INCB-003284 |
| Takeda | 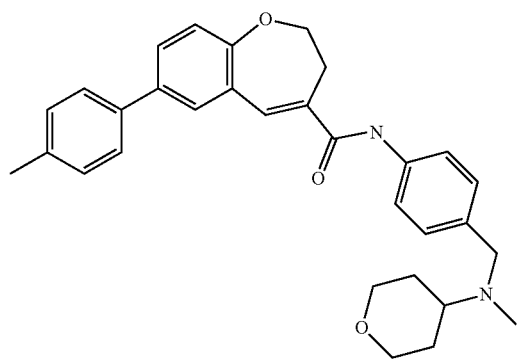 |
| Chemokine Therapeutics | 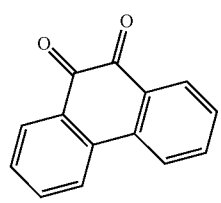 [SMILES: O=C1C(=O)c2ccccc2-c2ccccc21] |

| Company | Compound |
|---|---|
| Pfizer | (structure) |
| Ono | (structure) |
| Ono | (structure) |
| Merck | (structure) |
| Warner-Lambert | (structure) |

Chemokines (e.g., MCP-1/CCL2)

The present disclosure provides the first imaging probe available for CCR2 detection. As described herein, the CCR2 imaging specificity and sensitivity have been well characterized in pre-clinical studies.

Chemokines, or chemotactic cytokines, are small heparin-binding proteins that constitute a large family of peptides (60-100 amino acids) structurally related to cytokines, whose main function is to regulate cell trafficking, particularly that of immune cells, and thus are of relevance to this BRTC application. Chemokines can be classified into four subfamilies on the basis of the number and location of the cysteine residues at the N-terminus of the molecule and are named CXC, CC, CX3C, and C. They initiate their cellular effects via interaction with a specific G protein-coupled receptor. Monocyte chemo-attractant protein chemokines are secreted by a wide variety of cell types under a range of inflammatory conditions such as atherosclerosis, neurodegenerative disease and various forms of cancer. One of the most prominent of these is monocyte chemoattractant protein-1 (MCP-1), now called CCL2, which significantly regulates migration and infiltration of monocytes to the site of inflammation, predominantly through CC-chemokine receptor 2 (CCR2). In the case of the monocyte subsets mentioned above CD16−/Ly6C$^{hi}$ pro-inflammatory monocytes exhibit high CCR2 expression, whereas the CD16+/Ly6C$^{lo}$ low-inflammatory monocytes do not. This interplay and its impact on monocyte trafficking and tissue inflammation really highlight the importance of CCR2 imaging to identify the critical pro-inflammatory monocyte subset as well as potentially track its migration from hematopoietic sites to sites of inflammation in both pre-clinical and clinical research.

CCR2 directs monocytes and other immune cell recruitment in the lung. A major role for the CCL2/CCR2 pair is the recruitment of inflammatory monocytes from the bone marrow and regulation of macrophage, dendritic and T cells maturation. In response to CCL2, CCR2$^+$ monocytes adhere to the vascular endothelial surface and migrate into tissue, along chemotactic gradients. Inflammatory monocytes (mouse Ly6C$^{hi}$ Ly6G$^{lo}$, human CD14$^+$CD16$^-$) serve as precursors for classical macrophages and conventional DCs. CCR2$^+$ monocytes also provide a secondary source of proinflammatory modulators, such as tumor necrosis factor-α, interleukin-1β and matrix metalloproteinases, contributing to lung injury. Although inflammatory monocytes are essential early responders, excessive or prolonged recruitment impairs resolution of inflammation and propagates disease progression.

Molecular Engineering

The following definitions and methods are provided to better define the present invention and to guide those of ordinary skill in the art in the practice of the present invention. Unless otherwise noted, terms are to be understood according to conventional usage by those of ordinary skill in the relevant art.

"Wild-type" refers to a virus or organism found in nature without any known mutation.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Generally, conservative substitutions can be made at any position so long as the required activity is retained. So-called conservative exchanges can be carried out in which the amino acid which is replaced has a similar property as the original amino acid, for example the exchange of Glu by Asp, Gln by Asn, Val by Ile, Leu by Ile, and Ser by Thr. For example, amino acids with similar properties can be Aliphatic amino acids (e.g., Glycine, Alanine, Valine, Leucine, Isoleucine); Hydroxyl or sulfur/selenium-containing amino acids (e.g., Serine, Cysteine, Selenocysteine, Threonine, Methionine); Cyclic amino acids (e.g., Proline); Aromatic amino acids (e.g., Phenylalanine, Tyrosine, Tryptophan); Basic amino acids (e.g., Histidine, Lysine, Arginine); or Acidic and their Amide (e.g., Aspartate, Glutamate, Asparagine, Glutamine). Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. Amino acid sequence can be modulated with the help of art-known computer simulation programs that can produce a polypeptide with, for example, improved activity or altered regulation. On the basis of this artificially generated polypeptide sequences, a corresponding nucleic acid molecule coding for such a modulated polypeptide can be synthesized in-vitro using the specific codon-usage of the desired host cell.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic and Monitoring or Evaluation Methods

Also provided is a process of treating, evaluating, or monitoring a CCR2/CCL2 associated disease, disorder, or condition in a subject in need administration of a therapeutically effective amount of a therapeutic agent (e.g., a CCR2 antagonist), so as to substantially inhibit a CCR2/CCL2 associated disease, disorder, or condition, slow the progress of a CCR2/CCL2 associated disease, disorder, or condition, or limit the development of a CCR2/CCL2 associated disease, disorder, or condition.

Methods described herein are generally performed on a subject in need thereof. A subject in need of the evaluation or therapeutic methods described herein can be a subject having, diagnosed with, suspected of having, or at risk for developing a CCR2/CCL2 associated disease, disorder, or condition. A determination of the need for treatment will typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and chickens, and humans. For example, the subject can be a human subject.

Generally, a safe and effective amount of a therapeutic agent or an imaging agent is, for example, that amount that would cause the desired therapeutic or imaging effect in a subject while minimizing undesired side effects. In various embodiments, an effective amount of a therapeutic agent described herein can substantially inhibit a CCR2/CCL2 associated disease, disorder, or condition, slow the progress of a CCR2/CCL2 associated disease, disorder, or condition, or limit the development of a CCR2/CCL2 associated disease, disorder, or condition.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of an imaging or therapeutic agent can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to evaluate a CCR2/CCL2 associated disease, disorder, or condition, substantially inhibit a CCR2/CCL2 associated disease, disorder, or condition, slow the progress of a CCR2/CCL2 associated disease, disorder, or condition, or limit the development of a CCR2/CCL2 associated disease, disorder, or condition.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level or dose level to be used as an imaging agent for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of an imaging agent or a therapeutic agent can occur as a single event or over a time course of treatment. For example, an imaging agent or a therapeutic agent can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for a CCR2/CCL2 associated disease, disorder, or condition.

A therapeutic agent can be administered simultaneously or sequentially with another agent, such as an antibiotic, an anti-inflammatory, or another agent. For example, a therapeutic agent can be administered simultaneously with another agent, such as an antibiotic or an anti-inflammatory. Simultaneous administration can occur through administration of separate compositions, each containing one or more of a therapeutic agent, an antibiotic, an anti-inflammatory, or another agent. Simultaneous administration can occur through administration of one composition containing two or more of a therapeutic agent, an antibiotic, an anti-inflammatory, or another agent. A therapeutic agent can be administered sequentially with an antibiotic, an anti-inflammatory, or another agent. For example, a therapeutic agent can be administered before or after administration of an antibiotic, an anti-inflammatory, or another agent.

Administration

The imaging agents as described herein can be administered in a subject in an amount effective to produce images in a variety of imaging modalities, such as PET or SPECT. Administration and calculations of amounts of imaging agents are well known in the art and also described in Examples 4 and 5 (see e.g., Long et al., The Chemistry of Molecular Imaging, Wiley, 2014; Saini et al., Spect and MRI Imaging Agents: Brain and Tumor Imaging, Lambert, 2016; Smith et al., Diagnostic Imaging for Pharmacists, A P A, 2012). Except as otherwise noted herein, therefore, the process of the present disclosure can be carried out in accordance with such processes.

Agents and compositions described herein can be administered according to methods described herein in a variety of means known to the art. The agents and composition can be used either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

Agents and compositions described herein can be administered in a variety of methods well known in the arts. For example, administration can be parenteral, pulmonary, oral, topical, intradermal, intramuscular, intraperitoneal, intravenous, subcutaneous, intranasal, epidural, ophthalmic, buccal, or rectal administration. As another example, administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 µm), nanospheres (e.g., less than 1 µm), microspheres (e.g., 1-100 µm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to imaging agents, nanoparticles, peptides (e.g., CCR2 binding peptides), chelators, radiolabelled compositions, buffers. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit, instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Figure 5A:
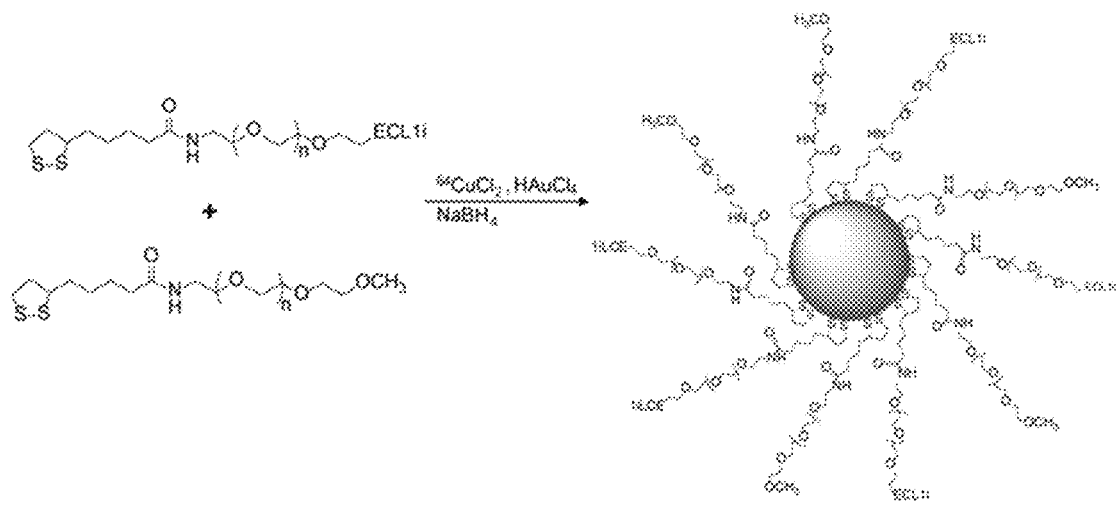
FIG. 5A-FIG. 5C is a series of chemical structures, an image and a histogram showing the synthetic scheme and characterization of $^{64}$CuAuNCs-ECL1i showed straightforward preparation and uniform size distribution.
Figure 5B:
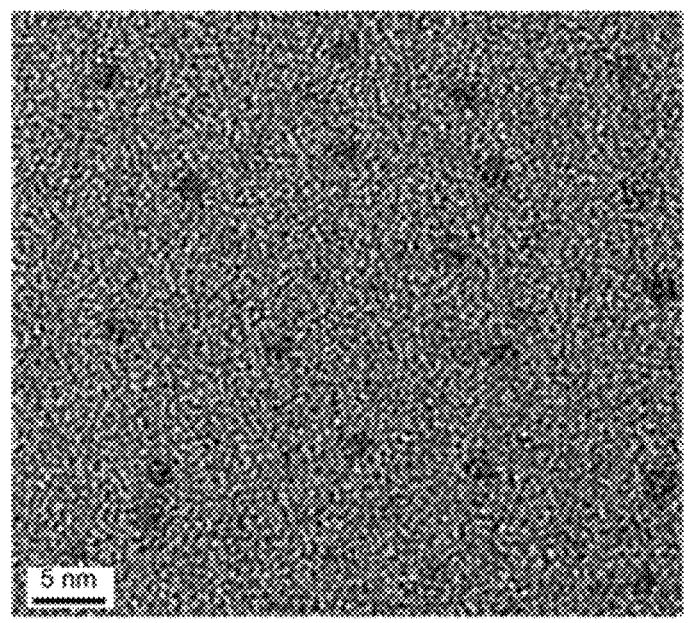
Figure 5C:
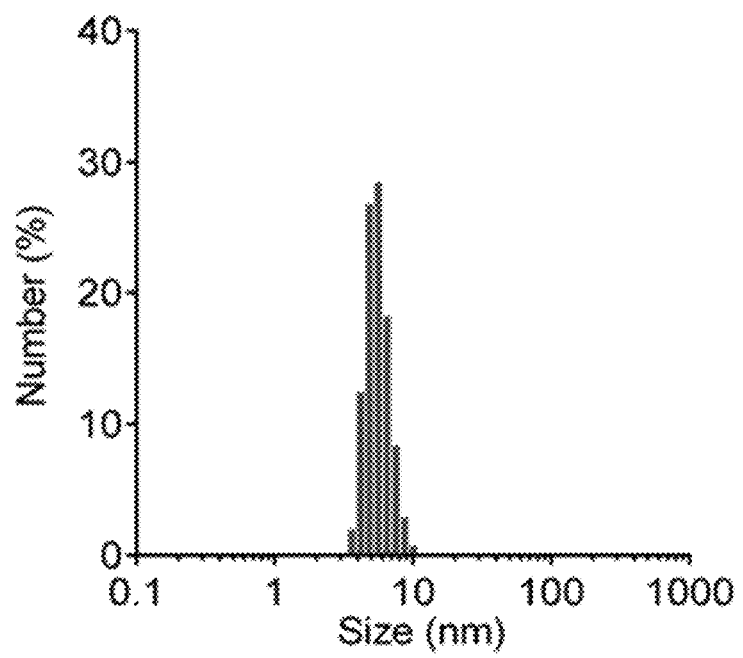

Example 1: Noninvasive Imaging of CCR2+ Cells in Ischemia Reperfusion Injury after Lung Transplantation Here, we show that CCR2 expression in murine lung transplant recipients promotes monocyte infiltration into pulmonary grafts and mediates graft dysfunction. We have developed new positron emission tomography imaging agents using a CCR2 binding peptide ECL1i that can be used to monitor inflammatory responses after organ transplantation. Both $^{64}$Cu-radiolabeled ECL1i peptide radiotracer ($^{64}$Cu-DOTA-ECL1i) (see e.g., FIG. 1) and ECL1i-conjugated gold nanoclusters doped with $^{64}$Cu ($^{64}$CuAuNCs-ECL1i) (see e.g., FIG. 5A-FIG. 5C) showed specific detection of CCR2, which is up-regulated during ischemia-reperfusion injury after lung transplantation. Due to its fast pharmacokinetics $^{64}$Cu-DOTA-ECL1i functioned efficiently for rapid and serial imaging of CCR2. The multivalent $^{64}$CuAuNCs-ECL1i with extended pharmacokinetics is favored for long-term CCR2 detection and potential targeted theranostics. This data shows that the use of these imaging agents can be applicable for diagnostic and therapeutic purposes for a wide variety of immune-mediated diseases.

As described in more detail below, in the wild type (WT) to wild type mouse lung transplantation model, $^{64}$Cu-DOTA-ECL1i tracer was injected via tail vein at 1 h post transplantation and 0-60 min dynamic PET imaging was conducted right after the injection. In the donor lung of WT recipient, strong PET signal was detected, which was nearly 3 times higher than the weak accumulation observed in the native lung. To confirm the targeting specificity, PET imaging was performed in WT mouse to CCR2 knock-out (CCR2$^{-/-}$) mouse lung transplantation model. It was found out that PET signal was only detected in the donor lung from the WT mouse, which confirmed the CCR2 imaging specificity. Moreover, we carried out the CCR2 receptor competitive blocking study by injecting $^{64}$Cu-DOTA-ECL1i and excess amount of ECL1i peptide (ECL1i vs. $^{64}$Cu-DOTA-ECL1i molar ratio=500:1) in the wild type to wild type mouse lung transplantation model. Quantitative PET data analysis showed significantly blocked signal at donor lung compared to uptake in the donor lung without the blocking agent, indicating the CCR2 specific tracer uptake. Besides PET imaging, flow cytometry and immunohistochemistry both demonstrated the over-expression of CCR2 receptor on the donor lungs collected from the WT to WT transplantation model, which confirmed the PET imaging results.

Ischemia reperfusion injury-mediated primary graft dysfunction continues to represent one of the most serious complications after lung transplantation. It does not only contribute to early morbidity and mortality, but has also been shown to be a risk factor for the development of chronic allograft dysfunction (2). Primary graft dysfunction is diagnosed and its severity graded based on the impairment of oxygen exchange and the presence of infiltrates on chest radiographs. Clearly, the identification of reliable biomarkers could facilitate a timely diagnosis. Moreover, elucidating pathways that contribute to the pathogenesis of primary graft dysfunction will allow for the development of targeted therapies. We show that recruitment of CCR2+ cells promotes pulmonary graft dysfunction. Here we have used a new PET probe against CCR2 to image lung grafts during ischemia reperfusion injury. This study demonstrates that infiltration of CCR2+ cells into lung grafts can be detected noninvasively and serially using PET imaging.

Clinically, correlations exist between plasma levels of inflammatory cytokines and chemokines and the development of primary graft dysfunction in lung transplant recipients (19-21). MCP-1, a ligand for CCR2, has been found to be elevated in patients, who suffered from this complication. We show that recruitment of CD11b+Ly6C$^{hi}$ monocytes to pulmonary grafts is significantly reduced when recipients are deficient in CCR2. Based on our previous observation that monocytes mediate transendothelial migration of neutrophils in injured lungs, we speculate that amelioration of ischemia reperfusion injury in CCR2-deficient recipients may in part be due to reduced neutrophilic infiltration (4). Collectively, these clinical and experimental studies indicate that CCR2 is an important contributor to ischemia reperfusion injury and therefore could serve as a biomarker of primary graft dysfunction and also as a therapeutic target.

PET imaging has been used experimentally and clinically by our group and others to evaluate transplanted organs (15, 18, 22-24). However, to date no imaging probe has been available to detect the CCR2 receptor in vivo, which is expressed on monocytes and other cell types that are known to mediate inflammatory responses after transplantation (25, 26). Here, we showed that a CCR2 binding peptide can specifically detect these receptors with PET/CT imaging during lung transplant-mediated ischemia reperfusion injury in vivo both as a monovalent peptide tracer and a multivalent nanoplatform (27).

ECL1i has been recently demonstrated to selectively bind CCR2 in a non-competitive way compared to CCL2 ligand in vitro (27). In this study, $^{64}$Cu-DOTA-ECL1i retention was primarily detected in the lung graft after transplantation into syngeneic CCR2-deficient recipients, consistent with the presence of donor monocytes in pulmonary grafts. Given the lack of CCR2 receptor in these hosts, we suggest that the minimal localization in native lungs was due to non-specific retention. Thus, if the localization of $^{64}$Cu-DOTA-ECL1i in the native CCR2-deficient lung is due to non-specific background retention, more than 70% of the observed accumulation in the graft is due to CCR2-mediated uptake, given that $^{15}$O—H$_2$O imaging did not show a difference in blood flow.

After lung transplantation into wild type recipients the PET/CT images showed considerable accumulation of CCR2+ cells in the whole body. Consistent with other inflammatory models our work has shown that CCR2 is critical to mobilize CD11b+Ly6C$^{high}$ monocytes from the bone marrow after lung transplantation (28, 29). In some settings CCR2 may promote monocyte recruitment from the peripheral blood into inflamed sites (30). Our imaging indicates that CCR2+ cells are rapidly released into the periphery after engraftment of lungs. Through competitive receptor blocking, approximately 75% of the PET signal in the grafts was blocked after transplantation into wild type recipients, resulting in comparable retentions in both native and donor lungs. The consistent results between CCR2 receptor-specific uptake from the calculation after transplantation into CCR2-deficient hosts and the blocking percentage after engraftment into wild type recipients support the specificity of $^{64}$Cu-DOTA-ECL1i binding CCR2.

In contrast to monovalent $^{64}$Cu-DOTA-ECL1i peptide tracers, we observed six-fold higher retention in the blood 1 hour after injection of targeted $^{64}$CuAuNCs-ECL1i nanoclusters, confirming the advantage of multivalent nanoclusters for improved CCR2 detection (17). More importantly, the targeted $^{64}$CuAuNCs-ECL1i probe demonstrated specific retention in donor grafts and minimal localization in native lungs. If the low and non-specific accumulation of $^{64}$CuAuNCs in native lungs is set as background, more than 80% of the accumulation of $^{64}$CuAuNCs-ECL1i in pulmonary grafts was due to CCR2-mediated uptake, demonstrating specific and persistent imaging of CCR2. Furthermore, these specificity values were significantly higher than those for the $^{64}$Cu-DOTA-ECL1i peptide tracer, underscoring the usefulness of multivalent nanoclusters for enhanced targeting and longitudinal imaging.

In conclusion, PET imaging of CCR2$^+$ cells with targeted molecular probes can serve as a biomarker for primary graft dysfunction after lung transplantation. Additionally, the targeted nanoclusters provide a theranostic platform for image-guided delivery of specific treatment. These imaging approaches could be useful for a variety of CCR2-mediated inflammatory conditions, both sterile and infectious.

Recipient CCR2 Expression Promotes Monocyte Recruitment to Pulmonary Grafts and Ischemia Reperfusion Injury after Lung Transplantation.

Figure 3A:
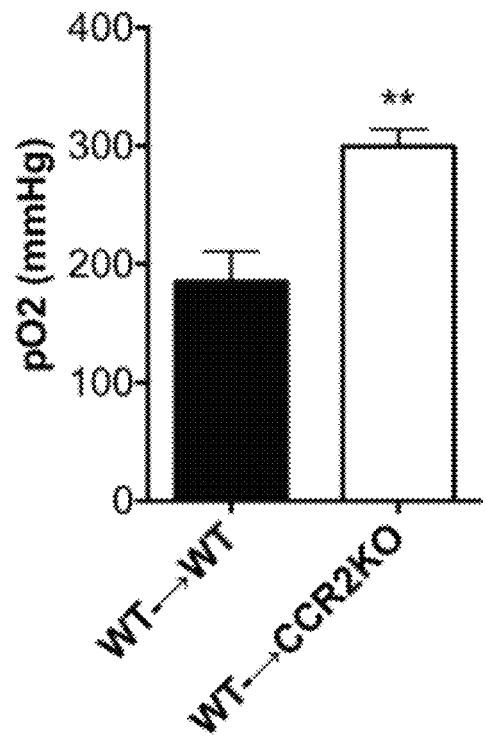
FIG. 3A-FIG. 3C is a series of graphs and histograms showing lung transplant recipient CCR2 expression promotes monocyte recruitment into lung grafts and mediates ischemia reperfusion injury.
Figure 3B:
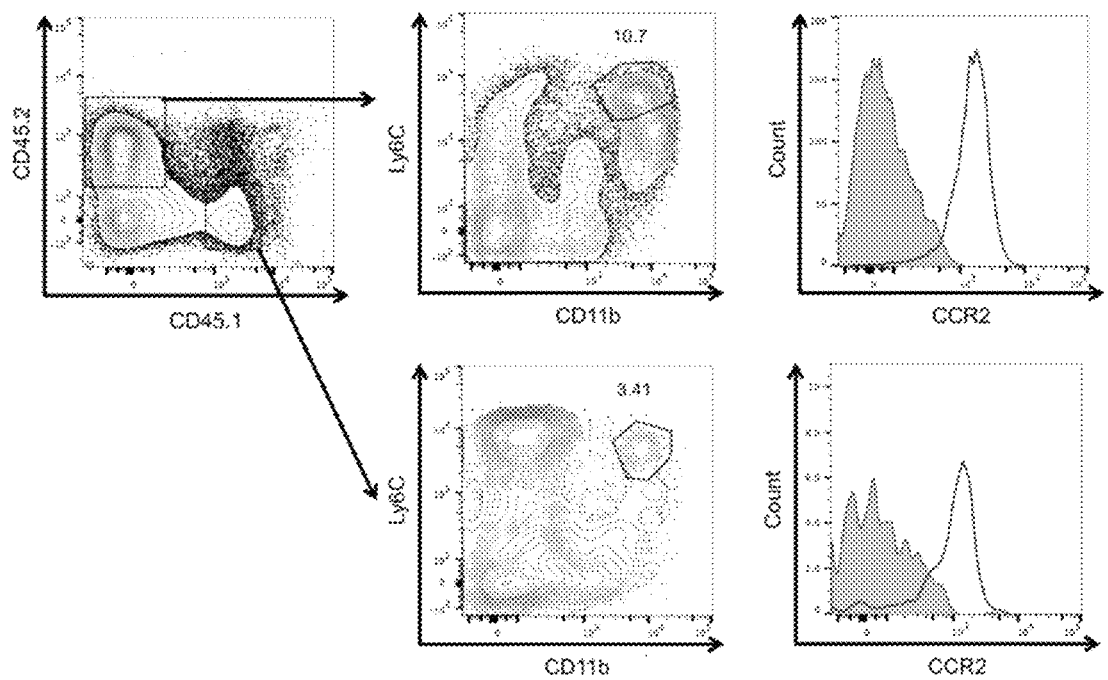
Figure 3C:
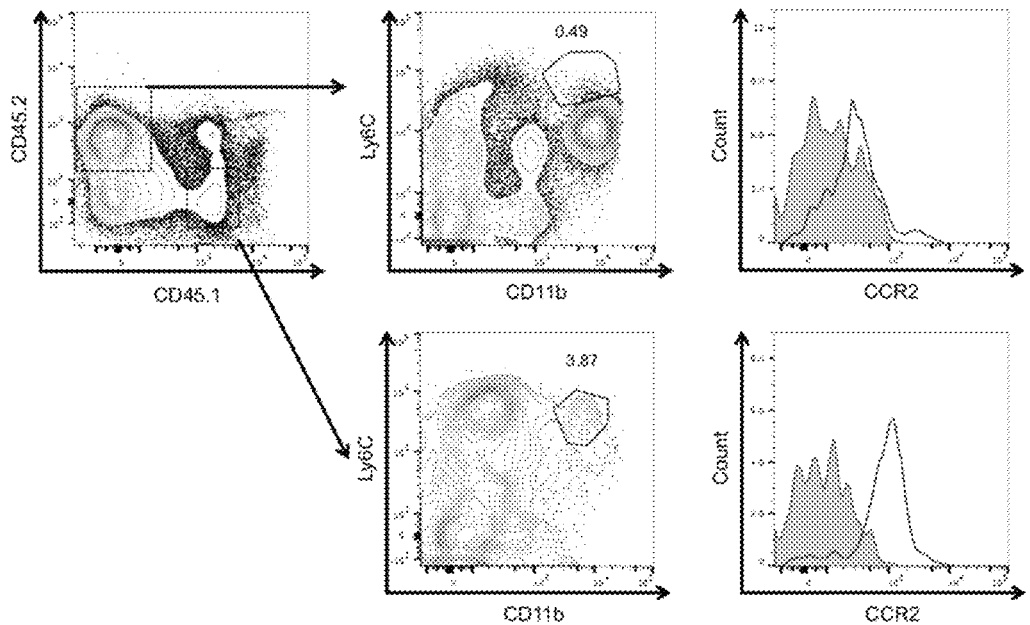
Figure 4:
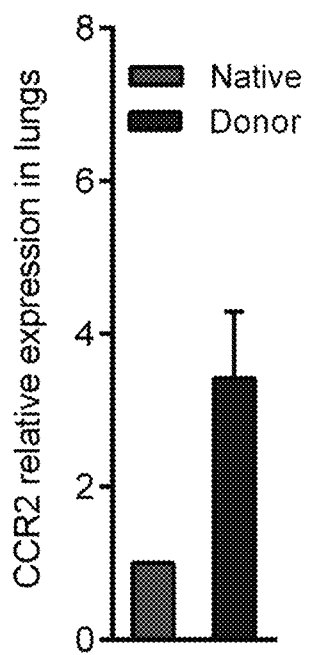
FIG. 4 is a bar graph showing CCR2 RT-PCR confirmed the up-regulation of CCR2 following lung transplantation. RT-PCR showing the relative expression of CCR2 mRNA in native and donor lungs 24 hours after B6 wild type→B6 wild type transplantation (n=4).

To assess how recipient expression of CCR2 impacts ischemia reperfusion injury wild type B6 lungs were transplanted into syngeneic wild type or CCR2-deficient recipients. Lack of CCR2 expression in the host resulted in significant amelioration in ischemia reperfusion injury as evidenced by improvement in oxygen exchange (see e.g., FIG. 3A). We next transplanted B6 CD45.1 wild type lungs into congenic B6 CD45.2 wild type (see e.g., FIG. 3B) or B6 CD45.2 CCR2-deficient recipients (see e.g., FIG. 3C) and evaluated recipient (CD45.2) and donor (CD45.1) monocytes within the pulmonary grafts 6 hours later. We noticed a substantial reduction in graft infiltration of recipient monocytes (CD11b$^+$Ly6C$^{hi}$) when the hosts lacked CCR2 expression. Notably, a small population of CCR2-expressing monocytes of donor origin was present in wild type grafts after transplantation into either wild type or CCR2-deficient recipients. These findings were corroborated by gene expression analysis (see e.g., FIG. 4).

Biodistribution of $^{64}$Cu-DOTA-ECL1i and $^{64}$CuAuNCs-ECL1i.

To assess the pharmacokinetics of $^{64}$Cu-DOTA-ECL1i, biodistribution was performed at 1 hour after transplantation of wild type B6 lungs into wild type recipients and showed fast clearance primarily through the kidneys, with minor accumulation in the liver, spleen and negligible uptake in other organs (see e.g., FIG. 6A), consistent with other peptide tracers (14). After transplantation of wild type B6 lungs into wild type B6 recipients, the uptake in the donor lung was more than twice the uptake in the native lung.

Compared to the monovalent $^{64}$Cu-DOTA-ECL1i peptide tracer, multivalent $^{64}$CuAuNCs-ECL1i nanoclusters demonstrated extended blood circulation at 1 hour after transplantation with significant renal clearance due to the small size (see e.g., FIG. 6). The progressive diminution in liver activity with stable uptake in the gastrointestinal tract indicated effective hepatobiliary excretion (17). In contrast to the decreased activity in blood pool organs observed with the peptide, the localization of the targeted nanoclusters in spleen and bone marrow remained constant throughout the 24 hour imaging period.

In Vivo PET Imaging of $^{64}$Cu-DOTA-ECL1i Peptide Tracer.

Figures 7A, 7B:
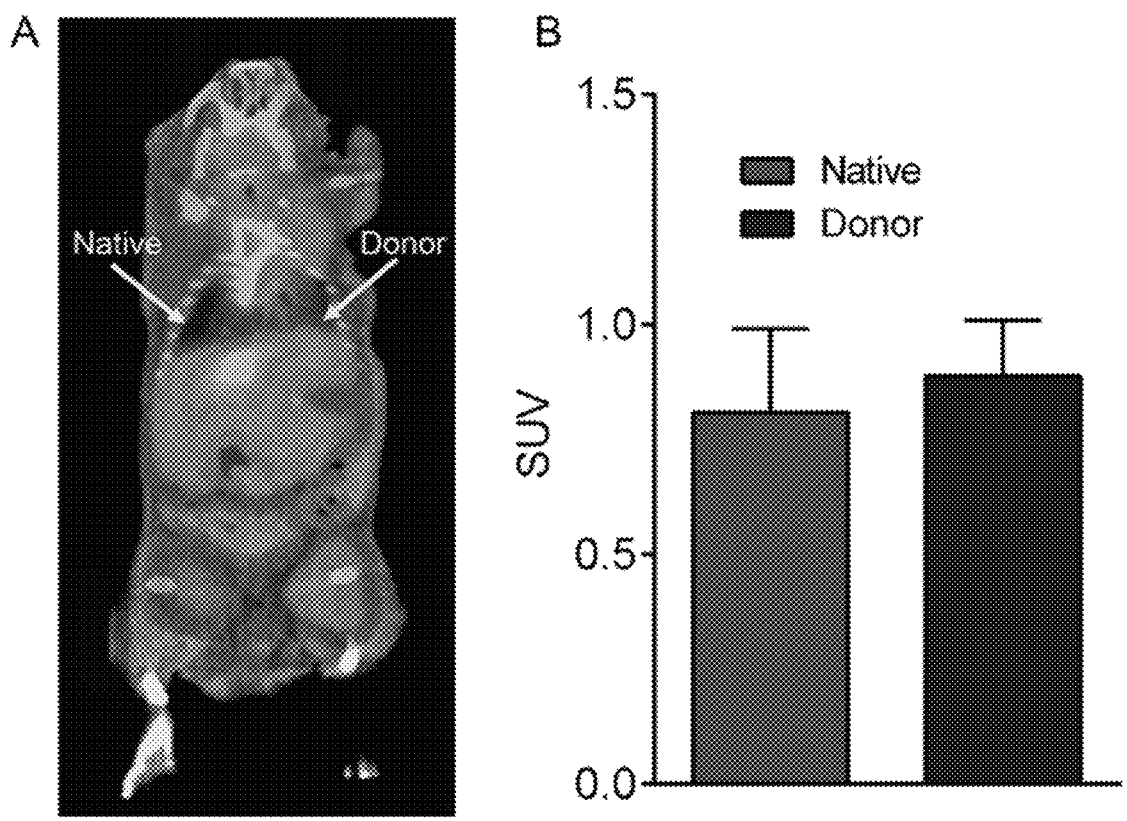
FIG. 7A-FIG. 7B is a PET image and a bar graph showing $^{15}$O-water PET imaging demonstrated comparable blood flow between donor and native lungs after transplantation.
Figures 8A, 8B, 8C:
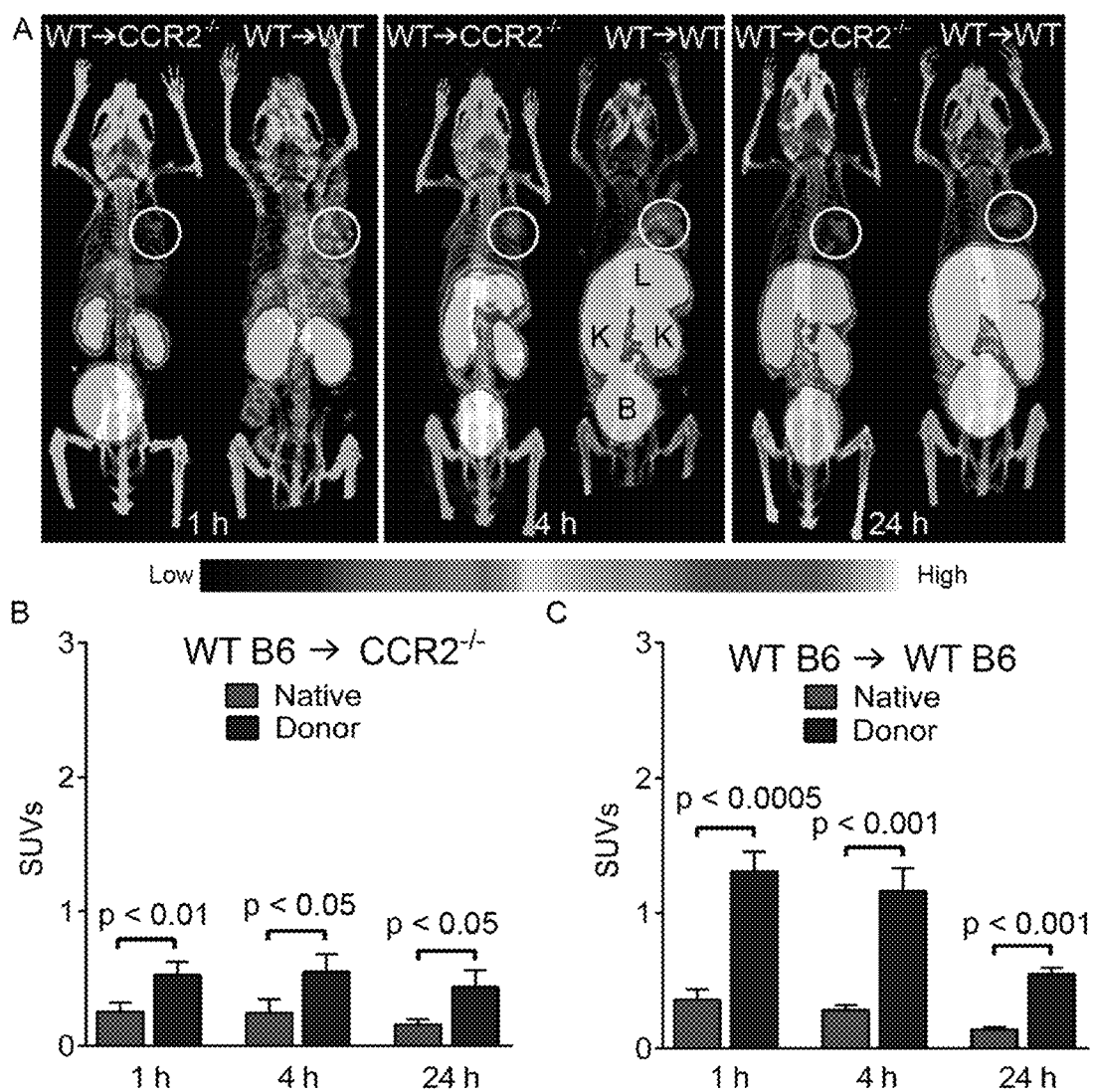
FIG. 8A-FIG. 8B is a series of PET images and bar graphs showing CCR2 is detected by $^{64}$CuDOTA-ECL1i using PET.
Figure 9:
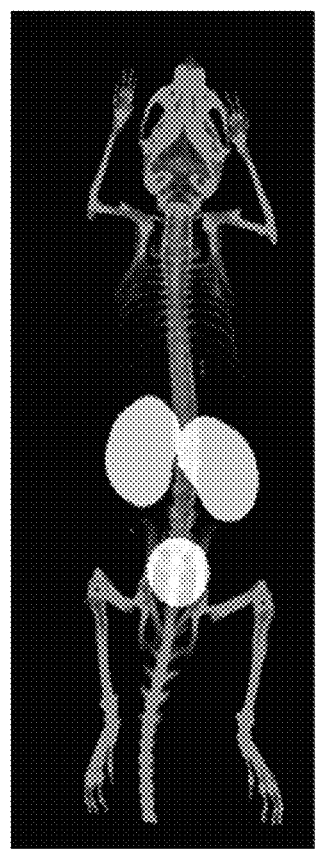
FIG. 9 is a PET image of $^{64}$Cu-DOTA-ECL1i PET imaging in naïve mouse demonstrated imaging specificity.

We next wanted to assess whether differences existed between blood flow to the transplanted graft and the native lung. To this end, PET using $^{15}$O-water provides a direct physiologic measurement of circulatory parameters for regional blood and vascular volume (16). PET/CT images of $^{15}$O water at 1 hour after transplantation showed similar signals in both graft and native lung (see e.g., FIG. 7). Comparable SUV activities were observed in grafts and native lungs after transplantation of wild type B6 lungs into syngeneic wild type hosts, yielding a graft/native lung uptake ratio of 1.09±0.28. In contrast, $^{64}$Cu-DOTA-ECL1i imaging in wild type recipients of wild type lungs showed uptake in the graft with minimal signal retained in the native lung at 1 hour after transplantation (see e.g., FIG. 8A, FIG. 8B), resulting in a graft/native lung uptake ratio of 3.71±0.44. These results were indicative of infiltration of CCR2$^+$ cells into lung grafts at these time points. A PET signal was predominantly observed in B6 wild type lungs after transplantation into CCR2-deficient recipients, consistent with donor CCR2$^+$ cells being present in these grafts at this time point. In the absence of graft infiltration of recipient CCR2$^+$ cells, the uptake in these pulmonary grafts was only 40% of that observed in wild type lungs after transplantation into wild type hosts. The activity of $^{64}$Cu-DOTA-ECL1i retained in both lungs measured from background scans was less than 10% of the uptake acquired after the re-injection of $^{64}$Cu-DOTA-ECL1i at 4 or 24 hours. Thus, the rapid clearance of this peptide tracer in lungs indicates that it can be used for serial scans in a short time period allowing for the assessment of dynamic expression of CCR2. A high intensity of PET signal in the kidney also corroborated the renal clearance determined by the biodistribution study. PET imaging performed on naïve mice showed minimal tracer uptake in the lungs (see e.g., FIG. 9).

Figures 10A, 10B:
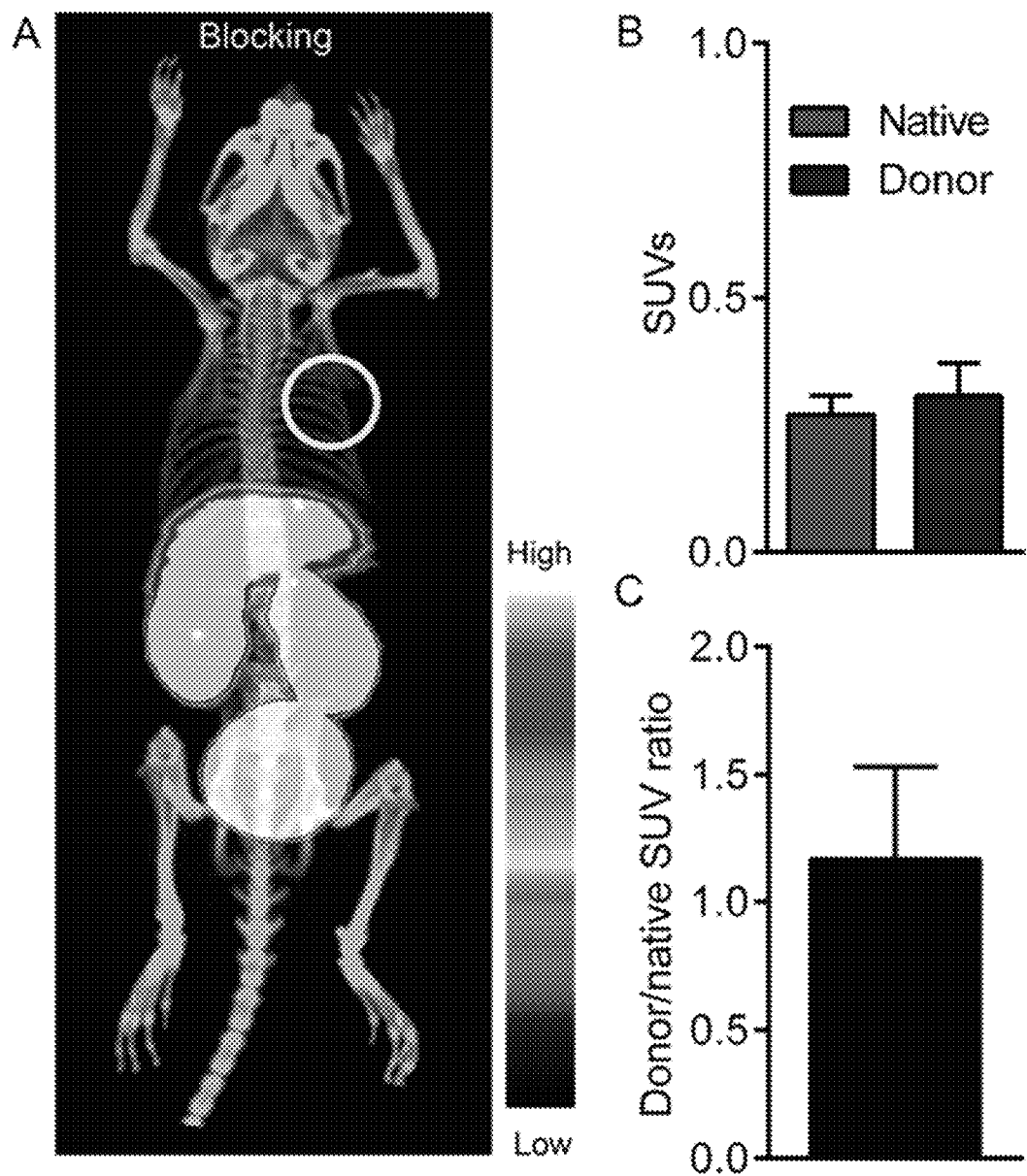
FIG. 10A-FIG. 10B is a PET image and bar graphs showing competitive CCR2 receptor blocking study confirmed $^{64}$Cu-DOTA-ECL1i imaging specificity.

The uptake in both grafts and native lungs of wild type recipients progressively decreased at 4 and 24 hours likely reflecting temporal changes of CCR2$^+$ cell infiltration or expression of the receptor on these cells. However, the PET intensities in the pulmonary grafts were significantly higher than those in the native lungs at these later time points. The graft/native lung uptake ratio reached a peak at 4 hours (4.13±0.32) and at 24 hours decreased to a level (3.73±0.45) similar to that observed at 1 hour. Unlike the 63% decreased uptake in the donor lung in the wild type B6→wild type B6 combination at 24 hours, we found no significant difference between the three examined time points (1, 4, and 24 hours) in wild type lung grafts after transplantation into CCR2-deficient recipients. However, at all time-points, the uptake in the graft was significantly higher than in the native lung reflecting the presence of CCR2$^+$ cells that are carried over with the transplanted lung (see e.g., FIG. 8A, FIG. 8B). When we co-injected non-radiolabeled ECL1i, the uptake of $^{64}$Cu-DOTA-ECL1i in the pulmonary grafts at 1 hour after transplantation into wild type hosts was significantly decreased to a level comparable to that in native lungs (see e.g., FIG. 10) resulting in a significant decrease in the graft/native lung uptake ratio (1.17±0.36), indicating binding specificity of the probe.

Figures 11A, 11B:
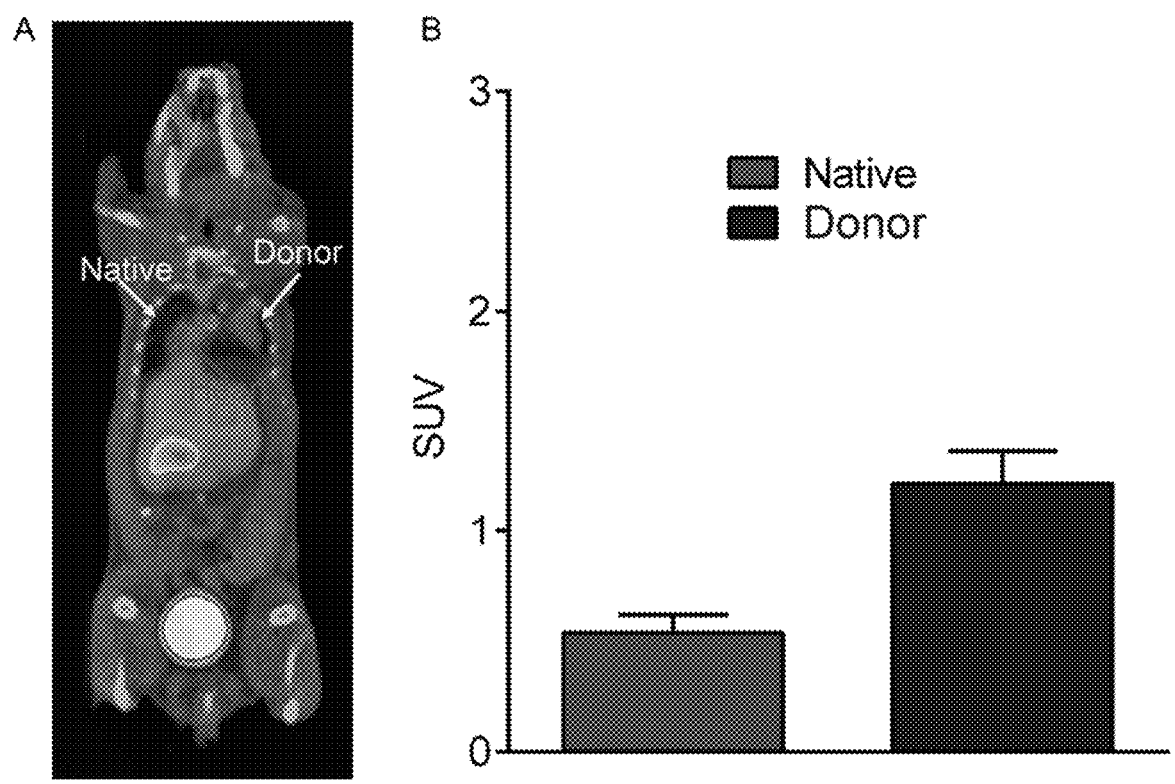
FIG. 11A-FIG. 11B is a PET image and a bar graph showing $^{18}$F-FDG PET imaging of uptake in the donor lung.
Figure 12A:
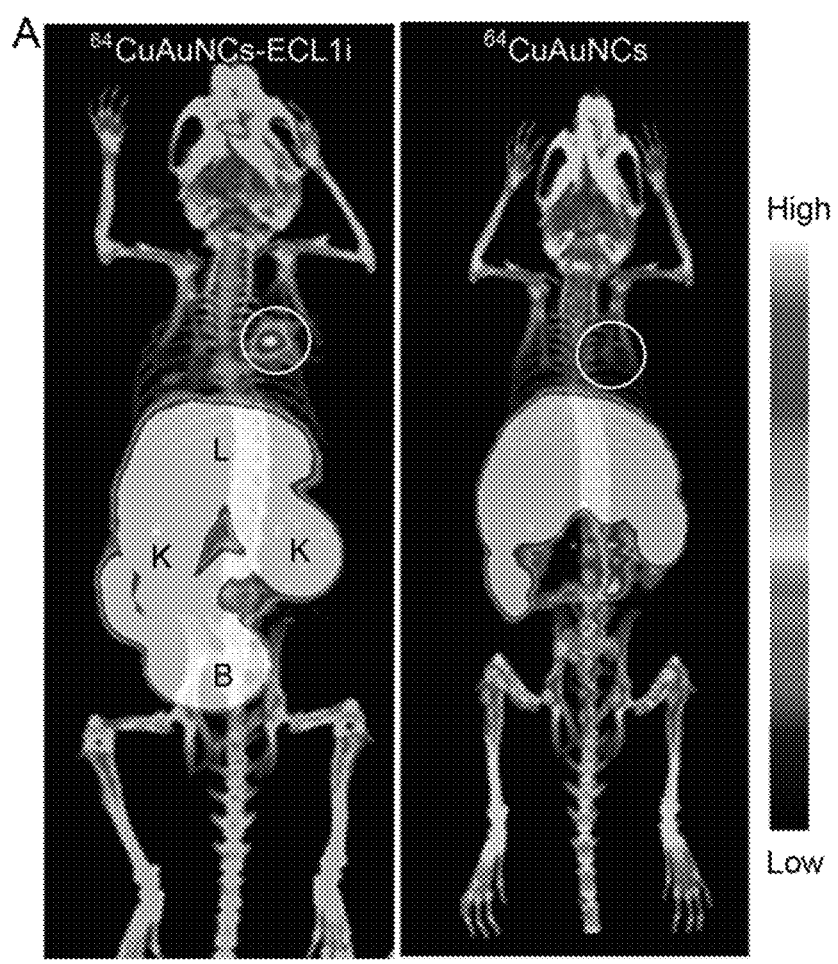
FIG. 12A-FIG. 12D is a series of PET images and bar graphs showing CCR2 is detected by $^{64}$CuAuNCs-ECL1i with enhanced efficiency using PET.
Figure 12B:
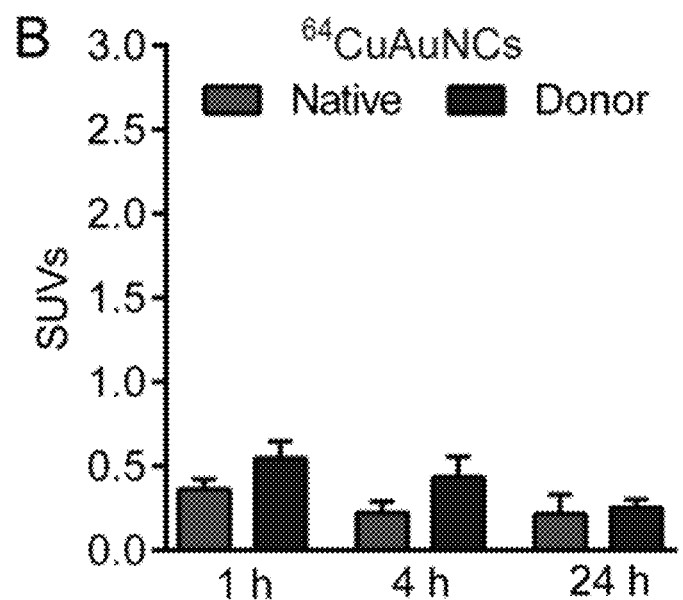
Figure 12C:
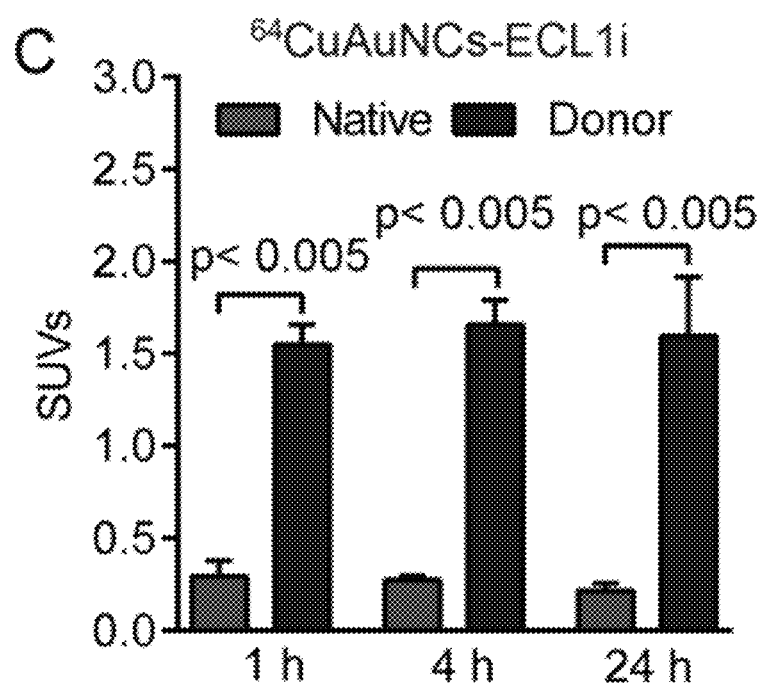
Figure 12D:
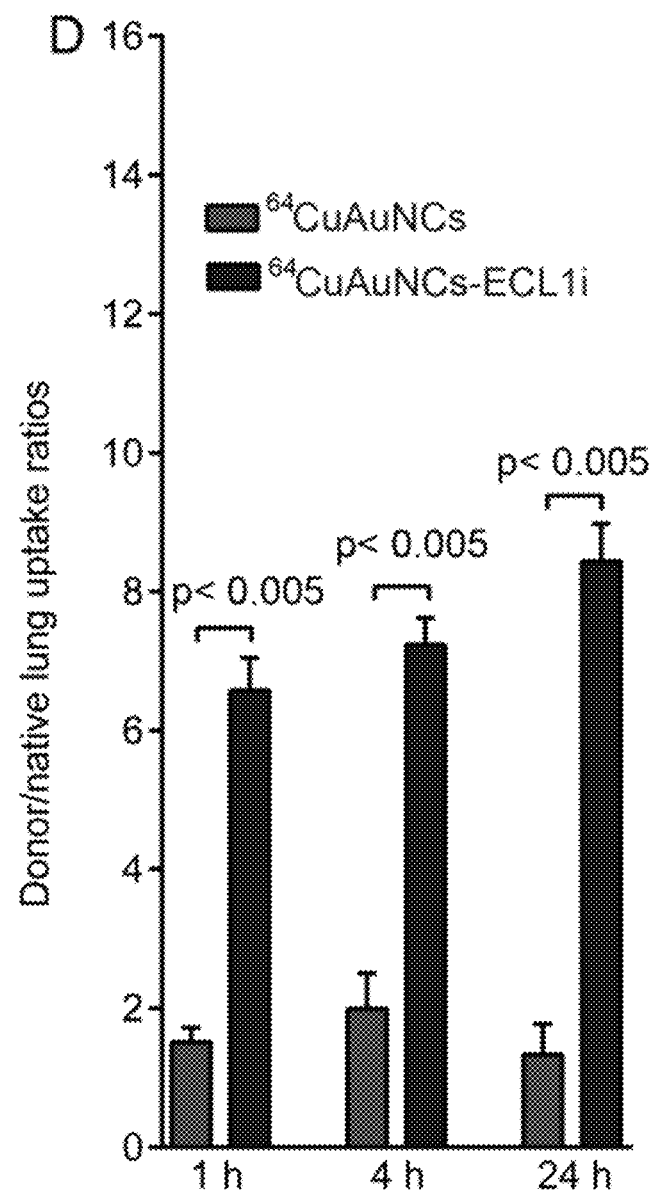

We have previously reported that $^{18}$F-FDG PET can be used to detect graft rejection after pulmonary transplantation, which has been linked to glucose uptake by graftinfiltrating T cells (18). $^{18}$F-FDG PET/CT showed significantly higher uptake in the donor graft than native lung at 1 hour after wild type B6→wild type B6 transplantation (see e.g., FIG. 11). However, the FDG imaging yielded a graft/native lung uptake ratio of 2.29±0.037, which was significantly lower than the data acquired with $^{64}$Cu-DOTA-ECL1i.

In Vivo PET/CT Imaging of $^{64}$CuAuNCs-ECL1i Nanoclusters.

Based on the in vivo pharmacokinetics of the multivalent $^{64}$CuAuNCs-ECL1i nanocluster, PET/CT images were acquired at 1, 4 and 24 hours following engraftment for both CCR2-targeted $^{64}$CuAuNCs-ECL1i and non-targeted $^{64}$CuAuNCs in the wild type B6→wild type B6 combination. At 4 hours after transplantation, uptake of $^{64}$CuAuNCs-ECL1i was observed in the grafts with minimal accumulation in the native lungs yielding a graft/native lung uptake ratio of 6.58±0.47 (see e.g., FIG. 12). For non-targeted $^{64}$CuAuNCs, the signal in the graft was significantly lower while the uptake in the native lung was comparable to the targeted counterpart, resulting in a significantly lower graft/native lung ratio (1.51±0.20). Due to their small size and neutral surface charge (see e.g., FIG. 5), both nanoclusters were cleared through the genitourinary system, confirming the pharmacokinetic data. At 24 hours, the targeted $^{64}$CuAuNCs-ECL1i nanocluster showed relatively stable uptake in both lungs while the signal was somewhat diminished in the pulmonary graft after injection of non-targeted $^{64}$CuAuNCs nanoclusters. Notably, the graft/native lung ratio of $^{64}$CuAuNCs-ECL1i gradually increased from 7.24±0.38 at 4 hours to 8.44±0.54 at 24 hours. These values were significantly higher than those obtained with the non-targeted counterpart.

Mice and Surgical Procedures.

C57BL/6 (B6), B6 CD45.1 and B6 CCR2-deficient mice were purchased from The Jackson Laboratories (Bar Harbor, ME) and maintained in pathogen-free facilities at Washington University. Orthotopic left lung transplants were performed following 1 hour of storage in low-potassium-dextran solution at 4° C. unless otherwise specified (13). Arterial blood gases were measured using an iSTAT Portable Clinical Analyzer (iSTAT) (FiO$_2$ 1.0) after clamping the right pulmonary hilum for 5 minutes.

PET Imaging.

At 1 hour after transplantation, 0-60 min dynamic PET/CT scan was performed following injection of $^{64}$Cu-DOTA-ECL1i (100 µCi in 100 µL saline) with microPET Focus 220 (Siemens, Malvern, PA) or Inveon PET/CT system (Siemens, Malvern, PA). For PET/CT imaging at 4 and 24 hours after transplantation, a 30-minute background scan (10 min/frame, 3 frames) was performed prior to injecting $^{64}$Cu-DOTA-ECL1i (100 µCi in 100 µL saline). The in vivo retention of $^{64}$Cu-DOTA-ECL1i in the donor lung from the previous injection was quantified and subtracted from the uptake value at 4 or 24 hours. For $^{64}$CuAuNCs-ECL1i, PET/CT was carried out 1 hour after transplantation. Instead of a dynamic scan, a static scan was performed at 1, 4 and 24 hours after injection. The PET images were reconstructed with the maximum a posteriori algorithm and analyzed by Inveon Research Workplace. The organ uptake was calculated as percent injected dose per gram (% ID/g) of tissue in three-dimensional regions of interest without the correction for partial volume effect (14). Competitive PET blocking studies were performed immediately after transplantation with co-injection of non-radiolabeled ECL1i and $^{64}$Cu-DOTA-ECL1i (ECL1: $^{64}$Cu-DOTA-ECL1i molar ratio=500:1) followed by a 0-60 minute dynamic scan. $^{18}$F-FDG (250 µCi in 100 µL saline) PET/CT was performed following the same protocol as $^{64}$Cu-DOTA-ECL1i (15). To measure blood flow changes in lungs caused by the surgical procedure, $^{15}$O-water (~1 mCi) was injected intravenously into mice used for $^{64}$CuNCs-ECL1i imaging at 1 hour after transplantation, followed by a 0-10 minute dynamic scan. The relative blood flow change was evaluated by standardized uptake values (SUVs) (16).

Statistical Analysis.

Group variation is described as mean±SD. Groups were compared using 1-way ANOVA with a Bonferroni post-test. Individual group differences were determined with use of a 2-tailed Mann-Whitney test. The significance level in all tests was P<0.05. Prism, version 6.07 (GraphPad, La Jolla, CA), was used for statistical analyses. Error bars designate standard deviation of the mean unless indicated otherwise.

Reagents.

Materials were purchased from Sigma-Aldrich (St. Louis, MO) and used without further purification unless otherwise stated. The $^{64}$Cu (half-life=12.7 h, $\beta^+$=17%, $\beta^-$=40%) was produced at the Washington University (15). Functionalized poly(ethylene glycol) (PEG) derivatives were obtained from Intenzyne Technologies (Tampa, FL). Maleimido-mono-amide-DOTA was purchased from Macrocyclics (Dallas, TX). ECL1i peptide d(LGTFLKC) was customized by CPC Scientific (Sunnyvale, CA). Amicon tubes were purchased from EMD Millipore (Billerica, MA). The reverse phase-high performance liquid chromatography system was equipped with a UV/VIS detector (Dionex, Sunnyvale, CA), a radioactivity detector (B-FC-3200; BioScan Inc., Poway, CA) and a C-18 column (5 mm, 4.6×220 mm; Perkin Elmer, Waltham, MA). Polymeric materials were characterized by $^1$H and $^{13}$C nuclear magnetic resonance spectroscopy using either a Varian 500 MHz or Varian 600 MHz instrument with the residual solvent signal as an internal reference. Fast protein liquid chromatography was performed in PBS buffer on an ÄKTA system equipped with TSK Gel Guard SW$_{XL}$ column (40×6.0 mm, 7 µm) and G3000SW$_{XL}$ column (300×7.8 mm, 5 µm) connected in series and UV/VIS (GE) and radioactivity (BioScan Inc.) detectors.

Synthesis and $^{64}$Cu Radiolabeling of DOTA-ECL1i.

Figures 2A, 2B:
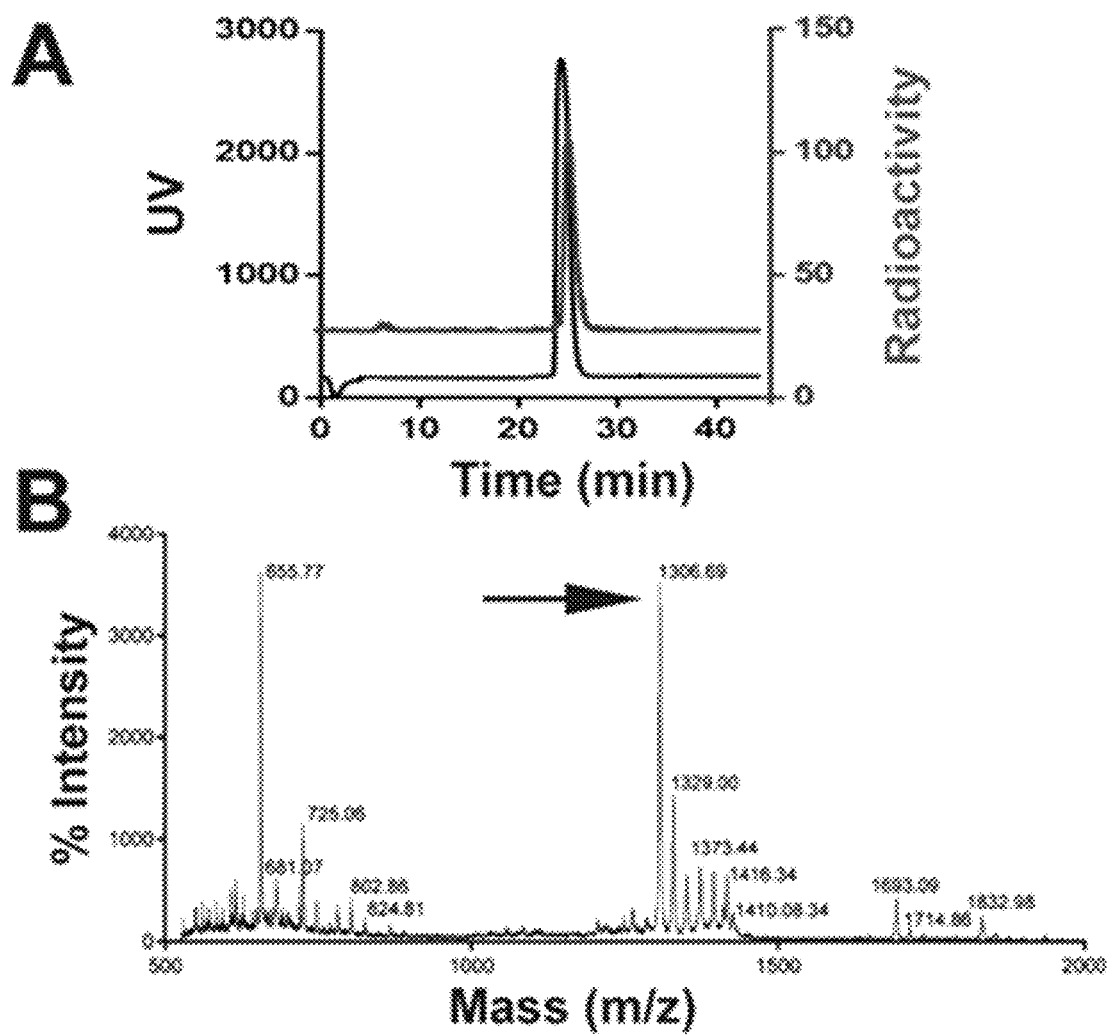
FIG. 2A-FIG. 2B is a series of plots showing the characterization of $^{64}$Cu-DOTA-ECL1i.

ECL1i (DLeu-Gly-DThr-DPhe-DLeu-DLys-DCys) (1.562 mg, 0.2 µmol) and maleimido-mono-amide-DOTA (1.573 mg, 0.2 µmol) (Macrocyclics) conjugation was performed in pH 7.4 phosphate buffer at 4° C. overnight (See e.g., FIG. 1). The crude conjugate was purified by HPLC to reach 99% chemical purity and characterized by mass spectrometry, which confirmed the presence of one DOTA per peptide (M$^+$ calculated 1306.65, found: 1306.69, ABI 4700 MALDI TOF-TOF). DOTA-ECL1i (see e.g., FIG. 1, FIG. 2A-FIG. 2B) (10 µg, 7.66 nmol) was incubated with $^{64}$Cu (2 mCi) in 50 µL of 0.1 M pH 5.5 NH$_4$OAc buffer at 43° C. for 1 hour, with a yield of 95.6%±2.8% (n=12). The specificity activity of $^{64}$Cu-DOTA-ECl1i was determined as 261±7.6 µCi/nmol (see e.g., FIG. 5A-FIG. 5C).

Synthesis of TA-PEG-OMe.

A solution of NH$_2$-PEG750-OMe (0.13 g, 0.17 mmol) in DCM (0.4 mL) was added dropwise to a mixture of thioctic acid (0.034 g, 0.17 mmol), DCC (0.035 g, 0.17 mmol) and 4-dimethylaminopyridine (0.0040 g, 0.033 mmol) in DCM (0.8 mL). After overnight stirring, the mixture was filtered and then rinsed with ethyl acetate. The combined filtrate was dried and the residue was dissolved in H$_2$O. The aqueous solution was extracted with diethyl ether once and saturated with NaHCO$_3$. The aqueous solution was extracted with DCM and the organic phase was dried over anhydrous sodium sulfate. After evaporation of the solvent, the residue was purified by chromatography on silica gel (DCM:ethanol=10:1, v/v) to obtain the final product as a light yellow solid. $^1$H NMR (CDCl$_3$, 400 MHz) δ (ppm): 6.23 (bs, 1H), 3.64 (m), 3.53 (m, 4H), 3.43 (m, 2Hs), 3.37 (s, 3Hs), 3.16 (m, 1H), 3.12 (m, 1H), 2.46 (sextet, 1H, J=6.4 Hz), 2.19 (t, 2Hs, J=7.6 Hz), 1.90 (m, 1H), 1.70 (m, 4Hs), 1.45 (m, 2Hs). $^{13}$C NMR (CDCl$_3$, 100 MHz) δ (ppm): 25.37, 28.93, 34.66, 36.32, 38.45, 39.14, 40.22, 56.42, 59.04, 69.93, 70.20, 70.51, 70.55, 71.92, 172.77.

TA-PEG-ECL1i.

PBS (pH=7.4 1 mL) was added to TA-PEG-Maleimide (Mw=884.11, 2.42 mg, 0.0031 mmol) in a centrifuge vial. When the TA-PEG-Maleimide was completely dissolved, the solution was added to ECL1i peptide (2.74 mg, 0.0031 mmol). After the mixture was stirred overnight at 4C, the solution was purified by RP-HPLC with a H$_2$O/MeCN solvent system. The product was recovered by lyophilization. MALDI-MS for C$_{75}$H$_{129}$N$_{11}$O$_{24}$S$_3$: M$^+$ calculated: 1663.84; found: 1663.53 (ABI 4700 MALDI TOF-TOF).

Synthesis of Non-Radioactive Nanoclusters.

In a typical reaction, water (0.488 mL), HAuCl$_4$ (10 mM, 50 μL), and CuCl$_2$ (1 mM, 5 μL) were mixed in a glass vial, followed by the dropwise addition of TA-PEG-OMe (MW=750 Da, 2.5 mM, 600 μL). Sodium borohydride (40 mM, 175 μL) was added to the mixture and rapidly stirred at room temperature for 4 hours. The CuAu nanoclusters (CuAuNCs) were purified by centrifugation filtration (Amicon, 10K) and washed with pH 7.4 phosphate buffer three times.

Synthesis of $^{64}$CuAuNCs.

The $^{64}$Cu incorporated AuNCs ($^{64}$CuAuNCs) were prepared following the same procedure as described for non-radioactive CuAu nanoclusters. Instead of adding CuCl$_2$, radioactive $^{64}$CuCl$_2$ (4.2 mCi) was added. The synthesized $^{64}$CuAuNCs was then purified by centrifugation filtration (Amicon, 10K) and washed with phosphate buffer (pH=7.4) three times. The radiochemical purity was determined by instant radio-thin layer chromatography (Radio-TLC).

Synthesis of $^{64}$CuAuNCs-ECL1i.

Water (0.334 mL), HAuCl$_4$ (10 mM, 25 μL) were mixed in a glass vial, followed by the dropwise addition of TA-PEG-ECL1i (5 mM, 100 μL) and TA-PEG-OMe (M$_W$ of PEG=750 Da, 2.5 mM, 100 μL). After addition of $^{64}$CuCl$_2$ (1.2 mCi), sodium borohydride (40 mM, 100 μL) was added to the mixture with rapid stirring at room temperature and then continued for at least 4 hours. The $^{64}$CuAuNCs-ECL1i were purified by centrifugation filtration (Amicon, 10K) and washed with phosphate buffer (pH=7.4) three times. The radiochemical purity was determined by instant radio-thin layer chromatography (Radio-TLC) to reach ≥95% radiochemical purity for animal studies and the specific activity was 1.07 mCi/nmol.

Characterization of DOTA-ECL1i.

For example, a 2,2',2''-(10-(2-((2-(2,5-dioxo-2,5-dihydro-1H-pyrrol-1-yl)ethyl)amino)-2-oxoethyl)-1,4,7,10-tetraazacyclododecane-1,4,7-triyl)triacetic acid (Maleimido-mono-amide-DOTA) chelator was conjugated to a cysteine residue of the peptide (DOTA-ECL1i) in pH 7.4 phosphate buffer. The conjugate was purified by high performance liquid chromatography and characterized by mass spectrometry (see e.g., FIG. 2). The purified DOTA-ECL1i was radiolabeled with $^{64}$Cu (t$_{1/2}$=12.7 h, β$^+$=0.653 Mev (17.8%), β$^-$=0.579 Mev (38.4%)) ($^{64}$Cu-DOTA-ECL1i) for PET imaging.

Here, it has been shown that a chelator (e.g., 2,2',2''-(10-(2-((2-(2,5-dioxo-2,5-dihydro-1H-pyrrol-1-yl)ethyl)amino)-2-oxoethyl)-1,4,7,10-tetraazacyclododecane-1,4,7-triyl)triacetic acid (Maleimido-mono-amide-DOTA)) was conjugated to cysteine residue of a CCR2 binding peptide (DOTA-ECL1i) in pH 7.4 phosphate buffer (see e.g., FIG. 1). The conjugate was purified by high performance liquid chromatography and characterized by mass spectrometry. The purified DOTA-ECL1i was radiolabeled with $^{64}$Cu (t1/2=12.7 h, β+=0.653 Mev (17.8%), β-=0.579 Mev (38.4%)) ($^{64}$Cu-DOTA-ECL1i) for PET imaging. It is contemplated that the peptide can be conjugated with any radiolabel and/or nanoparticle used for other imaging modalities (e.g., $^{13}$C, $^2$H, iron oxide for MRI).

Characterization of CuAuNCs and CuAuNCs-ECL1i.

The UV-Vis absorption spectra were recorded using a Cary 60 UV-Vis spectrometer (Agilent Technologies, Santa Clara, CA). The $^{64}$CuAuNCs and $^{64}$CuAuNCs-ECL1i were examined after radioactive decay using a Tecnai G2 F20 ST Transmission Electron Microscope (TEM) operated at 200 kV (FEI, Hillsboro, OR). The TEM image showed that decayed CuAuNCs-ECL1i had a uniform size of 2.2±0.6 nm. The hydrodynamic size determined by dynamic light scattering (NanoZS, Malvern, Worcestershire, UK) showed a narrow size distribution of 5.0±0.5 nm with the zeta potential as −6.7±1.5 mV.

Flow Cytometry.

Lung tissue was cut into small pieces and digested by placement into a RPMI 1640 solution containing Type 2 collagenase (1 mg/mL) (Worthington Biochemical Corporation, Lakewood, NJ) and 10 U/mL DNase (Sigma, St. Louis, MO) at 37° C. for 60 min. The digested tissue was then passed through a 70-μm cell strainer and treated with ACK lysing buffer. Cells were stained with fluorochrome-labeled anti-CD45.2 (clone 104, eBioscience, San Diego, CA), anti-CD45.1 (clone A20, BD Biosciences, San Jose, CA), anti-CD11b (clone M1/70, BioLegend, San Diego, CA), anti-Ly6C (clone AL-21, BD Biosciences), anti-CCR2 (clone 575301, R&D Systems, Minneapolis, MN) and isotype control antibodies.

Biodistribution Studies.

C57BL/6 mice were used for the biodistribution studies. About 10 μCi of $^{64}$Cu-DOTA-ECL1i in 100 μL saline (APP pharmaceuticals, Schaumburg, IL) were injected via the tail vein. The mice were anesthetized with inhaled isoflurane and re-anesthetized before euthanasia by cervical dislocation at each time point (1 hour after injection, n=4/group). Organs of interest were collected, weighed and counted in a Beckman 8000 gamma counter (Beckman, Fullterton, CA). Standards were prepared and measured along with the samples to calculate the percentage of the injected dose per gram of tissue (% ID/gram).

Real-Time PCR Assay.

RNA isolated from transplanted mouse lung specimens (right-host lung, left-transplanted graft) was used for real-time RT-PCR. Tissue RNA was isolated using Nucleospin RNA kits (Macherey-Nagel; Bethlehem, PA) per the manufacturer's instruction. Reverse transcription reactions used 1 μg of total RNA, random hexamer priming, and Superscript II reverse transcriptase (Invitrogen). Expression of CCR2 and glyceraldehyde 3-phosphate dehydrogenase (GAPDH) were determined using Taqman assays (Invitrogen) and an Eco™ Real-Time PCR System (Illumina, San Diego, CA) in duplicate in 48-well plates. PCR cycling conditions were as follows: 50° C. for 2 min, 95° C. for 21 s, and 60° C. for 20 s. GAPDH expression was used as a comparator using AA Ct calculations.

REFERENCES FOR EXAMPLE 1

1. Kreisel D, Krupnick A S, Puri V, Guthrie T J, Trulock E P, Meyers B F et al. Short- and long-term outcomes of 1000 adult lung transplant recipients at a single center. J Thorac Cardiovasc Surg 2011; 141(1):215-222.
2. Daud S A, Yusen R D, Meyers B F, Chakinala M M, Walter M J, Aloush A A et al. Impact of immediate primary lung allograft dysfunction on bronchiolitis obliterans syndrome. Am J Respir Crit Care Med 2007; 175(5):507-513.
3. Kreisel D, Sugimoto S, Zhu J, Nava R, Li W, Okazaki M et al. Emergency granulopoiesis promotes neutrophil-dendritic cell encounters that prevent mouse lung allograft acceptance. Blood 2011; 118(23):6172-6182.
4. Kreisel D, Nava R G, Li W, Zinselmeyer B H, Wang B, Lai J et al. In vivo two-photon imaging reveals monocyte-dependent neutrophil extravasation during pulmonary inflammation. Proc Natl Acad Sci USA 2010; 107(42): 18073-18078.
5. Wang B, Zinselmeyer B H, Runnels H A, LaBranche T P, Morton P A, Kreisel D et al. In vivo imaging implicates CCR2(+) monocytes as regulators of neutrophil recruitment during arthritis. Cell Immunol 2012; 278(1-2):103-112.
6. Li L, Huang L, Sung S S, Vergis A L, Rosin D L, Rose C E, Jr. et al. The chemokine receptors CCR2 and CX3CR1 mediate monocyte/macrophage trafficking in kidney ischemia-reperfusion injury. Kidney Int 2008; 74(12):1526-1537.
7. Liehn E A, Piccinini A M, Koenen R R, Soehnlein O, Adage T, Fatu R et al. A new monocyte chemotactic protein-1/chemokine CC motif ligand-2 competitor limiting neointima formation and myocardial ischemia/reperfusion injury in mice. J Am Coll Cardiol 2010; 56(22): 1847-1857.
8. Dimitrijevic O B, Stamatovic S M, Keep R F, Andjelkovic A V. Absence of the chemokine receptor CCR2 protects against cerebral ischemia/reperfusion injury in mice. Stroke 2007; 38(4):1345-1353.
9. Majmudar M D, Keliher E J, Heidt T, Leuschner F, Truelove J, Sena B F et al. Monocyte-directed RNAi targeting CCR2 improves infarct healing in atherosclerosis-prone mice. Circulation 2013; 127(20):2038-2046.
10. Pienta K J, Machiels J P, Schrijvers D, Alekseev B, Shkolnik M, Crabb S J et al. Phase 2 study of carlumab (CNTO 888), a human monoclonal antibody against CC-chemokine ligand 2 (CCL2), in metastatic castration-resistant prostate cancer. Investigational new drugs 2013; 31(3):760-768.
11. Vergunst C E, Gerlag D M, Lopatinskaya L, Klareskog L, Smith M D, van den Bosch F et al. Modulation of CCR2 in rheumatoid arthritis: a double-blind, randomized, placebo-controlled clinical trial. Arthritis and rheumatism 2008; 58(7):1931-1939.
12. Lockhart A C, Liu Y, Dehdashti F, Laforest R, Picus J, Frye J et al. Phase 1 Evaluation of [Cu]DOTA-Patritumab to Assess Dosimetry, Apparent Receptor Occupancy, and Safety in Subjects with Advanced Solid Tumors. Mol Imaging Biol 2015.
13. Okazaki M, Krupnick A S, Kornfeld C G, Lai J M, Ritter J H, Richardson S B et al. A mouse model of orthotopic vascularized aerated lung transplantation. Am J Transplant 2007; 7(6):1672-1679.
14. Liu Y, Pierce R, Luehmann H P, Sharp T L, Welch M J. PET imaging of chemokine receptors in vascular injury-accelerated atherosclerosis. J Nucl Med 2013; 54(7): 1135-1141.
15. Jones H A, Donovan T, Goddard M J, McNeil K, Atkinson C, Clark J C et al. Use of 18FDG-pet to discriminate between infection and rejection in lung transplant recipients. Transplantation 2004; 77(9):1462-1464.
16. Liu Y, Pressly E D, Abendschein D R, Hawker C J, Woodard G E, Woodard P K et al. Targeting angiogenesis using a C-type atrial natriuretic factor-conjugated nanoprobe and PET. J Nucl Med 2011; 52(12):1956-1963.
17. Zhao Y, Sultan D, Detering L, Luehmann H, Liu Y. Facile synthesis, pharmacokinetic and systemic clearance evaluation, and positron emission tomography cancer imaging of (6)(4)Cu—Au alloy nanoclusters. Nanoscale 2014; 6(22):13501-13509.
18. Chen D L, Wang X, Yamamoto S, Carpenter D, Engle J T, Li W et al. Increased T cell glucose uptake reflects acute rejection in lung grafts. Am J Transplant 2013; 13(10):2540-2549.
19. Shah R J, Diamond J M, Lederer D J, Arcasoy S M, Cantu E M, Demissie E J et al. Plasma monocyte chemotactic protein-1 levels at 24 hours are a biomarker of primary graft dysfunction after lung transplantation. Transl Res 2012; 160(6):435-442.
20. Bharat A, Kuo E, Steward N, Aloush A, Hachem R, Trulock E P et al. Immunological link between primary graft dysfunction and chronic lung allograft rejection. Ann Thorac Surg 2008; 86(1):189-195; discussion 196-187.
21. Hoffman S A, Wang L, Shah C V, Ahya V N, Pochettino A, Olthoff K et al. Plasma cytokines and chemokines in primary graft dysfunction post-lung transplantation. Am J Transplant 2009; 9(2):389-396.
22. Eriksson O, Eich T, Sundin A, Tibell A, Tufveson G, Andersson H et al. Positron emission tomography in clinical islet transplantation. Am J Transplant 2009; 9(12): 2816-2824.
23. Daly K P, Dearling J L, Seto T, Dunning P, Fahey F, Packard A B et al. Use of [18F]FDG Positron Emission Tomography to Monitor the Development of Cardiac Allograft Rejection. Transplantation 2015; 99(9):e132-139.
24. Sharif-Paghaleh E, Yap M L, Meader L L, Chuamsaamarkkee K, Kampmeier F, Badar A et al. Noninvasive Imaging of Activated Complement in Ischemia-Reperfusion Injury Post-Cardiac Transplant. Am J Transplant 2015; 15(9):2483-2490.
25. Belperio J A, Keane M P, Burdick M D, Lynch J P, 3rd, Xue Y Y, Berlin A et al. Critical role for the chemokine MCP-1/CCR2 in the pathogenesis of bronchiolitis obliterans syndrome. J Clin Invest 2001; 108(4):547-556.
26. Leuschner F, Dutta P, Gorbatov R, Novobrantseva T I, Donahoe J S, Courties G et al. Therapeutic siRNA silencing in inflammatory monocytes in mice. Nat Biotechnol 2011; 29(11):1005-1010.
27. Auvynet C, Baudesson de Chanville C, Dorgham K, Piesse C, Pouchy C, Carlier L et al. ECL1i, d(LGT-FLKC), a novel small peptide that specifically inhibits CCL2-dependent migration. The FASEB Journal 2016.
28. Gelman A E, Okazaki M, Sugimoto S, Li W, Kornfeld C G, Lai J et al. CCR2 regulates monocyte recruitment as well as CD4 T1 allorecognition after lung transplantation. Am J Transplant 2010; 10(5):1189-1199.

29. Serbina N V, Pamer E G. Monocyte emigration from bone marrow during bacterial infection requires signals mediated by chemokine receptor CCR2. Nat Immunol 2006; 7(3):311-317.
30. Swirski F K, Nahrendorf M, Etzrodt M, Wildgruber M, Cortez-Retamozo V, Panizzi P et al. Identification of splenic reservoir monocytes and their deployment to inflammatory sites. Science 2009; 325(5940):612-616.

Lui et al. PET-based Imaging of Chemokine Receptor 2 in Experimental and Disease related Lung Inflammation Radiology, Volume 283: Number 3—June 2017

Example 2: Pet-Based Imaging of Chemokine Receptor-2 in Experimental and Disease-Related Lung Inflammation The following example describes the characterization of a chemokine receptor-2 (CCR2) binding peptide adapted for use as a positron emission tomography (PET) radiotracer for non-invasive detection of lung inflammation in a mouse model of lung injury and in human tissues from subjects with lung disease.

In particular, PET images obtained in mouse lungs following injury with LPS, was significantly greater than the saline control group (mean % ID/g=4.43 vs. 0.99; P<0.001). PET signal was significantly diminished with blocking studies using non-radiolabeled ECL1i in excess (mean % ID/g=0.63; P<0.001) and in CCR2-deficient mice (mean % ID/g=0.39; P<0.001). The ECL1i signal was associated with an elevated level of mouse lung monocytes. COPD lung tissue displayed significantly elevated CCR2 levels compared to non-diseased tissue (median 12.8 vs. 1.2 percent cells/sample; P=0.002), which was detected by $^{64}$Cu-DOTA-ECL1i using autoradiography. In summary, $^{64}$Cu-DOTA-ECL1i performed as a promising tool for PET-based detection of CCR2-directed inflammation in an animal model and in human tissues as a step toward clinical translation.

Lung inflammation is a result of the recruitment of inflammatory cells along chemokine gradients, guided by their cognate receptors (1,2). In some lung conditions, patterns of inflammatory cell recruitment can be used to diagnose diseases and direct therapeutic decisions (e.g., asthma, eosinophilic pneumonia) (3,4). However, developing a detection strategy for identifying immune population signatures has been difficult since many inflammatory cells are localized within the lung parenchyma, out of reach of conventional diagnostic tools. Consequently, understanding the contribution of immune cell subsets in disease is limited and the clinical development of specific antagonists for lung disease is stalled. Non-invasive detection could ultimately be used to characterize an individual's molecular status, disease activity and response to established or new therapies (5).

Chemokine (C-C Motif) ligand 2 (CCL2; also called Monocyte chemoattractant protein-1, MCP-1) and its receptor chemokine (C-C motif) receptor 2 (CCR2) are often elevated in lung tissue of subjects with pulmonary diseases (6-10). CCR2 is a surface receptor found on most inflammatory monocytes and macrophages, as well as some dendritic cells and lymphocytes (1,2). CCR2$^+$ inflammatory monocytes are essential early responding immune cells, and excessive or prolonged recruitment impairs resolution of inflammation and propagates disease progression (3,11,12). Experimentally, endotoxin triggers CCR2-dependent migration of monocytes and macrophages to the lung and influences subsequent neutrophil recruitment (13-15). CCR2$^+$ signaling in monocytes provides a secondary source of proinflammatory cytokines and proteases, contributing to lung injury (12,16). Recruitment of CCR2-dependent leukocytes impacts the magnitude and duration of acute respiratory distress syndrome (17) and elevated numbers of CCR2$^+$ monocytes are associated with ongoing inflammation in chronic obstructive pulmonary disease (COPD) (6,7), supporting the use of CCR2$^+$ cells as a marker of disease activity. CCR2$^+$ cells may also serve as a therapeutic target since CCR2 blockade improves outcome in animal models of disease and has steered considerable effort toward the development and testing CCR2 antagonists (18,19).

We have recently described the use of a peptide that binds the first extracellular loop (ECL1i) of CCR2 (20) for non-invasive imaging for initial studies in a lung ischemia-reperfusion model (21), but the generalizability to common inflammatory conditions and the activity in human disease tissue is unknown. The goal of this study is to further characterize the ECL1i-based PET radiotracer for the non-invasive detection of monocyte-related inflammation in a mouse model of endotoxin-induced lung injury and in human lung tissue.

Materials and Methods.

The study had institutional Animal and Human Studies Committees approval and patient consent. A 7-amino acid CCR2 binding peptide (ECL1i) was conjugated to 1,4,7,10-tetraazacyclododecane-1,4,7,10-tetraacetic acid (DOTA) and labeled with copper-64 ($^{64}$Cu) or fluorescent dye. Lung inflammation was induced by intratracheal administration of lipopolysaccharide (LPS) in wild-type (n=19) and CCR2-deficient mice (n=4), and compared to wild-type mice given control saline (n=5) by PET imaging performed following intravenous injection of $^{64}$Cu-DOTA-ECL1i. Lung immune cells and those binding fluorescently labeled ECL1i in vivo were detected by flow cytometry. Lung inflammation in tissue from subjects with non-diseased lungs donated for lung transplantation (n=11) and chronic obstructive pulmonary disease (COPD) who were undergoing lung transplant (N=16) was evaluated for CCR2 by immunostaining and autoradiography (n=6, COPD) with $^{64}$Cu-DOTA-ECL1i. Groups were compared using ANOVA, Mann Whitney U- or t-tests.

Human Tissues.

The Institutional Review Board approved these studies. Human COPD lung tissue samples were obtained at the time of lung transplantation from individuals who provided consent prior to surgery (n=16). All patients undergoing lung transplantation had very severe COPD by clinical criteria. Non-diseased, donated lungs were those not usable for transplantation or tissues provided after lungs were downsized (n=11). Samples were prospectively collected between 2005 and 2013, de-identified and stored prior to use (TABLE 1). Samples were selected for analysis based on tissue availability without pre-selection for specific clinical features.

TABLE 1

Donor and COPD subjects providing lung tissue for CCR2 immunostaining.

| ID # | Disease | Age | Gender | Race | Smoker | FEV1/FVC | FEV1 % pred | Mean % CCR2+ cells per sample |
|---|---|---|---|---|---|---|---|---|
| DONOR | | | | | | | | |
| D1 | | 33 | M | W | N | ND | ND | 1.66 |
| D2 | | 19 | M | W | N | ND | ND | 0.53 |
| D3 | | 23 | M | W | N | ND | ND | 0.19 |
| D4 | | 15 | F | B | N | ND | ND | 2.09 |
| D5 | | 17 | M | W | N | ND | ND | 23.97 |
| D6 | | 14 | M | W | N | ND | ND | 1.16 |
| D7 | | 17 | M | W | N | ND | ND | 0.57 |
| D8 | | 52 | M | W | N | ND | ND | 0.41 |
| D9 | | 54 | M | W | N | ND | ND | 4.52 |
| D10 | | 19 | M | W | N | ND | ND | 6.52 |
| D11 | | 62 | M | W | N | ND | ND | 9.30 |
| n = 11 | | | | | | | | |
| Median | | 19 | | | | | | 1.66 |
| Range | | 14-62 | | | | | | 0.19-23.97 |
| COPD | | | | | | | | |
| C1 | COPD | 58 | M | W | Former | 0.21 | 17 | 8.49 |
| C2 | COPD | 51 | M | W | Former | 0.15 | 14 | 18.65 |
| C3 | COPD | 58 | F | W | Former | 0.21 | 24 | 9.51 |
| C4 | COPD | 54 | M | W | Former | 0.31 | 17 | 9.19 |
| C5 | COPD | 43 | M | W | Former | 0.44 | 22 | 1.61 |
| C6 | COPD | 61 | F | W | Former | 0.36 | 18 | 5.35 |
| C7 | COPD/A1E | 35 | F | W | Former | 0.24 | 17 | 13.55 |
| C8 | COPD | 54 | F | W | Former | 0.25 | 16 | 13.58 |
| C9 | COPD | 62 | M | W | Former | 0.22 | 18 | 19.70 |
| C10 | COPD | 57 | F | W | Former | 0.25 | 16 | 6.22 |
| C11 | COPD | 60 | F | W | Former | 0.34 | 20 | 11.78 |
| C12 | COPD | 57 | F | W | Former | 0.32 | 30 | 22.03 |
| C13 | COPD | 54 | M | W | Former | 0.17 | 16 | 22.25 |
| C14 | COPD | 63 | F | W | Former | 0.28 | 12 | 21.71 |
| C15 | COPD/A1E | 52 | M | W | Former | 0.27 | 20 | 24.11 |
| C16 | COPD/A1E | 58 | F | W | Former | 0.25 | 17 | 12.09 |
| n = 16 | | | | | | | | |
| Median | | 57 | | | | 0.25 | 17 | 12.82 |
| Range | | 35-63 | | | | 0.15-0.44 | 12-30 | 1.16-24.11 |

Abbreviations: M, male; F, female; W, white; B, black; COPD, chronic obstructive lung disease; A1E, Alpha-1-antitrypsin deficiency; FEV1/FVC, ratio of forced expiratory volume at 1 sec to forced vital capacity; FEV1 % pred, predicted percent FEV1; ND, not determined.

Mice

Figure 19A:
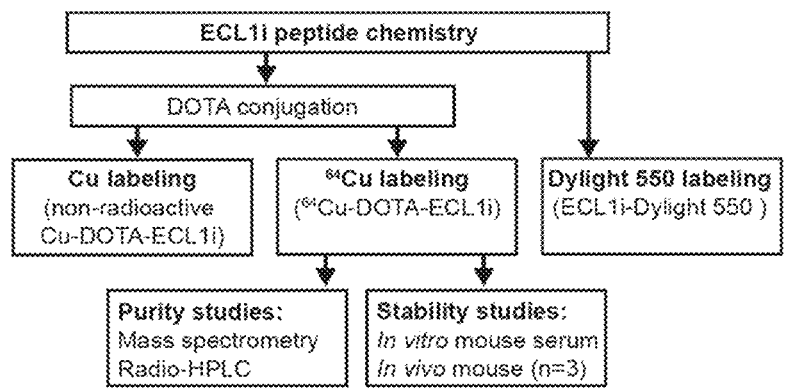
FIG. 19A-FIG. 19C is a series of flow charts describing the study design of CCR2 imaging using the ECL1i peptide.
Figure 19B:
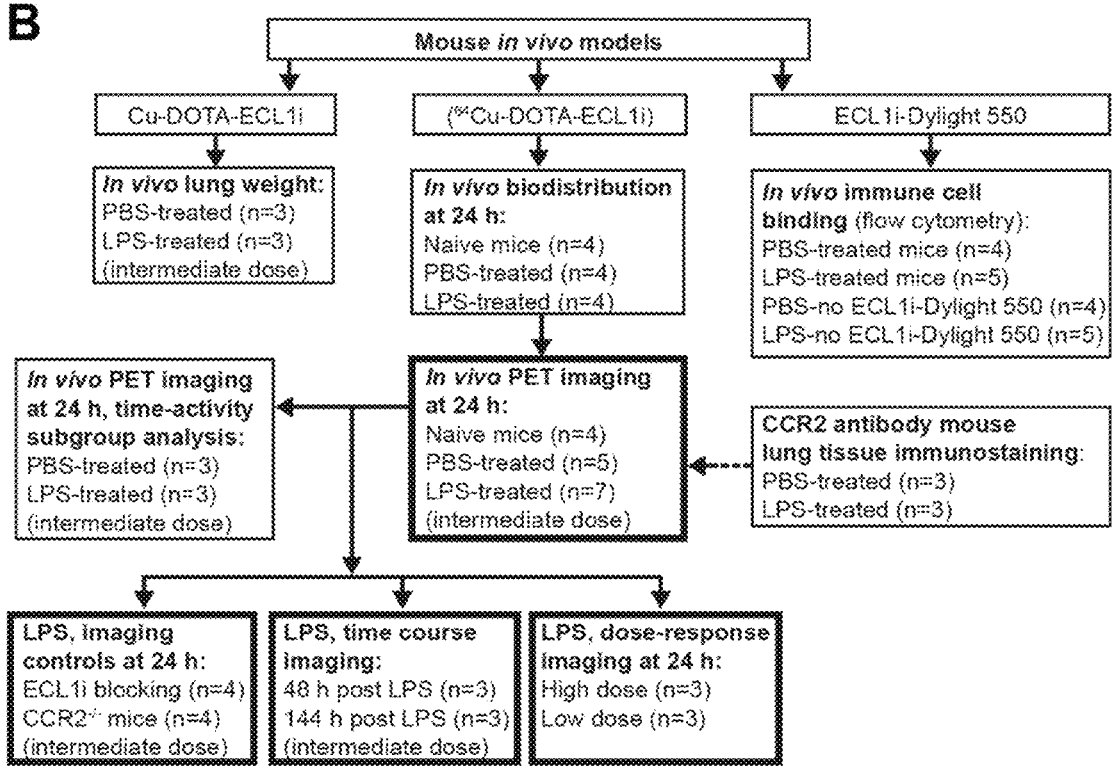
Figure 19C:
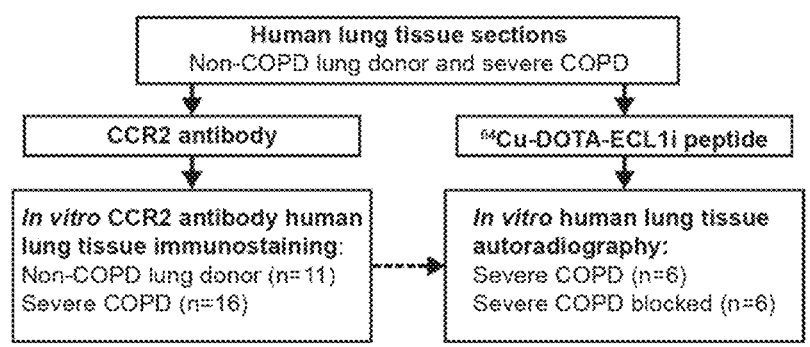

The Institutional Animal Care and Use Committee approved these studies. Wild type (n=77) and CCR2-deficient (CCR2$^{-/-}$, n=4) mice (C57BL6/J strain) were 8 to 12 weeks of age, of both sexes and approximately 25 g in weight. Mice were used for radiotracer stability studies (n=3) and lung injury studies that included: immunostaining for CCR2 (n=6), in vivo immune cell peptide binding (n=18), lung water weight measurements (n=6), in vivo biodistribution (n=12) and PET/CT imaging (n=36). For the lung injury studies, mice were not treated (naive, n=8), administered intratracheal vehicle control, phosphate buffered saline (PBS, 1 μL/g, n=26) or lipopolysaccharide (LPS, endotoxin, E. coli strain 055:B5, Sigma-Aldrich, St. Louis, MO), at a dose of 2.5 μg/g (n=44), "high" dose, 10 μg/g (n=3), or "low" dose, 0.5 μg/g (n=3) LPS. All CCR2-deficient mice were administered an LPS dose of 2.5 μg/g. Lung water was quantified using wet-to-dry weight ratios in PBS- or intermediate dose LPS-treated mice (n=3/group). Lungs were resected and weighted immediately, then compared to weights obtained after drying at 65° C. for 48 h. The study flow is shown in FIG. 19.

Synthesis, Labeling, and Stability of ECL1i.

The ECL1i peptide (LGTFLKC) was synthesized from D-form amino acids by CPC Scientific (Sunnyvale, CA). DOTA-ECL1i was prepared by conjugating 1,4,7,10-tetraazacyclododecane-1,4,7,10-tetraacetic acid (DOTA) that was modified as maleimido-mono-amide-DOTA (1.573 mg, 0.2 μmol; Macrocyclics, Dallas, TX) to the cysteine residue of ECL1i, using established methods (22). The crude conjugate was purified by high performance liquid chromatography (HPLC) to reach 99% chemical purity and verified by mass spectrometry. Copper-64 ($^{64}$Cu) was selected as an initial radiolabel for ECL1i based on a high specific activity that enabled trace amount administration and provided a decisive PET signal if present, straightforward radiochemistry through the conjugation of the DOTA chelator on the peptide, on-site availability, and prior experience with this radionuclide (22). The DOTA-ECL1i conjugate was radiolabeled with $^{64}$CuCl$_2$ as described (22). Copper-64-DOTA-ECL1i ($^{64}$Cu-DOTA-ECL1i) was tested for stability by incubation in mouse serum at 37° C. for 1 h and in vivo, in blood and lung 1 h post injection (n=3), by radio-HPLC analysis. Maleimide-modified Dylight 550 (ThermoFisher Scientific, Waltham, MA) was conjugated to ECL1i on the cysteine residue following the same protocol for DOTA conjugation and purified by HPLC.

Biodistribution.

Mice (n=4/group) were naive, treated with intratracheal PBS or LPS and after 24 h injected with $^{64}$Cu-DOTA-ECL1i by tail vein as a bolus of 100 μL (3.7 MBq per mouse). After euthanasia, 1 h post-radiotracer injection, organs of interest were collected, weighed and assayed by gamma counter (Beckman, Brea, CA) as described (23). Standards were prepared and measured in parallel to calculate the percentage of the injected dose per gram of tissue (% ID/g).

PET/CT Imaging and Image Analysis.

Dynamic (0-60 min) PET and corresponding x-ray computed tomography (CT) images were acquired using cross-calibrated Inveon microPET/CT (Siemens, Malvern, PA) or Focus 220 PET (Concorde Microsystems, Knoxville, TN) scanners, immediately after the tail vein injection of $^{64}$Cu-DOTA-ECL1i (3.7 MBq per mouse) at 24, 48 and 144 h after LPS treatment. The organ uptake was calculated as percent injected dose per gram (% ID/g) of tissue in three-dimensional regions of interest (ROIs) from PET images without correction for partial volume effect using Inveon Research Workplace software (Siemens) (23). Time-activity curves were calculated from the ROIs from PET images obtained in a subgroup (n=3/group) of the PBS- and LPS-treated mice undergoing imaging at 24 h. Competitive PET blocking studies were performed in the LPS mouse model with co-injection of an excess amount of non-radiolabeled ECL1i (900.9 pmol) and $^{64}$Cu-DOTA-ECL1i (1.8 pmol) (ECL1i: $^{64}$Cu-DOTA-ECL1i molar ratio=500:1) followed by a 0-60 minute dynamic scan. PET/CT images of naive (n=4) and PBS-treated (n=5) mice at 24 h were used as controls for all LPS-treatment studies performed at 24 h including ECL1i blocking studies (n=4), CCR2$^{-/-}$ mice (n=4), low- (n=3) and high-dose LPS (n=3), as well as images obtained at 48 (n=3) and 144 (n=3) h post-LPS.

Flow Cytometry.

Mice (n=4 PBS, n=5 LPS) delivered intratracheal PBS or LPS, and 24 hours later were injected intravenously with ECL1i labeled with Dylight 550 (100 μg) to determine the type of inflammatory cell binding ECL1i. Other mice were treated in parallel but not given ECL1i-Dylight 550 (n=4 PBS, n=5 LPS). One h post-injection, a single cell suspension was produced from the lungs, immunostained with immune cell markers (TABLE 2) and analyzed by flow cytometry.

TABLE 2

Antibodies used to phenotype cells by flow cytometry

| Cell Type | AF 488 | PerCP/Cy5.5 PE/Cy7 | APC AF 647 |
|---|---|---|---|
| Neutrophil | CD45.2+ | Ly6G$^{Hi}$ | GR-1$^{Hi}$ |
| Monocyte | CD45.2+ | Ly6G$^{Lo}$ | Ly6C$^{Hi}$ |
| Macrophage | CD45.2+ | CD11c$^{Hi}$ | CD11b$^{Lo}$ |
| Dendritic Cell | CD45.2+ | CD11c$^{Hi}$ | CD11b$^{Hi}$ |
| T Cell | CD45.2+ | — | CD90.2 (Thy 1.2)$^{Hi}$ |
| B Cell | CD45.2+ | — | CD19$^{Hi}$ |

Immunostaining and Microscopy.

Tissue sections were immunostained using a CCR2 monoclonal antibody (Novus Biologicals, Littleton, CO) in mouse and human tissue (n=6 mice, n=27 human). In each human tissue section, CCR2-staining cells were assessed from five photomicrographs, acquired at 200× magnification. Images were analyzed by investigators who were unfamiliar with the hypothesis. The percent of CCR2 expression was determined as a ratio of the area of CCR2 signal relative to DAPI using ImageJ software v1.50. Details are provided in the Supplement.

Autoradiography.

Fixed human lung tissue sections that were deparaffinized and hydrated in PBS were incubated with $^{64}$Cu-DOTA-ECL1i for 5 min (n=4 donor, n=6 COPD). Blocking studies were performed in lung sections from subjects with COPD demonstrating levels of CCR2 immunostaining above the median (n=6) by co-incubation with 500-fold non-radioactive ECL1i. Slides were washed 30 times with water then placed in an instant imager (Packard, Meriden, CT) for 30 minutes. Images were post-processed using Imager Software (Packard, Meriden, CT) and the percentage of blocked signal was calculated.

Statistical Methods.

Data were analyzed using Prism (version 6.07, Graphpad, La Jolla, CA). Differences between groups were compared using the two-tailed Student's t-test. Means of non-parametric data from human samples was compared using the Mann-Whitney U test. Multiple means were compared using a one- or two-way ANOVA with Tukey's test. Significance was established as $p<0.05$.

$^{64}$Cu-DOTA-ECL1i In Vivo Stability Study.

$^{64}$Cu-DOTA-ECL1i (3.7 MBq in 100 μL saline) was injected into the tail vein of mice. At 1 h post injection, mice were euthanized and blood was collected in a glass tube containing acid citrate dextrose. The plasma was separated from cells by centrifugation then analyzed by HPLC (Ultimate 3000, Dionex, Sunnyvale, CA). The HLPC instrument that was equipped with a UV/VIS detector (Dionex, Sunnyvale, CA), a radioactivity detector (B-FC-3200; BioScan Inc., Poway, CA) and a C-18 column (5 mm, 4.6×220 mm; Perkin Elmer, Waltham, MA) (36). Similarly, mouse lung was harvested one hour after radiotracer injection and rinsed with PBS (5 mL, three times) prior to cell disruption using a probe sonicator (Sonifier 185 cell disruptor, Branson, Danbury, CT) for 30 seconds. The supernatant was isolated by centrifugation and analyzed by HPLC. The eluate was separated by 1 mL fractions and counted in a well gamma counter (Wallac Wizard 1470, Perkin Elmer, Waltham, MA).

Mouse Lung Injury Model.

Wild-type mice in the C57B/6J background and CCR2-deficient mice (CCR2$^{-/-}$, No. 004999) were obtained from the Jackson Labs (Bar Harbor, ME). CCR2-deficient mice were backcrossed into the C57B/6J background. Mice, 8 to 12 weeks of age, of both sexes and weighing approximately 25 g, were used. Mice were anesthetized by administering a combination of ketamine HCl, 100 mg/kg and xylazine HCl. 15 mg/kg, by intraperitoneal injection. To deliver PBS control vehicle or LPS into the lung, the trachea was surgically isolated and cannulated with a 22 gauge, 1" catheter (Exel Safelet, ThermoFisher Scientific, Waltham, MA). Mice were administered phosphate buffered saline (PBS, 1 μL/g) or lipopolysaccharide at a dose of 2.5 μL/g (LPS, endotoxin, E. coli strain 055:B5, Sigma-Aldrich, St. Louis, MO). Other mice were administered an LPS "high" dose, 10 μL/g, or "low" dose, 0.5 μg/g, using stock solutions of LPS created to inject a volume of 1 L/g. Intratracheal injection was over approximately 2 seconds, after which mice were kept warm and allowed to recover.

Flow Cytometry.

Mice delivered intratracheal PBS or LPS were injected intravenously with ECL1i labeled with Dylight 550, as with the radiolabeled probe, to determine the type of inflammatory cell binding ECL1i. For each experiment, animals treated with PBS or LPS were paired with a control not injected with ECL1i-Dylight 550 to determine the background signal. Lungs were removed from mice without flushing blood from the vasculature, minced on ice and digested in Roswell Park Memorial Institute (RPMI) 1640 medium containing Liberase TL 50 μg/mL (Roche, Indianapolis, IN) and deoxyribonuclease (DNAse) I, Type II, 20 U/mL (Sigma-Aldrich) at 37° C. for 60 min. The digested tissue was passed through a 70-μm sieve (Falcon 352350, Corning, Corning, NY) to create a single cell suspension, and then incubated in ACK Lysing Buffer (Lonza, Walkersville, MD) at room temperature to lyse red blood cells. After 5 minutes the sample was neutralized with FACS buffer (PBS with 2% fetal bovine serum) and centrifuged at 500 g for 8 minutes at 4° C. Cells were suspended in FACS buffer, counted by hemocytometer, and prepared for flow cytometry. Cells were immunostained with labeled antibodies (all from BioLegend, San Diego, CA, unless indicated) specific for mouse, including CD31 PerCP/Cy5.5, CD326 Alexa Fluor 488, CD45.2 Alexa Fluor 488, Gr-1 APC (eBioscience), Ly-6C APC, CD11c PE/Cy7, CD11b APC, CD90.2 (Thy-1.2) APC, Ly-6G PE/Cy7 (BD Pharmingen), and CD19 APC. Counts from 1 to $10 \times 10^4$ cells were collected for each sample on a FACSCalibur (Becton Dickinson), dual laser, flow cytometer using CellQuest Pro software (BD Biosciences), and analyzed using FlowJo software (Ashland, OR). Cell phenotype was determined by antibody binding shown in the TABLE 2. The mean fluorescent intensity was determined by calculating the geometric mean of Dylight 550 fluorescence of the cell types identified in ECL1i-Dylight 550-injected mice and subtracting the fluorescent background of the same cell types from similarly treated mice not injected with ECL1i-Dylight 550.

Immunostaining and Microscopy.

Tissue sections were fixed and processed for immunostaining as described (37). The monoclonal anti-CCR2 antibody (E68, Novus Biologicals, Littleton, CO) was used in mouse and human tissues. In mouse lung, the CCR2 antibody was detected using avidin-biotin amplification (Vectastain Elite ABC, Vector Laboratories, Burlingame, CA) and horseradish peroxidase (HRP) substrate 3, 3-diaminobenzidine (DAB), which produces a brown reaction product. Tissues were then counterstained blue with hematoxylin. In human tissues, the CCR2 antibody was detected with an Alexa Fluor 555 labeled secondary antibody (Molecular Probes, Carlsbad CA) and DNA was counterstained with 4', 6 diamidino-2-phenylindole (DAPI). Photomicroscopy was performed using a Leica DM5000 microscope and DFC7000T camera interfaced with LASX software (Leica Microscopy, Buffalo Grove, IL). Images were adjusted globally using Photoshop software (Adobe, San Jose, CA). In human tissue CCR2-staining cells were assayed from five representative photomicrographs from each tissue section. Images were acquired at 200× magnification and counted by investigators with expertise in cell biology blinded to the hypothesis (ZBN, 2 years of experience; JP, 25 years of experience, and SPG, 9 years of experience) that results are different between study groups and with experience in scoring these data. The CCR2 expression was calculated as a ratio of the area of CCR2 signal relative to DAPI determined using ImageJ software v1.50 to establish a threshold setting for positive staining cells (38). Once determined, values from the five representative images were from all samples were collected, analyzed by threshold, then averaged, all by a single investigator (ZBN). The percent of CCR2 positive cells in the donor and COPD groups were compared using the Mann-Whitney test. To further assess our findings, we also immunostained additional lung samples from different regions of the lung that were available for some individuals (n=2 donors, n=3 COPD). Typically, there was little variation in the level of $CCR2^+$ cells within the same specimen. In these cases, the mean percent $CCR2^+$ cell value was calculated and used for analysis.

$^{64}$Cu-DOTA-ECL1i Radiochemistry and Stability.

Figure 20A:
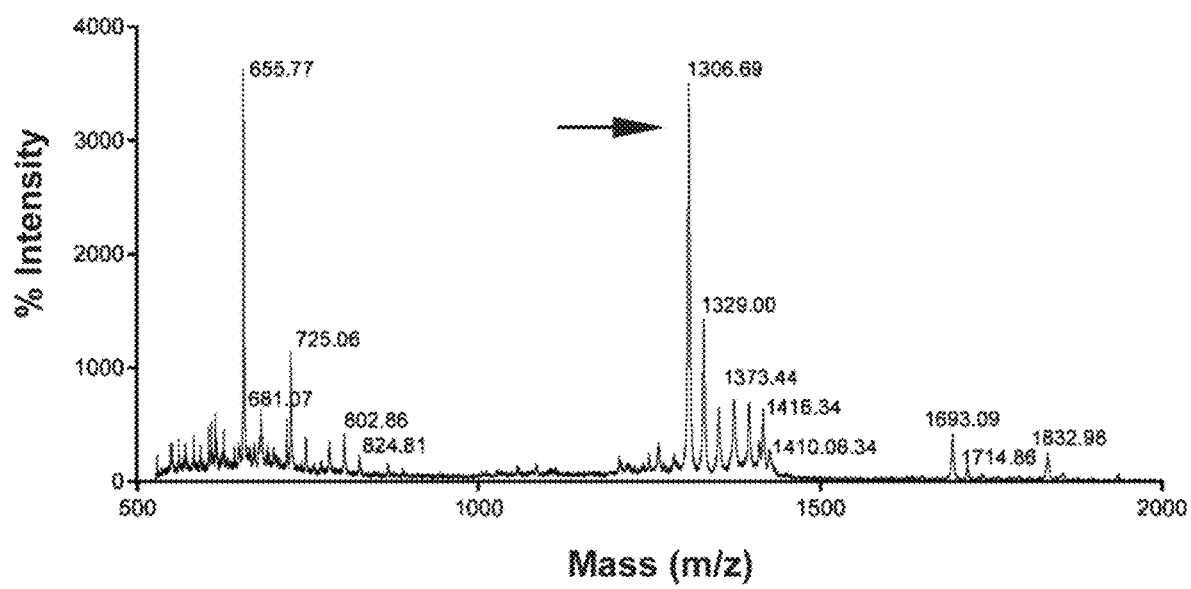
FIG. 20A-FIG. 20B is a series of spectra characterizing $^{64}$Cu-DOTA-ECL1i.
Figure 20B:
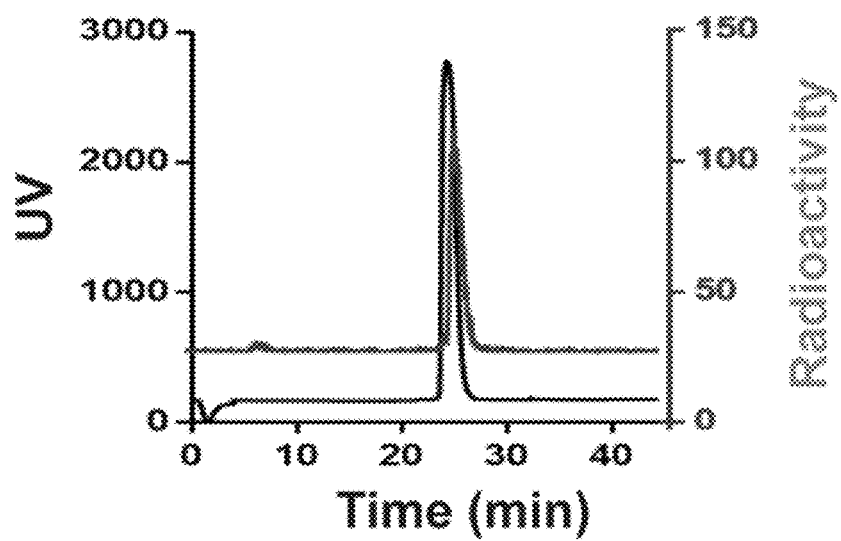
Figure 21:
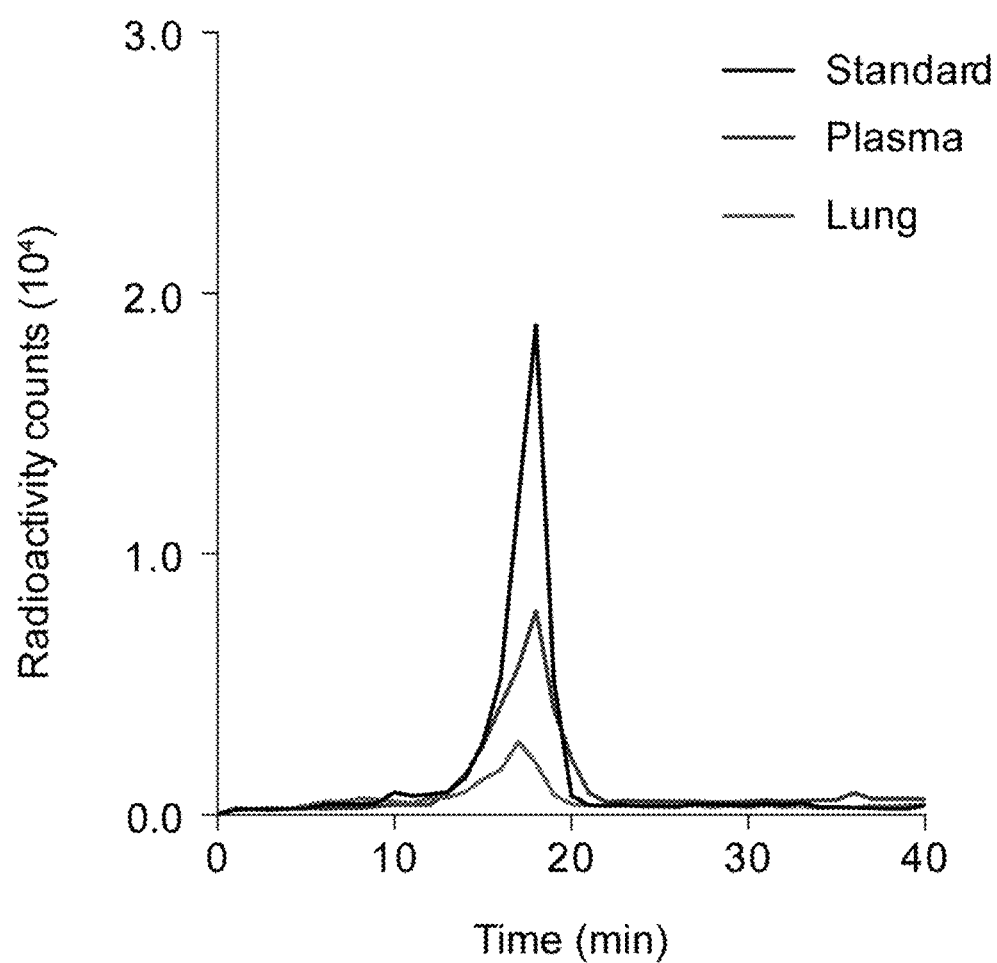
FIG. 21 is an HPLC spectrum showing in vivo stability of $^{64}$Cu-DOTA-ECL1i. The radiolabeled probe $^{64}$Cu-DOTA-ECL1i was analyzed by HPLC to determine the retention time. Shown are representative traces of $^{64}$Cu-DOTA-ECL1i as a standard (black), and samples obtained from naive, wild type mice injected intravenously with the radioprobe. After one h, plasma (blue) and the lung homogenate (red) was obtained and assayed by HPLC. Data are representative of n=3.

The mass spectrometry of the conjugate confirmed that one DOTA conjugated to one ECL1i peptide ($M^+$ calculated: 1306.65, observed: 1306.69) (see e.g., FIG. 20A). The radiochemical purity of $^{64}$Cu-DOTA-ECL1i used for animal studies was 98% or greater, confirmed by radio-HPLC (see e.g., FIG. 20B). The specific activity of $^{64}$Cu-DOTA-ECL1i was 55.5±1.11 mCi/nmol (n=20), enabling trace amounts (~70 pmol) to be injected for in vivo studies. $^{64}$Cu-DOTA-ECL1i was stable in mouse serum in vitro at 37° C. for 1 h (98.2±2.1%) and in vivo, in serum (96.5±1.1%) and lung (95.6±3.0%) recovered from naive mice 1 h post injection, using HPLC analyses and gamma counting (see e.g., FIG. 21).

Biodistribution of $^{64}$Cu-DOTA-ECL1i in the LPS Mouse Lung Injury Model.

Figures 22A, 22B:
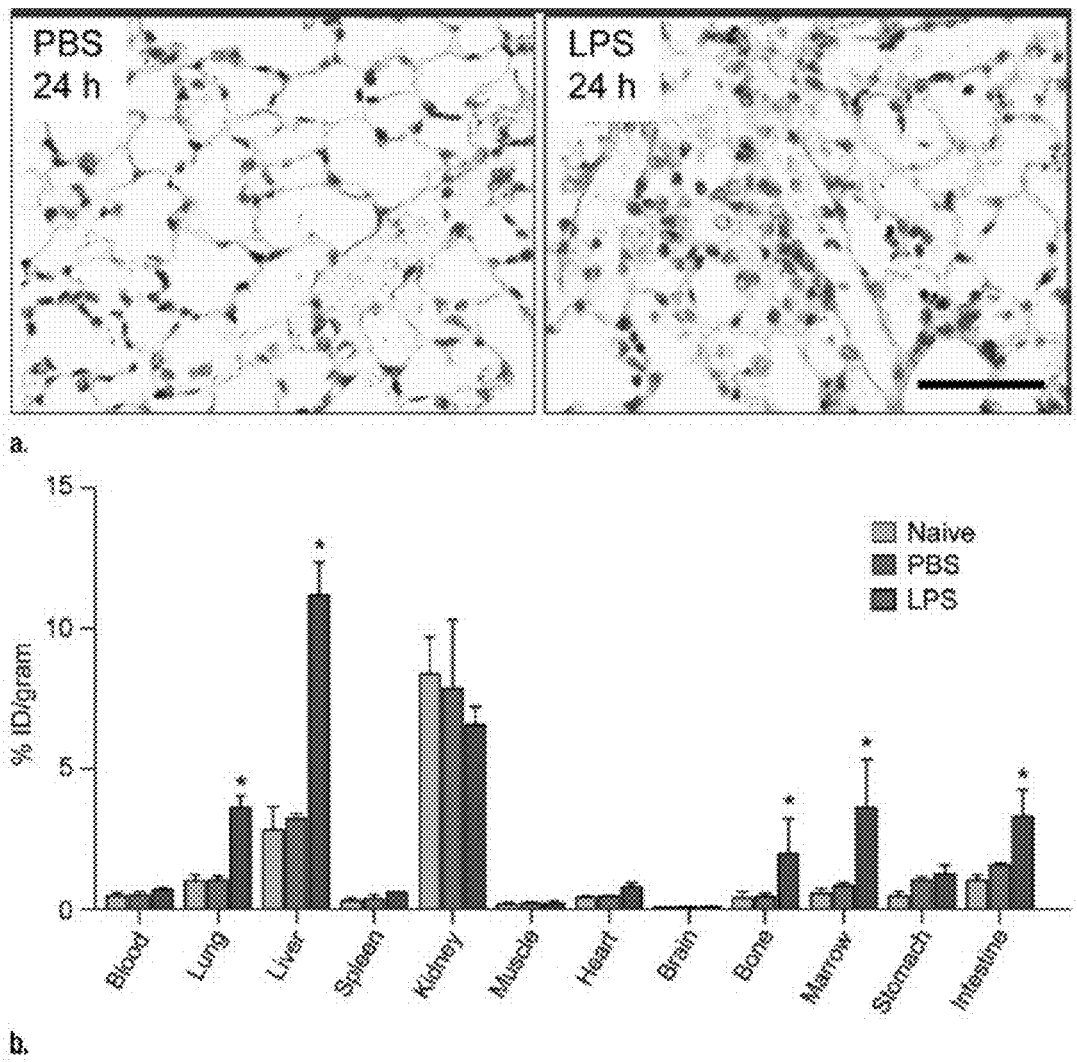
FIG. 22A-FIG. 22B is a series of images and a bar graph showing the biodistribution of $^{64}$Cu-DOTA-ECL1i in mice with lung injury. Mice were not treated (naive), or administered intratracheal PBS or LPS.

We assayed $^{64}$Cu-DOTA-ECL1i in a well-characterized lung injury model in which endotoxin (LPS) activates the accumulation of CCR2-expressing cells in the lung (13, 24). As expected, 24 h after intratracheal delivery of LPS, CCR2-expressing cells were detected in mouse lungs (see e.g., FIG. 22A). The in vivo pharmacokinetic evaluation of $^{64}$Cu-DOTA-ECL1i acquired 1 h following intravenous injection was compared in naive mice and 24 h after the delivery of intratracheal control vehicle PBS or LPS (see e.g., FIG. 22B). Accumulation of tracer in the lung of mice given LPS was 2.5 times higher than that in the PBS group, although there was no difference in blood retention. $^{64}$Cu-DOTA-ECL1i showed renal clearance as evidenced by the kidney accumulation in both groups. Liver and bone marrow uptake of $^{64}$Cu-DOTA-ECL1i in LPS-treated mice was significantly higher than the PBS-treated mice.

CCR2 Imaging in LPS Lung Injury.

Figure 23A:
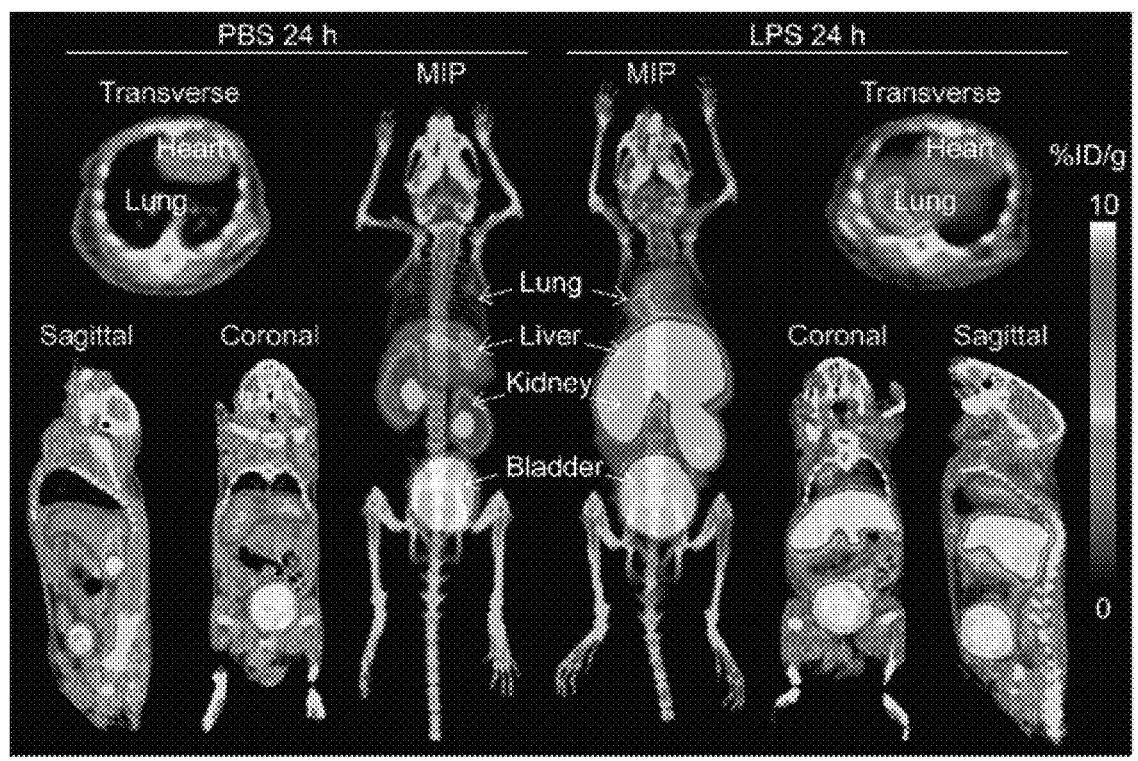
FIG. 23A-FIG. 23D is a series of images, a plot and bar graphs depicting PET imaging data of $^{64}$Cu-DOTA-ECL1i in mouse lung injury model. Mice were administered intratracheal PBS or LPS, followed by injection with i.v. $^{64}$Cu-DOTA-ECL1i.
Figure 23B:
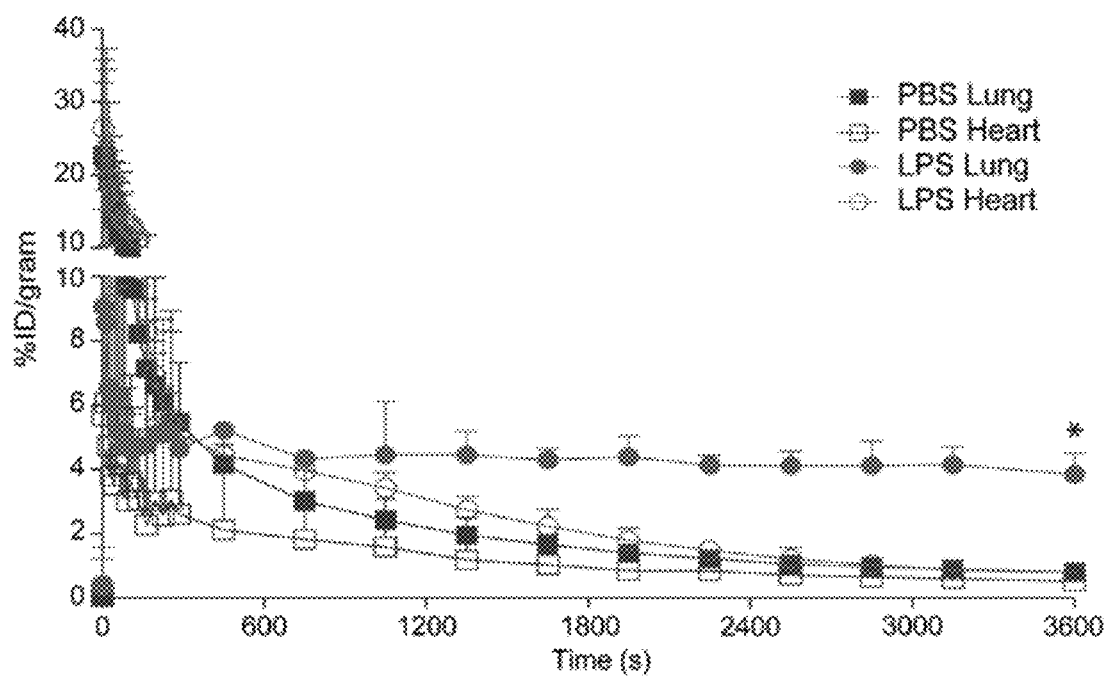
Figure 23C:
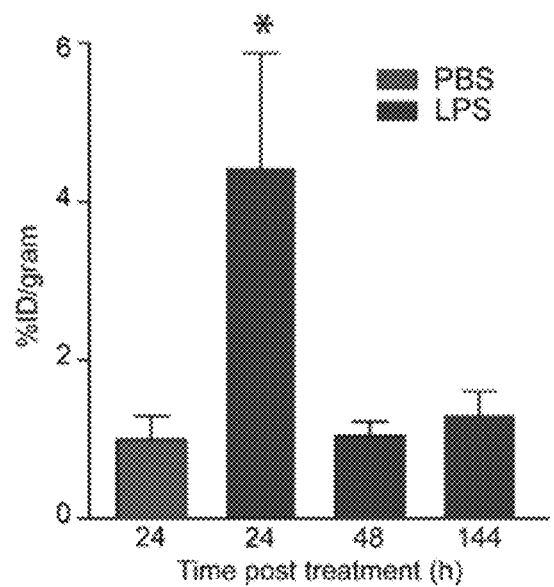
Figure 23D:
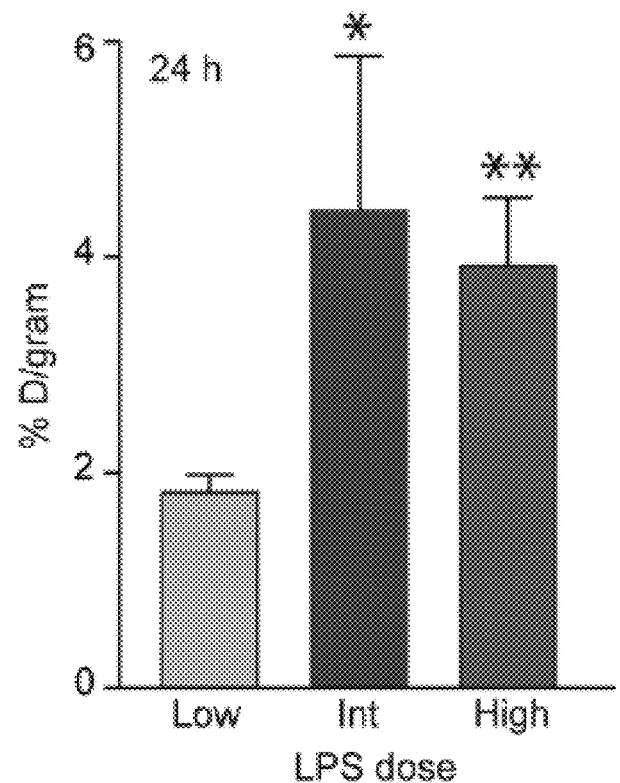

Based on the biodistribution studies, we administered intratracheal PBS or LPS and determined if intravenous $^{64}$Cu-DOTA-ECL1i could be used as a PET agent to image lung inflammation. Compared to PBS delivery, there was a prominent signal in the lungs of LPS-treated mice at 24 h (PBS mean % ID/g=0.99±0.29, n=5; LPS mean % ID/g=4.43±1.44, n=7; P<0.001) (see e.g., FIG. 23). Consistent with biodistribution studies, LPS also increased activity in the liver, and renal clearance was indicated by enhanced kidney and bladder activity in all mice. The time-activity curve acquired 24 h after injury demonstrated a higher and consistent accumulation of $^{64}$Cu-DOTA-ECL1i in the LPS-treated lung compared to the PBS control, which was significantly lower, and further diminished over the imaging period. $^{64}$Cu-DOTA-ECL1i uptake in the lung peaked at 24 h, followed by a loss of signal in mice injected and imaged at 48 h (mean % ID/g=1.04±0.17, n=5) or 144 h (mean % ID/g=1.29±0.32, n=5) post-LPS (see e.g., FIG. 23C). Mice were administered high and low doses of LPS to determine the sensitivity of $^{64}$Cu-DOTA-ECL1i detection by PET. The lung signal in mice administered low dose LPS (mean % ID/g=1.82±0.17, n=5) was decreased compared to treatment with intermediate and high doses (see e.g., FIG. 23D).

Figure 24A:
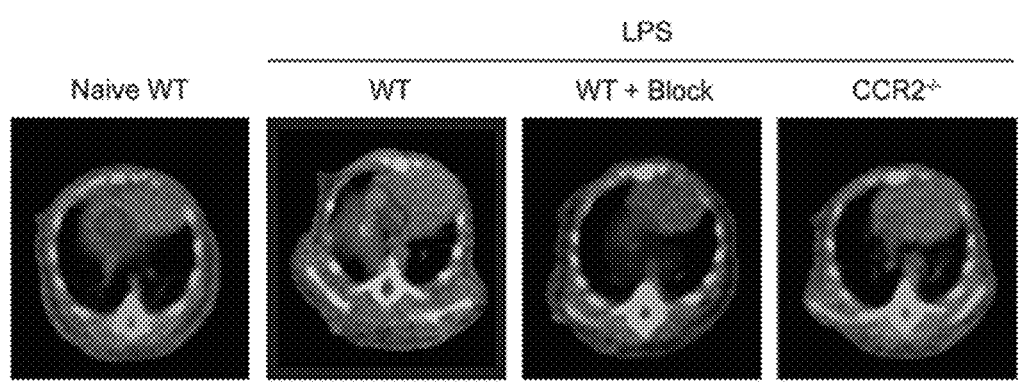
(FIG. 24A) Representative transverse PET images of mouse lung obtained from the indicated experimental condition: not treated WT mice (naive n=4); LPS-treated WT mice (WT, n=7; from FIG. 2B); LPS-treated WT co-injected with non-radiolabeled ECL1i (blocked, n=4) or LPS-treated CCR2-deficient mice (CCR2$^{-/-}$, n=4).
Figure 24B:
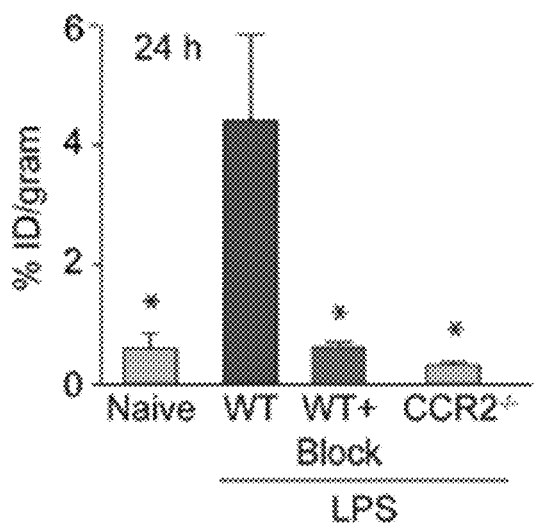
-FIG. 24B is a PET image and a bar graph depicting the specificity of $^{64}$Cu-DOTA-ECL1i imaging in LPS lung injury model. Mice were not treated (naive), or delivered intratracheal LPS and 24 h later injected with $^{64}$Cu-DOTA-ECL1i for PET/CT imaging.

The specificity of the ECL1i radiotracer was examined in additional control conditions (see e.g., FIG. 24). The level of $^{64}$Cu-DOTA-ECL1i lung signal in naive mice (mean % ID/g=0.39, n=3) was negligible and not significantly different from that observed in mice treated with PBS. Moreover, the signal in these conditions was similar to LPS-treated mice that were co-injected with excess non-radioactive ECL1i plus $^{64}$Cu-DOTA-ECL1i (blocked) (mean % ID/g=0.63±0.15, n=4, P<0.001). There was also nearly complete loss of lung signal in LPS-treated CCR2-deficient mice (mean % ID/g=0.39±0.04, n=3, P<0.001). We considered that blood flow may contribute to differences in the PET signal between LPS-treated and control mice, however, there were not significant differences in lung weight wet-to-dry ratios in PBS- compared to LPS-treated mice (5.20±0.20 g vs. 5.34±0.34 g, n=3/group, P=0.650).

ECL1i Tracer Binds Monocytes In Vivo.

Figure 25:
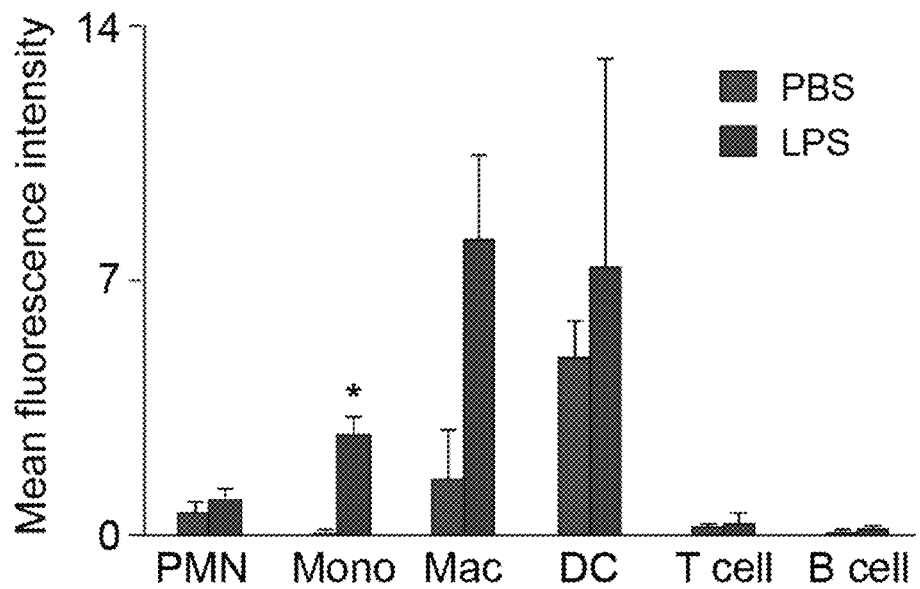
FIG. 25 is a bar graph showing the detection of ECL1i-Dylight 550 in lung immune cells after LPS-induced lung injury. Mice treated with intratracheal PBS or LPS were given intravenous fluorescent-labeled ECL1i, or non-injected at 24 h. One h later, lung cell digests were analyzed by flow cytometry for ECL1i-Dylight550$^+$ cells using cell-type specific antibodies. Cell types: PMN, neutrophils; Mono, monocytes; Macro, macrophages; DC, dendritic; T and B cells, lymphocytes. Shown are mean±SE of 4 independent experiments, total n=4/PBS group and n=5/LPS group injected with ECL1i; non-injected control mice for flow cytometry, n=4/PBS group, n=4 LPS/group. *P=0.001 compared to PBS treatment by unpaired t-test.
Figure 26A:
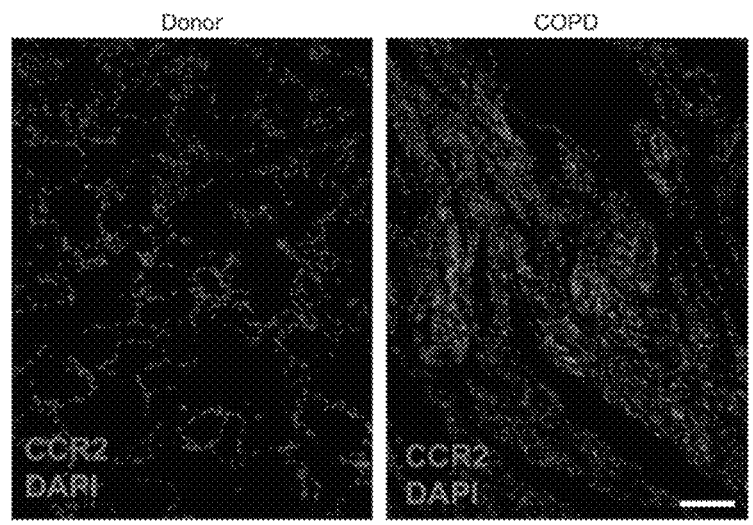
FIG. 26A-FIG. 26D is a series of images and plots showing $^{64}$Cu-DOTA-ECL1i binding in human lung samples from subjects with severe COPD.
Figure 26B:
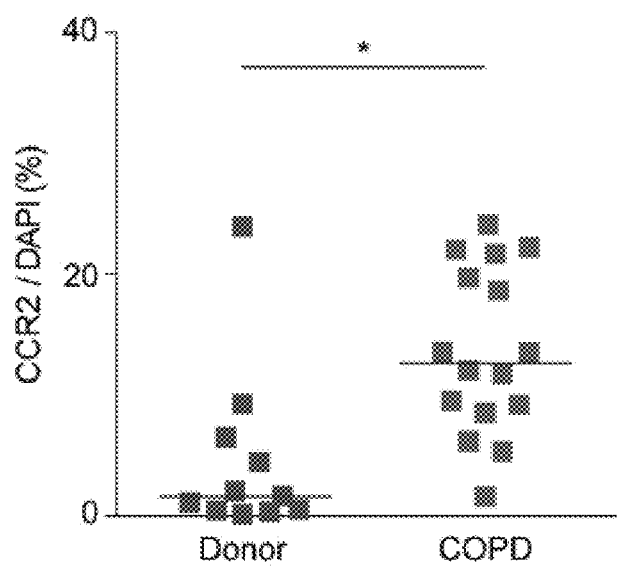
Figure 26C:
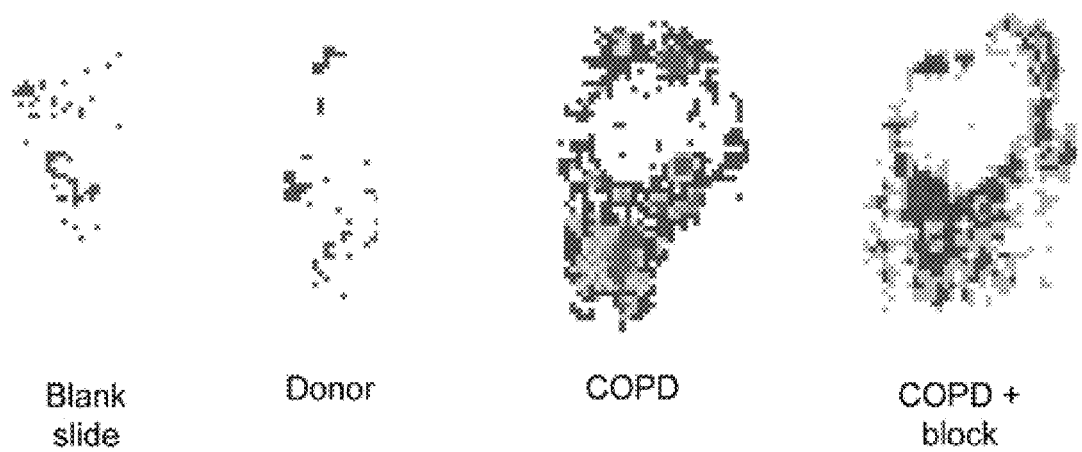
Figure 26D:
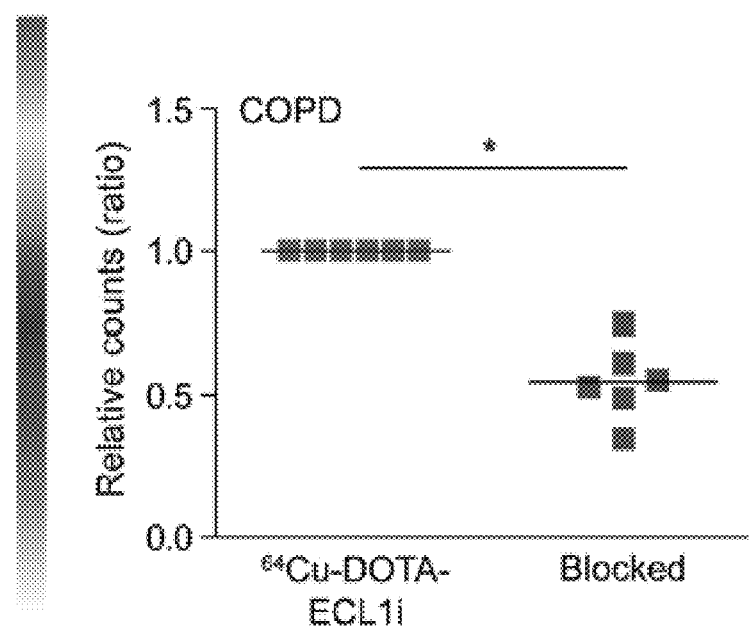

To determine the cell types that bound ECL1i in wild type mice, the peptide was tagged with the fluorescent dye Dylight 550. At 24 h post-intratracheal PBS or LPS delivery, ECL1i-Dylight 550 was injected intravenously and one hour later, lungs were analyzed by flow cytometry. LPS induced significant binding of ECL1i-Dylight 550 to monocytes ($Ly6G^{lo}$, $Ly6C^{hi}$) (see e.g., FIG. 25). ECL1i-Dylight 550 also bound lung to macrophages ($CD11b^{hi}$, $CD11c^{low}$) and a very small group of "bright" dendritic cells ($CD11b^{hi}$, $CD1c^{hi}$), consistent with known $CCR2^+$ populations (1, 2).

CCR2 Detection in Lung Tissue from Subjects with COPD.

The percentage of $CCR2^+$ cells was significantly increased in lung tissues from COPD subjects (median 12.82 percent cells/sample, range 1.16-24.11) compared to lung donors (median 1.66 percent cells/sample range 0.19-23.67; P=0.002) (see e.g., FIG. 26, TABLE 1). However, there were a wide range of $CCR2^+$ cells, with the levels being similar in tissues from some COPD and non-COPD subjects.

Accordingly, we next tested the binding of $^{64}$Cu-DOTA-ECL1i in the lung tissue sections from COPD and donor subjects using autoradiography on slides. To enhance the differences in CCR2 detection, we studied samples with high versus low numbers of $CCR2^+$ cells detected by immunostaining. This comparison showed that $^{64}$Cu-DOTA-ECL1i binding was increased in representative samples with high numbers compared to those with low numbers of $CCR2^+$ cells (see e.g., FIG. 26C). Qualitative assessment of probe binding was determined by blocking the $^{64}$Cu-DOTA-ECL1i signal using non-labeled ECL1i in tissue samples from COPD subjects with high levels of $CCR2^+$ cells. In all samples tested (n=6), competition with non-labeled ECL1i diminished the level of $^{64}$Cu-DOTA-ECL1i binding based on autoradiographic signal (see e.g., FIG. 26D).

Discussion.

We selected a CCR2 binding peptide as a PET imaging target based on several observations. First, the CCR2/CCL2 axis recruits inflammatory monocytes and other types of immune cells into the lung (1). Second, CCR2 is elevated in lung cells in ARDS, COPD, experimental asthma and pulmonary fibrosis, as well as common non-pulmonary diseases, including atherosclerosis and malignancy (6,8-10,17, 25-28). Third, there is substantial evidence that genetic deletion or pharmacologic inhibition of CCR2 ameliorates disease in animal models leading to industry efforts to develop and trial CCR2 antagonists for respiratory disorders and other disease (2,18,19).

Current tools are limited for the non-invasive assessment of inflammation in lung disease. To test $^{64}$Cu-DOTA-ECL1i as an agent to detect inflammation, we chose LPS injury, a well-established model that has been characterized relative to CCR2-mediated inflammation (13,24,29). Prior reports demonstrate that LPS directs accumulation of CCR2-expressing cells in the lung in wild type, but not $CCR2^{-/-}$ mice, or after anti-CCR2 antibody blockade (13,24,30). Consistent with these findings, $^{64}$Cu-DOTA-ECL1i activity in the lung was increased only during the acute phase of injury and was not present in $CCR2^{-/-}$ mice. The specificity of $^{64}$Cu-DOTA-ECL1i activity was further shown by the ability to block detection of LPS-induced activity using non-radioactive ECL1i.

Because CCR2 deletion in mice alters immune responses, including decreased neutrophil influx and other inflammatory cells in the lung (13-15), we sought alternative approaches to study the in vivo performance of ECL1i. To determine the cell types binding ECL1i we created a fluorescently tagged ECL1i imaging agent for in vivo labeling of immune cells in wild type mice. Injection of ECL1i-Dylight 550 and analysis of whole lung cell preparations by flow cytometry revealed ECL1i signal in lung monocytes and macrophages, as well as in small numbers of dendritic cells, also known to express CCR2 (12,26,29). Thus, future in vivo studies using ECL1i-Dylight 550 with CCR2 reporter mice may provide additional information as to cell targets. Ultimately, characterizing the complete identity of cell types that bind $^{64}$Cu-DOTA-ECL1i in vivo will be difficult owing to inherent differences in the sensitivity of detection methods for fluorescent and radionuclide labels.

$^{64}$Cu-DOTA-ECL1i joins a small number of agents developed for PET imaging of non-malignant lung disease. The strength of the ECL1i radiotracer is an ability to image CCR2-related inflammation, as we have shown in the lung using the mouse endotoxin and a mouse ischemia-reperfusion model of lung transplantation (21). $^{64}$Cu-DOTA-ECL1i activity in the bone marrow and extrapulmonary organs suggests that it may also be possible to follow CCR2 cell trafficking. Moving forward, It will be important to compare the utility of $^{64}$Cu-DOTA-ECL1i with radiotracers that are less specific for a defined immune cell population, such as $^{16}$FDG PET (5,31), and using single photon emission computed tomography or planar imaging with technetium-99m hexamethylpropylene amine oxime ($^{99m}$Tc-HMPAO) (32), as well as targeted approaches including the translocator protein (TSPO) (33) and folate receptor p (34) to identify CCR2-dependent inflammation.

We identified that the percent of CCR2 expressing cells detected by immunostaining was elevated in lung tissue from subjects with severe COPD compared to the lung donor group. This finding was consistent with prior reports of elevated levels of $CCR2^+$ cells in other types of samples obtained from individuals with COPD (6,7). There was some overlap in levels between the COPD and donor groups, possibly due to underlying phenotypic differences in COPD and inflammation that may occur in the donor lungs prior to harvest for transplantation. Thus, further study will be needed to define precise differences for $CCR2^+$ cells in COPD, but the present observations identify a set of clinical samples and a strategy that can be used to validate whether the level of $CCR2^+$ cells in tissue correlates with the level detected using our probe for non-invasive imaging.

We have assessed radiotracer activity in a limited number of mice and $^{64}$Cu-DOTA-ECL1i has a very rapid blood clearance (<1% ID/g at 1 h post injection), so that the sensitivity of detection may be limited. Chemical modification of the radiotracer could improve the pharmacokinetics to increase the blood retention time. While we have shown that ECL1i can bind human tissues in from subjects with COPD, sampling issues inherent in this heterogeneous disease prevent generalization to the whole lung. Assessing mice was performed on a relatively small numbers of have been studied with PET/CT following $^{64}$Cu-DOTA-ECL1i injection and models of chronic lung disease such as COPD are lacking, cigarette smoke in mice does not induce inflammation similar to that in humans (35). Interpretation of results is also limited by a lack of current approval for clinical testing. Moving to human trials may be the only way to test our proposal that a $^{64}$Cu-DOTA-ECL1i signal is increase in the lungs of subjects with COPD. While the $^{64}$Cu decay half-life of ~13 h may be less desirable for imaging, the high specific activity and the longer physical half-life will permit production and distribution of intact radiotracer for nationwide trials. For expanded clinical use of ECL1i, radiochemistry could be developed for fluoride-18 labeling. Moreover, future human studies of PET imaging using radiolabeled ECL1i in combination with computed tomography x-ray may provide synergistic information regarding the localization of inflammation, and the relationship to specific lung structures and pathologic changes.

Practical Applications.

A CCR2 binding peptide adapted as a PET probe can detect lung inflammation in a mouse model and human tissues, and may serve as a tool for the management of human lung disease. Our study of lungs of subjects with clinically similar, very severe COPD showed that expression of CCR2 varied markedly among subjects, supporting the concept that the molecular mechanisms underlying chronic inflammatory lung pathologies are not necessarily alike, but could be differentiated by non-invasive detection of certain biomarkers. There are few available treatments for COPD, and CCR2 detection could be an important step for developing therapies, personalizing treatment and monitoring treatment response.

REFERENCES FOR EXAMPLE 2

1. Charo I F, Ransohoff R M. The many roles of chemokines and chemokine receptors in inflammation. N Engl J Med. 2006; 354(6):610-21.
2. Tomankova T, Kriegova E, Liu M. Chemokine receptors and their therapeutic opportunities in diseased lung: far beyond leukocyte trafficking. Am J Physiol Lung Cell Mol Physiol. 2015; 308(7):L603-18.
3. Byers D E, Holtzman M J. Alternatively activated macrophages and airway disease. Chest. 2011; 140(3):768-74.
4. Deshane J S, Redden D T, Zeng M, et al. Subsets of airway myeloid-derived regulatory cells distinguish mild asthma from chronic obstructive pulmonary disease. J Allergy Clin Immunol. 2015; 135(2):413-24 e15.
5. Chen D L, Schuster D P. Imaging pulmonary inflammation with positron emission tomography: a biomarker for drug development. Mol Pharm. 2006; 3(5):488-95.
6. de Boer W I, Sont J K, van Schadewijk A, Stolk J, van Krieken J H, Hiemstra P S. Monocyte chemoattractant protein 1, interleukin 8, and chronic airways inflammation in COPD. J Pathol. 2000; 190(5):619-26.
7. Traves S L, Culpitt S V, Russell R E, Barnes P J, Donnelly L E. Increased levels of the chemokines GROalpha and MCP-1 in sputum samples from patients with COPD. Thorax. 2002; 57(7):590-5.
8. Hartl D, Griese M, Nicolai T, et al. A role for MCP-1/CCR2 in interstitial lung disease in children. Respir Res. 2005; 6:93.
9. Kallinich T, Schmidt S, Hamelmann E, et al. Chemokine-receptor expression on T cells in lung compartments of challenged asthmatic patients. Clin Exp Allergy. 2005; 35(1):26-33.
10. An J L, Ishida Y, Kimura A, Tsokos M, Kondo T. Immunohistochemical detection of CCR2 and CX3CR1 in sepsis-induced lung injury. Forensic Sci Int. 2009; 192(1-3):e21-5.
11. Tsou C L, Peters W, Si Y, et al. Critical roles for CCR2 and MCP-3 in monocyte mobilization from bone marrow and recruitment to inflammatory sites. J Clin Invest. 2007; 117(4):902-9.
12. Lin K L, Suzuki Y, Nakano H, Ramsburg E, Gunn M D. CCR2+ monocyte-derived dendritic cells and exudate macrophages produce influenza-induced pulmonary immune pathology and mortality. J Immunol. 2008; 180(4):2562-72.
13. Maus U, von Grote K, Kuziel W A, et al. The role of CC chemokine receptor 2 in alveolar monocyte and neutrophil immigration in intact mice. Am J Respir Crit Care Med. 2002; 166(3):268-73.
14. Maus U A, Waelsch K, Kuziel W A, et al. Monocytes are potent facilitators of alveolar neutrophil emigration during lung inflammation: role of the CCL2-CCR2 axis. J Immunol. 2003; 170(6):3273-8.
15. Serbina N V, Pamer E G. Monocyte emigration from bone marrow during bacterial infection requires signals mediated by chemokine receptor CCR2. Nat Immunol. 2006; 7(3):311-7.
16. Hildebrandt G C, Duffner U A, Olkiewicz K M, et al. A critical role for CCR2/MCP-1 interactions in the development of idiopathic pneumonia syndrome after allogeneic bone marrow transplantation. Blood. 2004; 103(6):2417-26.
17. Bhatia M, Zemans R L, Jeyaseelan S. Role of chemokines in the pathogenesis of acute lung injury. Am J Respir Cell Mol Biol. 2012; 46(5):566-72.
18. Struthers M, Pasternak A. CCR2 antagonists. Curr Top Med Chem. 2010; 10(13):1278-98.
19. Carter P H. Progress in the discovery of CC chemokine receptor 2 antagonists, 2009-2012. Expert Opin Ther Pat. 2013; 23(5):549-68.
20. Auvynet C, Baudesson de Chanville C, Hermand P, et al. ECL1i, d(LGTFLKC), a novel, small peptide that specifically inhibits CCL2-dependent migration. FASEB J. 2016.
21. Liu Y, Li W, Luehmann H P, et al. Noninvasive Imaging of CCR2+ Cells in Ischemia-Reperfusion Injury After Lung Transplantation. Am J Transplant. 2016.
22. Liu Y, Abendschein D, Woodard G E, et al. Molecular imaging of atherosclerotic plaque with (64)Cu-labeled natriuretic peptide and PET. J Nucl Med. 2010; 51(1):85-91.
23. Liu Y, Ibricevic A, Cohen J A, et al. Impact of hydrogel nanoparticle size and functionalization on in vivo behavior for lung imaging and therapeutics. Mol Pharm. 2009; 6(6):1891-902.
24. Maus U A, Wellmann S, Hampl C, et al. CCR2-positive monocytes recruited to inflamed lungs downregulate local CCL2 chemokine levels. Am J Physiol Lung Cell Mol Physiol. 2005; 288(2):L350-8.
25. Lee Y G, Jeong J J, Nyenhuis S, et al. Recruited alveolar macrophages, in response to airway epithelial-derived monocyte chemoattractant protein 1/CCl2, regulate airway inflammation and remodeling in allergic asthma. Am J Respir Cell Mol Biol. 2015; 52(6):772-84.
26. Robays L J, Maes T, Lebecque S, et al. Chemokine receptor CCR2 but not CCR5 or CCR6 mediates the increase in pulmonary dendritic cells during allergic airway inflammation. J Immunol. 2007; 178(8):5305-11.
27. Okuma T, Terasaki Y, Kaikita K, et al. C-C chemokine receptor 2 (CCR2) deficiency improves bleomycin-induced pulmonary fibrosis by attenuation of both macrophage infiltration and production of macrophage-derived matrix metalloproteinases. J Pathol. 2004; 204(5):594-604.
28. Charo I F, Peters W. Chemokine receptor 2 (CCR2) in atherosclerosis, infectious diseases, and regulation of T-cell polarization. Microcirculation. 2003; 10(3-4):259-64.
29. Martinu T, Gowdy K M, Nugent J L, et al. Role of C-C motif ligand 2 and C-C motif receptor 2 in murine pulmonary graft-versus-host disease after lipopolysaccharide inhalations. Am J Respir Cell Mol Biol. 2014; 51(6):810-21.
30. Yang D, Tong L, Wang D, Wang Y, Wang X, Bai C. Roles of CC chemokine receptors (CCRs) on lipopolysaccharide-induced acute lung injury. Respir Physiol Neurobiol. 2010; 170(3):253-9.
31. de Prost N, Tucci M R, Melo M F. Assessment of lung inflammation with 18F-FDG PET during acute lung injury. AJR Am J Roentgenol. 2010; 195(2):292-300.
32. Audi S H, Clough A V, Haworth S T, et al. 99MTc-Hexamethylpropyleneamine Oxime Imaging for Early Detection of Acute Lung Injury in Rats Exposed to Hyperoxia or Lipopolysaccharide Treatment. Shock. 2016.
33. Hatori A, Yui J, Yamasaki T, et al. PET imaging of lung inflammation with [18F]FEDAC, a radioligand for translocator protein (18 kDa). PLoS One. 2012; 7(9):e45065.
34. Han W, Zaynagetdinov R, Yull F E, et al. Molecular imaging of folate receptor beta-positive macrophages during acute lung inflammation. Am J Respir Cell Mol Biol. 2015; 53(1):50-9.
35. Churg A, Sin D D, Wright J L. Everything prevents emphysema: are animal models of cigarette smoke-induced chronic obstructive pulmonary disease any use? Am J Respir Cell Mol Biol. 2011; 45(6):1111-5.
36. Boswell C A, Sun X, Niu W, et al. Comparative in vivo stability of copper-64-labeled cross-bridged and conventional tetraazamacrocyclic complexes. Journal of Medicinal Chemistry. 2004; 47(6):1465-74.
37. Pan J, You Y, Huang T, Brody S L. RhoA-mediated apical actin enrichment is required for ciliogenesis and promoted by Foxj1. J Cell Sci. 2007; 120(Pt 11):1868-76.
38. Schneider C A, Rasband W S, Eliceiri K W. NIH Image to ImageJ: 25 years of image analysis. Nat Methods. 2012; 9(7):671-5.

Example 3: Imaging Mouse Models of Lung Diseases, Disorders, and Conditions

The following example describes methods of imaging CCR2 receptors in the lung to guide diagnosis and therapy. Lung diseases are often characterized by the nature of immune or inflammatory cells that are found within the tissues and airways[1-4]. Chemokines guide the migration and function of inflammatory cells harboring their cognate receptor[5,6]. In the lung, the chemokine CCL2 (monocyte chemoattractant protein-1, MCP-1), is frequently elevated in acute and chronic lung disease[7-9]. CCL2 is the major ligand for the chemokine receptor CCR2, which is found largely on immune cells and notably on monocytes, dendritic cells (DCs) and T cells[5,6,10-12].

Why Image CCR2+ Cells in Acute and Chronic Lung Disease?

CCR2 was selected as a PET imaging target based on: (1) knowledge that the CCR2/CCL2 axis recruits inflammatory monocytes and other cell types into the lung (and other organs); (2) elevation of CCR2/CCL2 in acute and chronic lung diseases; (3) evidence that genetic deletion or pharmacologic inhibition of CCR2 ameliorates disease in animal models; (4) industry efforts to develop and trial CCR2 antagonists for lung and other disease (e.g., diabetes, malignancies); and (5) an inability to non-invasively identify CCR2+ cell burden in tissues for optimal personalized treatment.

CCR2 Directs Monocytes and Other Immune Cell Recruitment in the Lung.

A major role for the CCL2/CCR2 pair is the recruitment of inflammatory monocytes from the bone marrow[7,13] and regulation of macrophage, dendritic and T cells maturation[9,14]. In response to CCL2, CCR2+ monocytes adhere to the vascular endothelial surface and migrate into tissue, along chemotactic gradients[15]. Inflammatory monocytes (mouse Ly6C$^{hi}$ Ly6G$^{lo}$, human CD14+CD16−) serve as precursors for classical macrophages and conventional DCs[16]. CCR2+ monocytes also provide a secondary source of proinflammatory modulators, such as tumor necrosis factor-α, interleukin-1β and matrix metalloproteinases, contributing to lung injury[17-19]. Although inflammatory monocytes are essential early responders, excessive or prolonged recruitment impairs resolution of inflammation and propagates disease progression.

CCL2/CCR2 is Elevated in Lung Disease.

As described herein, CCR2 can act as a biomarker for lung inflammation used to stratify treatments (e.g., anti-inflammatory or CCR2 antagonists) and to monitor disease. The CCL2/CCR2 axis is demonstrated to be active in acute and chronic lung diseases. CCR2 function is supported by deletion or antagonism in related mouse models. Diseases include those for which specific therapies are limited, including those detailed below.

Acute lung injury. Excessive recruitment of CCR2-dependent leukocytes impacts the pathogenesis of acute lung injury in human ARDS and mouse models, shaping the magnitude and duration of disease[20-22]. Endotoxin (LPS) triggers CCR2-depedent migration of monocytes to the lung when administered intratracheally and also influences subsequent neutrophil recruitment in lung.

PGD. Reperfusion injury immediately following lung transplant, known as primary graft dysfunction (PGD), is marked by elevated CCL2 levels in BAL fluid, while clinical improvement occurs as CCL2 levels fall. It was observed that CCR2 is required for mobilization of CD11b+ Ly6C$^{hi}$ monocytes and accumulation into lung allographs in a mouse lung transplant model of PGD.

COPD. Human studies of CCL2/CCR2 in COPD show increased levels of CCL2 in the sputum, BAL fluid and lungs (including ex-smokers) and expression of CCR2 on leukocytes and epithelia. Our group recently reported increased CCR2 on interstitial monocytes from COPD lung tissue.

Asthma. In human subjects with asthma studied by segmental allergy bronchoprovocation, CCL2 and CCR2 were increased in BAL. Blocking or genetic deletion of CCL2/CCR2 in mouse models of airway allergen sensitization prevents monocyte and dendritic cell migration and allergic responses[8,36-38].

Pulmonary fibrosis and others. Human and mouse studies have also implicated the CCL2/CCR2 axis in the pathogenesis of pulmonary fibrosis, bronchiolitis obliterans syndrome, and fungal pneumonia.

CCR2 Plays Roles in a Broad Number of Pathologic Processes Beyond the Lung.

The importance of CCR2 as a biomarker and as a radiotracer extends well beyond the lung. Experimental evidence for CCR2 deletion includes attenuation of atherosclerotic plaques, myocardial infarction, sepsis, allograph rejection, glucose control and nephropathy in diabetes, symptoms in multiple sclerosis and the extent of tumor metastasis.

Clinical Trials of CCR2 Antagonists.

A remarkable number of CCR2 antagonists have been produced and the website ClinicalTrials.gov lists 16 CCR2 antagonist trials. Small molecules are in trials for atherosclerosis, rheumatoid arthritis, multiple sclerosis, pancreatic cancer and other diseases. In one study, CCR2 antagonists decreased urinary albumin and improved glycemic control. As for lung disease, a Phase 1 study of COPD in Eastern Europe reported no toxicity (NCT01215279). Other trials of antagonists have failed, possibly due to an inability to molecularly phenotype subjects and monitor a CCR2-specific endpoint.

CCR2 PET Imaging can Serve to Phenotype, Monitor, and Guide Treatment.

Chemokine receptor phenotyping is a step toward precision medicine. Lung medicine lags considerably behind oncology and other disciplines where the use of molecular markers has become the standard of care. The inability to easily molecularly phenotype patient populations is a significant gap in the field and has possibly slowed progress. Non-invasive chemokine receptor phenotyping technology using PET imaging can drive the field. Inflammatory cells cannot be accurately sampled from the lung. Bronchoalveolar lavage (BAL) is restricted to those cells within the airspaces rather than the interstitial spaces, which is a residence for inflammatory populations. Biopsy is more invasive and suffers from sampling error. Given the high sensitivity, quantification, and translation capability of PET, as documented for oncological applications, CCR2 PET imaging can be rapidly adopted for translational research. Thus, a robust and accurate non-invasive method to measure CCR2 expression is highly attractive from a disease staging and drug discovery perspective.

Novel Chemokine Receptor Radiotracer Development.

CCR2 targeting ligand (ECL1i) and radiotracer ($^{64}$Cu-DOTA-ECL1i) are novel. Our group has been a leader in the preclinical development of PET imaging of chemokine receptors—we developed a pan-chemokine receptor (vMIP-II) and CCR5-based tracers in mouse models of vascular inflammatory lesions. CXCR4 is the sole other chemokine receptor identified by PET imaging. A $^{66}$Ga-CXCR4 antagonist was recently used for imaging human cancer.

Broadly Applicable CCR2 Radiotracer.

As there are no imaging techniques for the non-invasive detection of CCR2, the radiotracer described in this project, if successful, will provide a valuable tool for studying pro-inflammatory immune cell trafficking in lung and other disease conditions. A CCR2 radiotracer may also permit the characterization of monocyte mobilization from bone marrow and spleen. Such information would provide the foundation for potential paradigm shifting approaches to the diagnosis and treatment of several common human diseases.

Lung Injury Model Development.

Together, we have established lung injury models (e.g., lung transplantation, transgenic mice) for the optimal testing of radiotracer sensitivity and specificity and a unique biorepository of phenotyped human lung tissues and cells from subjects with advanced lung disease to test our probe.

Approach.

The data provided herein describes the development and characterization of a CCR2 binding peptide, ECL1i designed with $^{64}$Cu radiolabeling ($^{64}$Cu-DOTA-ECL1i) for PET imagining. $^{64}$Cu was chosen as a widely used PET radioisotope, regularly produced by the Washington Univ. Cyclotron Facility, with desirable nuclear properties ($t_{1/2}$=12.7 h, $\beta^+$=0.653 Mev (17.8%), $\beta^-$=0.579 Mev (38.4%)) for pre-clinical and clinical investigation. Data includes tests of $^{64}$Cu-DOTA-ECL1i specificity, sensitivity and safety in several different models to best validate radiotracer function. Moving this agent to human safety studies, by means as described below, to validate the radiotracer in mice, can be performed by confirming binding in human cells, gaining FDA approval, and performing Phase 0 safety studies. The best mouse models to validate tracer performance will be used, making no attempt to "model" a human lung disease for which no mouse model is truly authentic and defensible. However, there is sufficient new and established CCR2-related human data to direct the studies without mouse models. The multidisciplinary team can generate the preclinical data and perform Phase 0/Early Phase 1 studies. Once accomplished, $^{64}$Cu-DOTA-ECL1i will be tested in Phase 1 studies for safety in a targeted population. Below are data that support the envisioned human studies.

Development of PET Chemokine Receptor Lung Imaging.

Figure 13A:
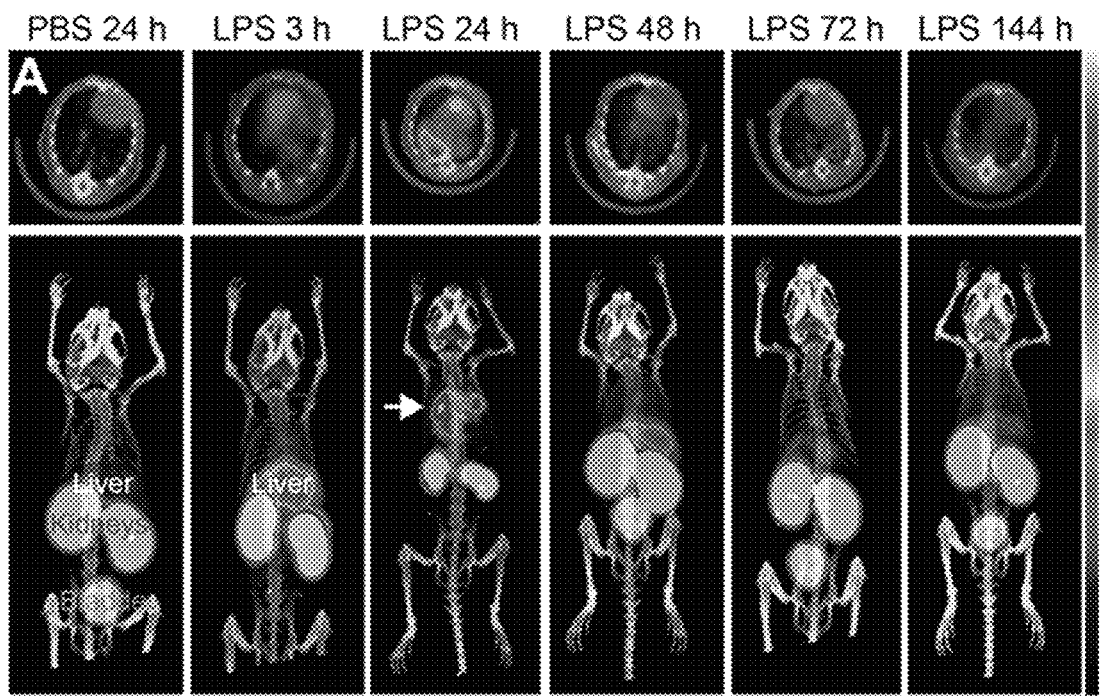
FIG. 13A-FIG. 13C is a series of PET images and bar graphs showing $^{64}$Cu-DOTA-vMIP-II PET imaging in LPS injured mouse lung.
Figure 13B:
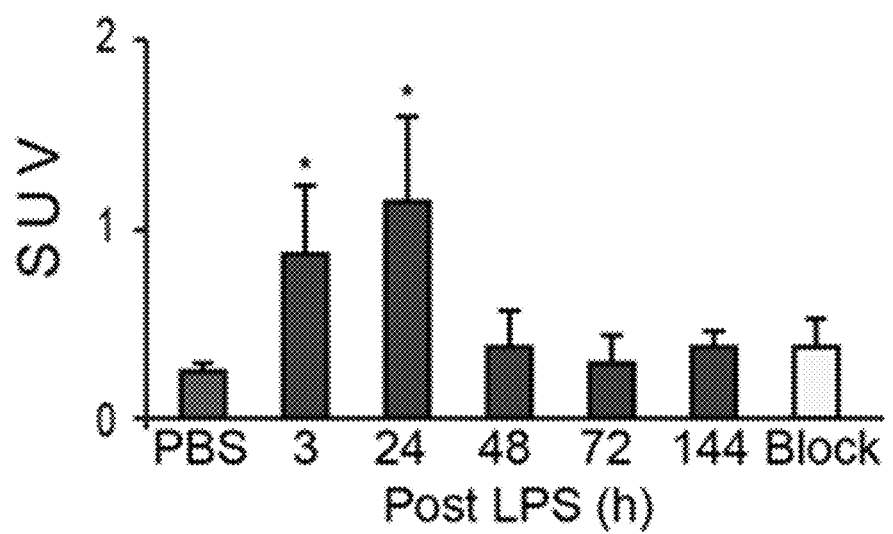

To determine if a radionuclide-labeled chemokine receptor-binding peptide could be used to detect lung inflammation, we employed the 68-residue vMIP-II derived from human Herpes virus 8[80]. vMIP-II binds and antagonizes activity of chemokine receptors CCR1 through 5 and 8, CXCR3 and 4, CR1, CX3CR1 and XCR1[80,81]. We hypothesized that vMIP-II could serve as a broad-spectrum probe for lung inflammation. The Liu lab showed that PET imaging using i.v. $^{64}$Cu-DOTA-vMIP-II detected chronic inflammation following vascular injury in ApoE$^{-/-}$ mice[82]. Accordingly, C57BL/6 mice administered intratracheal PBS or endotoxin (LPS, *E. coli* 055:B5, 2.5 mg/mL/kg)[83] were injected with $^{64}$Cu-DOTA-vMIP-II by tail vein and underwent dynamic PET/CT scans over 30 min (see e.g., FIG. 13A). Compared to PBS control, LPS induced a 3-4-fold higher vMIP-II signal in the lungs that peaked at 24 h (see e.g., FIG. 13B). When injected with the radiotracer at 48 h, 72 or 144 h, the lung signal was similar to control conditions. Concurrent administration of 100-fold excessive mass of non-radiolabeled vMIP-II blocked signal at 24 h post-LPS, suggesting that the $^{64}$Cu-DOTA-vMIP-II signal was specific. Moreover, $H_2^{15}O$ and $C^{15}O$ did not identify differences in blood pool at 24 h. Uptake was also observed in the liver in the mice given LPS (likely a systemic inflammatory response[84]), as well as kidneys and bladder activity, reflecting renal clearance.

vMIP-II Binds Lung Inflammatory Monocytes and Other Cell Types.

Figure 13C:
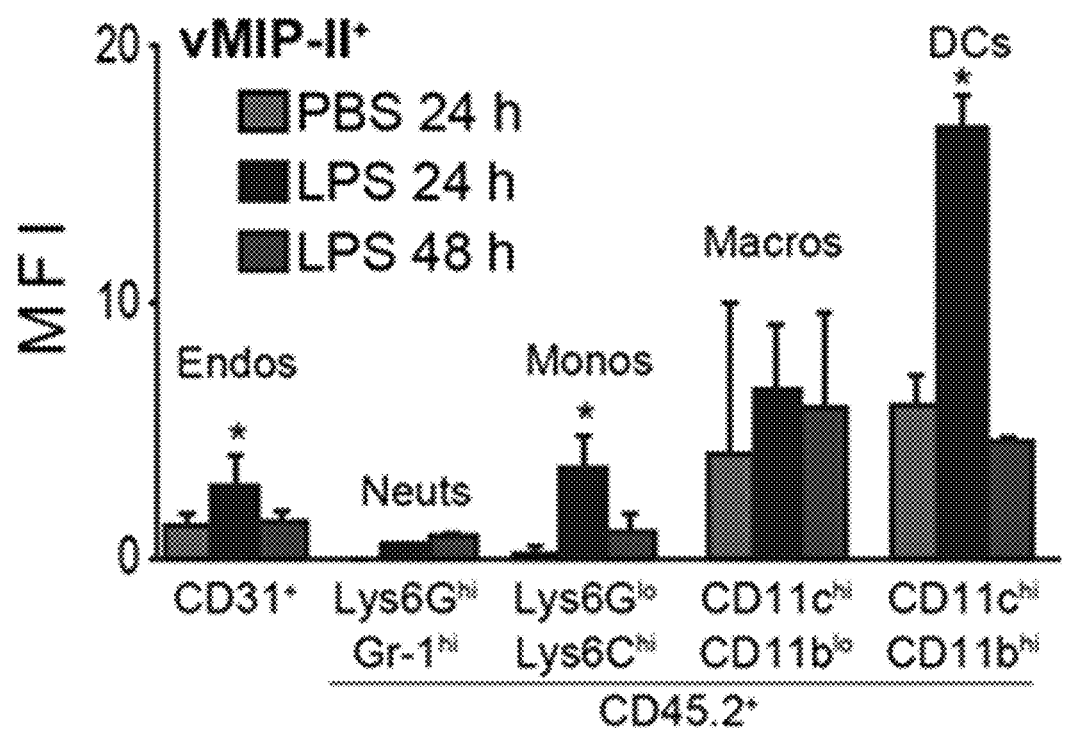

To determine the phenotype of cells that bound vMIP-II, fluorescently tagged peptide (with Dylight 550) was used in a protocol that paralleled the radiotracer studies. The lungs were digested and analyzed for immune cell markers that co-localized with DOTA-vMIP-II-Dylight550 using flow cytometry. LPS treated mice had vMIP-II$^+$ endothelial cells (CD31$^+$), monocytes (Ly6G$^{lo}$, Ly6C$^{hi}$) and a DC population (CD11b$^{hi}$, CD11c$^{hi}$) at 24 but not 48 h (see e.g., FIG. 13C), consistent with the acute influx of inflammatory monocytes post-LPS[25,42,85]. Two-photon microscopy using the same probe identified uptake in subepithelial regions of airways and in alveolar capillaries (data not shown). To image a molecularly defined inflammatory monocyte population, we identified a peptide that bound CCR2.

Identification of a CCR2 Binding Peptide.

ECL1i is a CCR2 binding peptide and antagonist developed by collaborator C. Combadiere (INSERM, Paris, FR, see letter) based on prior knowledge that mutagenesis of CCR2 threonine 117 impairs cell migration, but not signaling[86]. The heptapeptide LGTKLKC, (C) inverso (ECL1i) was designed to correspond and bind to an inverted sequence in the third transmembrane domain at the first extracellular loop (ECL1) of CCR2. The region is highly conserved in mouse and human.

Specificity of the CCR2 Binding Peptide ECL1i.

CCR2$^+$ cells migrate in response to CCL2. ECL1i specifically inhibited CCL2-induced chemotaxis in CHO cells that stably express human CCR2 (hCCR2) in a concentration-dependent manner and similar to CCR2 the antagonist BMS22[54,55]. However, ECL1i did not induce the migration of CHO-hCCR2 cells at concentrations that inhibited CCL2 signaling (data not shown). ECL1i also inhibited CCL2-mediated chemotaxis of CCR2$^+$ inflammatory monocytes, but not of resident monocytes. ECL1i did not inhibit the migration of cells expressing human CCR1, CCR5 or CX3CR1 (not shown). These data indicate that ECL1i selectively inhibits CCL2-induced chemotaxis of CCR2$^+$ cells without inducing chemotaxis of these cells. Also, incubation of CCR2-expressing HEK293 cells with ECL1i did not prevent the binding of fluorescently-labeled CCL1 (not shown), indicating distinct sites of interaction.

Synthesis and Characterization of $^{64}$Cu-DOTA-ECL1i.

We prepared DOTA-ECL1i by conjugating maleimido-mono-amide-DOTA with the CCR2 binding peptide LGT-FLKC using established methods[69]. The crude conjugate was purified by HPLC to reach 99% chemical purity and verified by mass spectrometry (M$^+$ calculated: 1306.65, observed: 1306.69) (see e.g., FIG. 2A, FIG. 2B). The DOTA-ECL1i conjugate was radiolabeled with $^{64}$CuCl$_2$ as described[69] with specific activity of 1.5±0.3 mCi/nmol (n=20), enabling injection of trace amounts (~70 pmol) for PET imaging. $^{64}$Cu-DOTA-ECL1i was 100% stable after incubation with mouse serum at 37° C. and in vivo, in blood and lung 1 h post injection, by HPLC analysis.

In Vivo Toxicity Studies.

Cytotoxicity assays of non-radioactive Cu-DOTA-ECL1i performed in human and mouse cells lines by MTT and ATP activity showed no change in activity compared to controls at concentrations up to 40 μg/mL/10$^5$ cells. Toxicity studies were performed by S. Greco, DVM (Dept. of Comparative Med., Washington Univ.). Mice given i.v. Cu-DOTA-ECL1i (110 μg) at 500-fold the estimated dose for human imaging evaluated 24 h later showed normal serum hepatic and renal chemistries, and histologic examination of lung, liver and kidneys (n=5 mice).

Figures 14A, 14B:
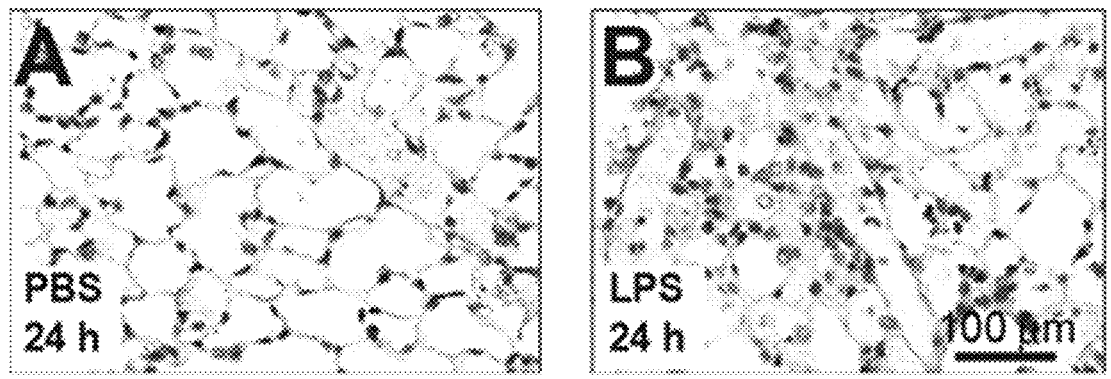
FIG. 14A-FIG. 14G is a series of images and bar graphs showing PET imaging CCR2 in LPS-injured mouse lung. Mice post intratracheal PBS or LPS.
Figures 14C, 14D:
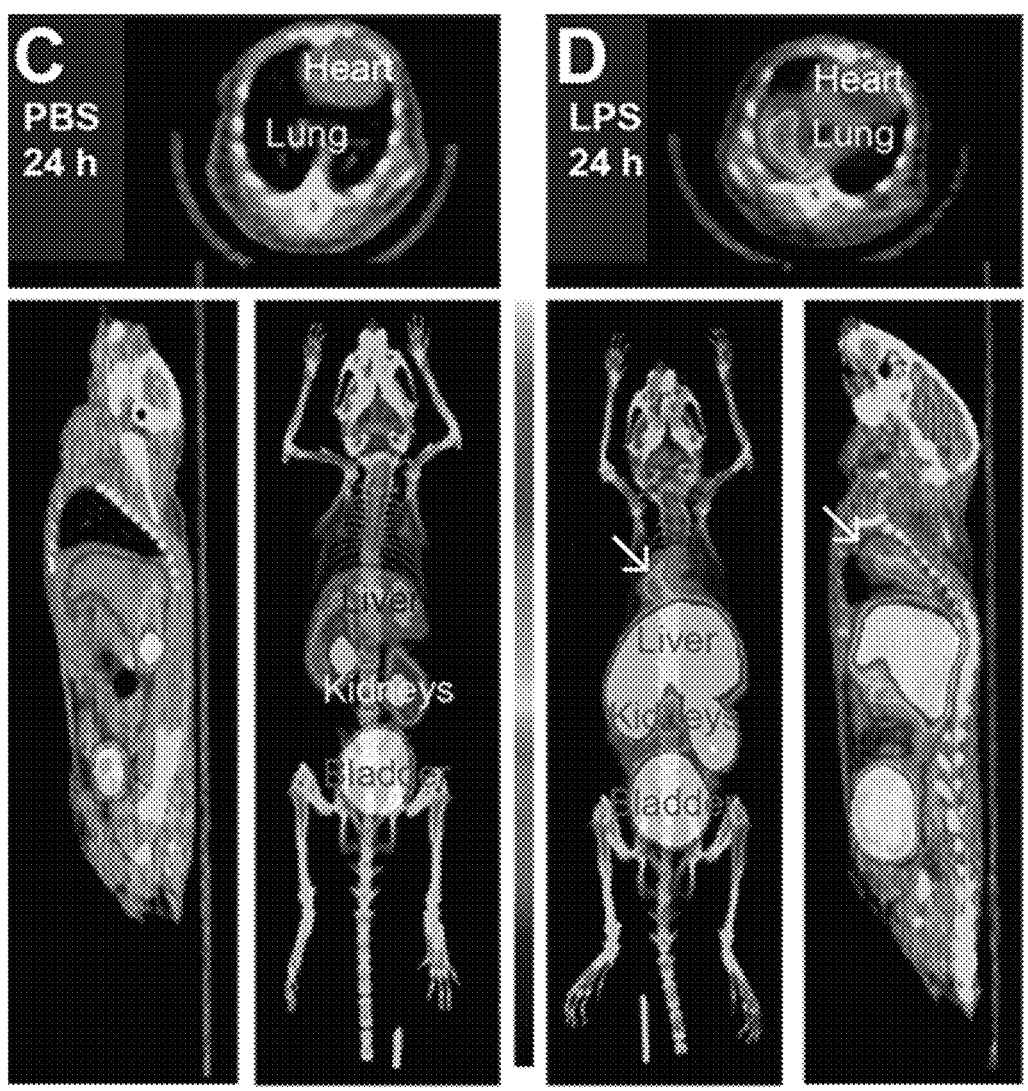

CCR2 Imaging in LPS Lung Injury (See e.g., FIG. 14).

CCR2 directs LPS-induced accumulation of monocytes in the lung in a dose- and time-dependent pattern in wild type but not CCR2$^{-/-}$ mice or after anti-CCR2 antibody blockade[25,85]. Thus mice were administered intratracheal PBS or LPS to determine if $^{64}$Cu-DOTA-ECL1i could be used as a PET agent to detect CCR2-expressing cells, as observed by immunostaining (see e.g., FIG. 14A, FIG. 14B). At 24 h, mice injected with $^{64}$Cu-DOTA-ECL1i via tail vein were imaged by PET/CT for 60 min (see e.g., FIG. 14C, FIG. 14D). Compared to PBS treatment, there was a prominent signal in the lungs of LPS treated mice. $^{64}$Cu-DOTA-ECL1i uptake in the lung peaked at 24 h, followed by a loss of signal in mice injected at 48 h or 166 h post-LPS (see e.g., FIG. 14E). Mice administered a low dose of LPS had a diminished lung signal, suggesting sensitivity (see e.g., FIG. 14D). Loss of lung signal in LPS-treated CCR2$^{-/-}$ or LPS-treated mice co-inject with excess non-radioactive plus $^{64}$Cu-DOTA-ECL1i suggested radiotracer specificity (see e.g., FIG. 14F). LPS also increased activity in the liver, consistent with a systemic inflammatory response[84]. Renal clearance was indicated by enhanced kidney and bladder activity in all mice.

Biodistribution of $^{64}$Cu-DOTA-ECL1i in the LPS Mouse Lung Injury Model.

Figures 14E, 14F, 14G:
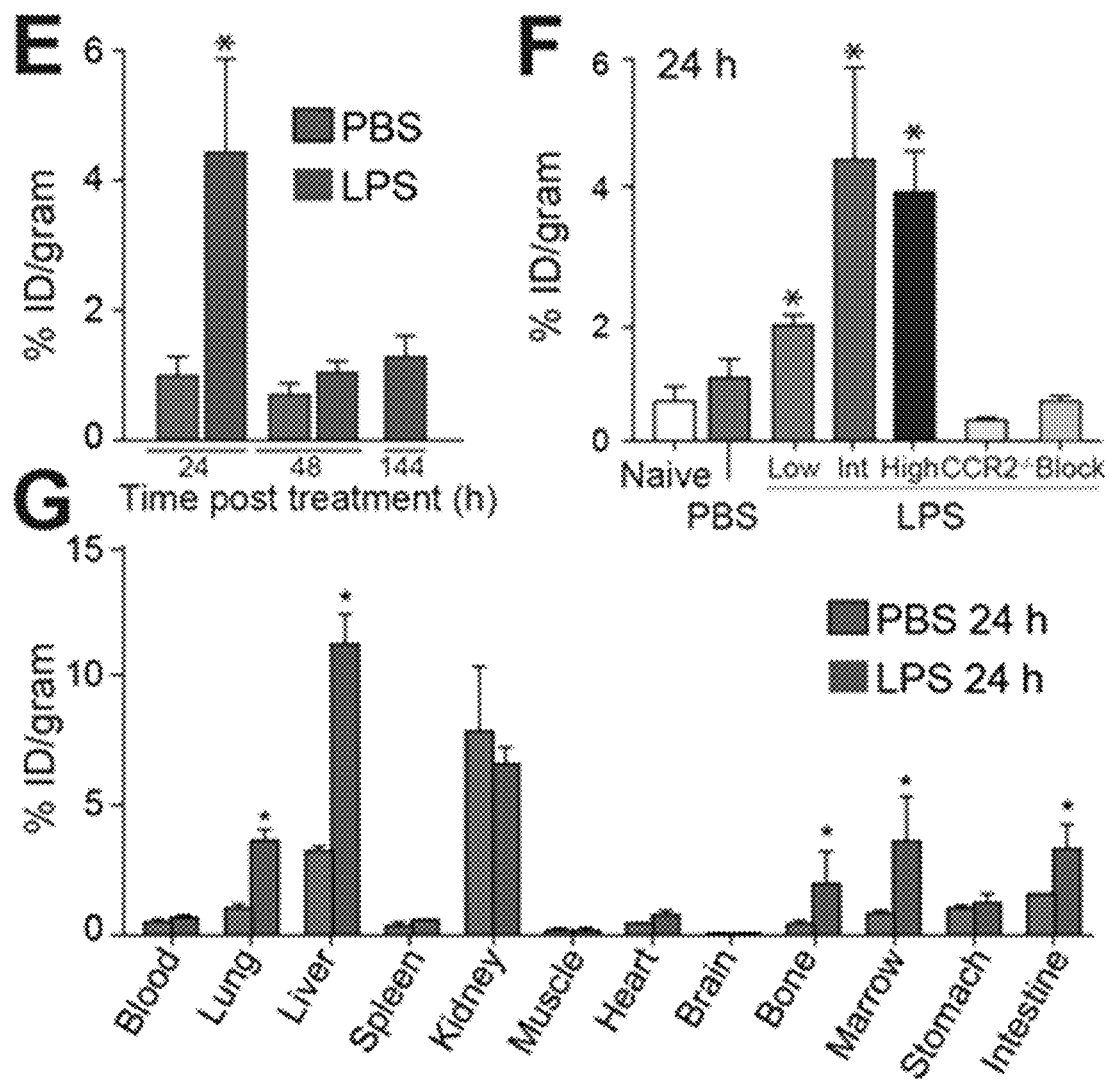

The in vivo pharmacokinetic evaluation of $^{64}$Cu-DOTA-ECL1i at 1 h post-injection was compared in mice 24 h after delivery of intratracheal PBS or LPS (see e.g., FIG. 14G). Following i.v. delivery, $^{64}$Cu-DOTA-ECL1i showed fast renal clearance evidenced by the kidney accumulation in both groups. Although there was no difference in blood retention between LPS and PBS treated mice, the lung accumulation of tracer in LPS group was 2.5 times higher than that acquired in the PBS group. As expected, liver, and bone marrow uptake of $^{64}$Cu-DOTA-ECL1i in LPS treated mice was higher than those in the PBS mice due to the LPS induced inflammation.

ECL1i Tracer Binds Inflammatory Monocytes In Vivo.

Figure 15:
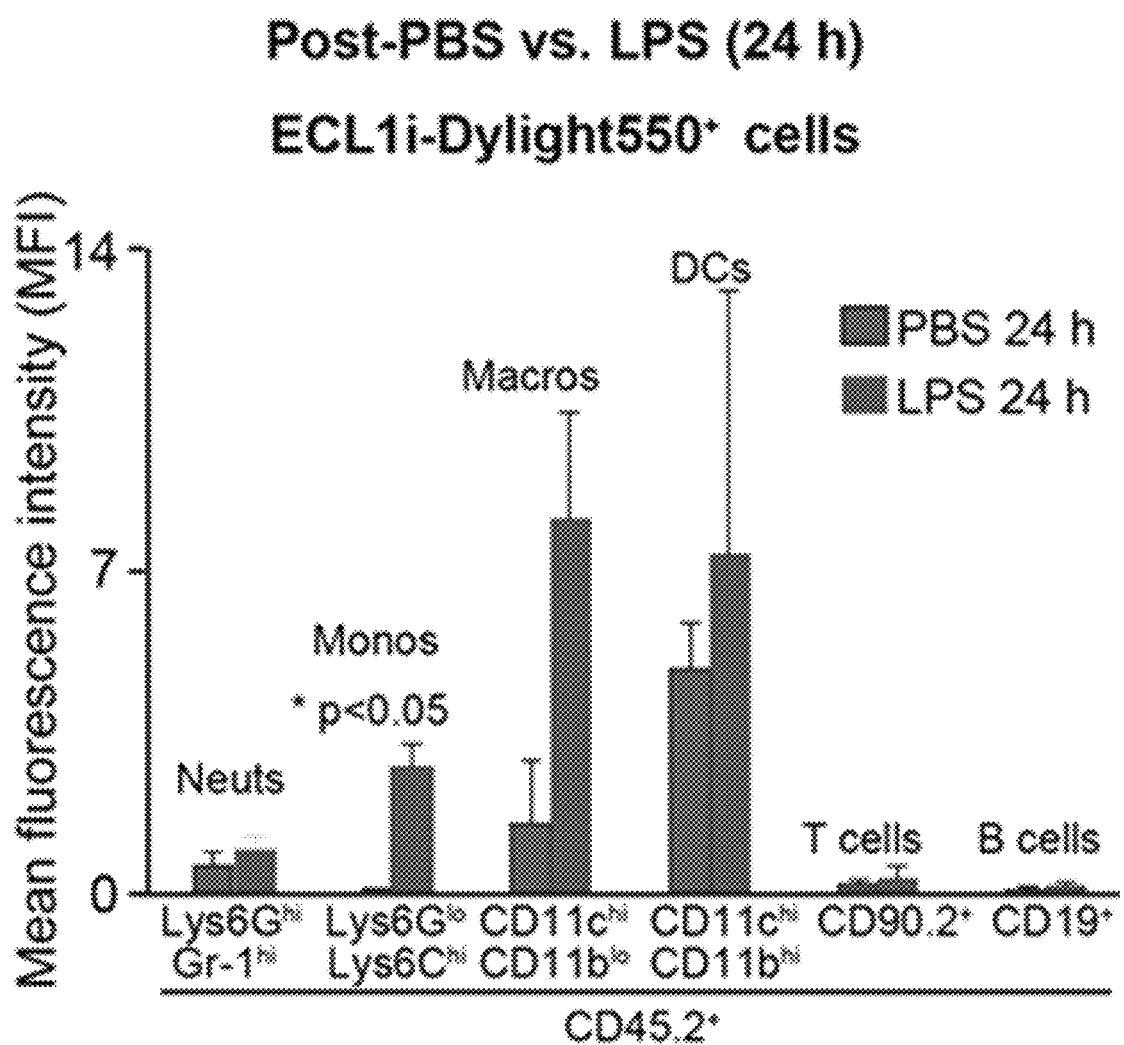
FIG. 15 is a bar graph showing ECL1i Dylight550$^+$ cells in vivo. Mice treated with intratracheal PBS or LPS were given i.v. fluorescent-labeled ECL1i at 24 h. Lung cell digests were analyzed by flow cytometry for ECL1-Dylight550$^+$ cells. Shown are mean±SD of 3 independent experiments. *p<0.05.

To determine the LPS-induced cell types that bound $^{64}$Cu-DOTA-ECL1i, ECL1i was tagged with fluorescent Dylight 550 and injected in PBS or LPS treated mice. Cells from lung digest were analyzed by flow cytometry at 24 h. LPS induced significant binding of ECL1i-Dylight 550 to monocytes (Ly6G$^{lo}$, Ly6C$^{hi}$) (see e.g., FIG. 15). A very small population of "bright" DCs (CD11b$^{hi}$, CD11c$^{hi}$) bound ECL1i-Dylight 550, but was not significantly different between conditions. More detailed in vivo studies of ECL1i binding population are described in Example 3A.

Figures 6A, 6B:
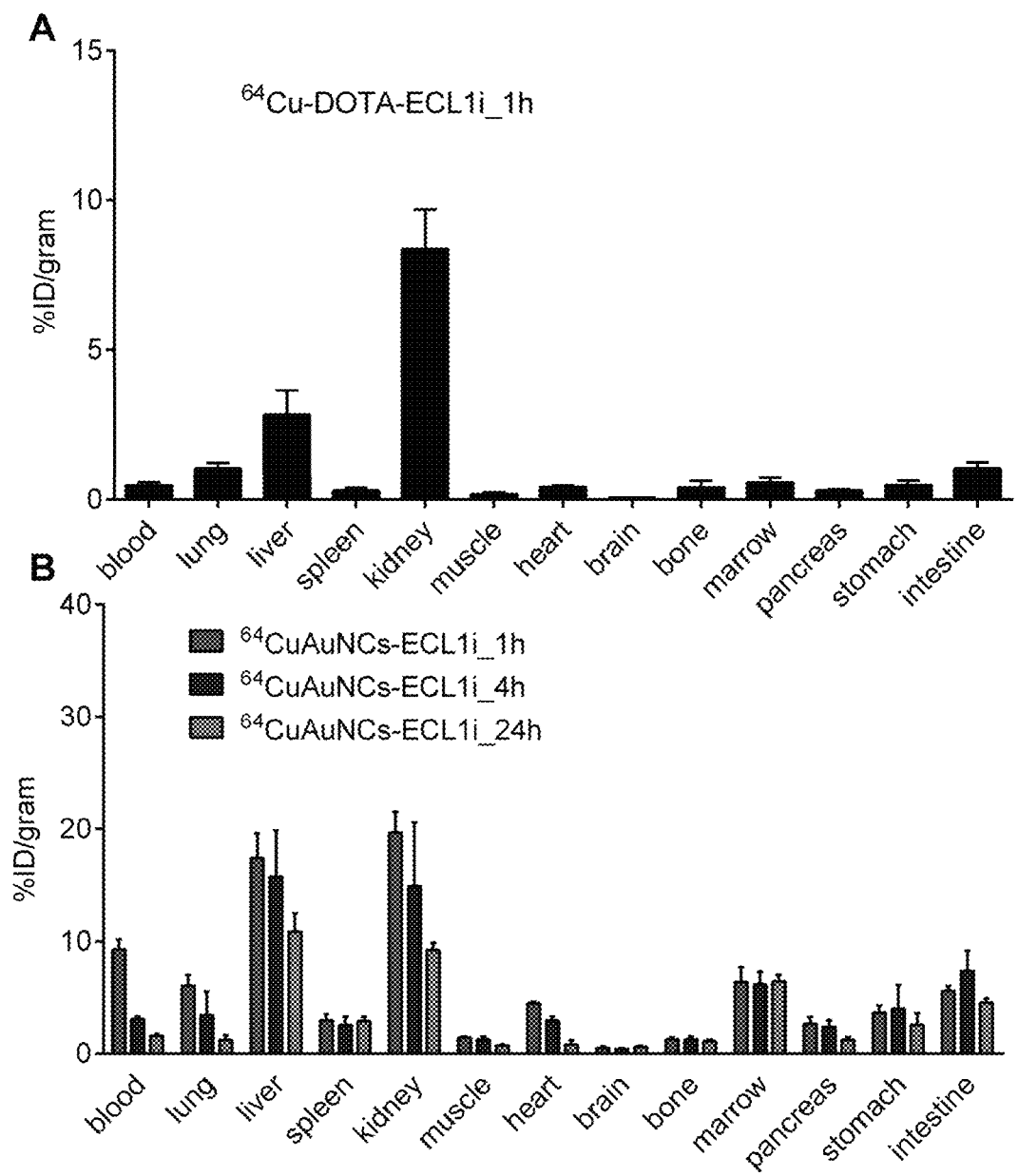
FIG. 6A-FIG. 6B is a series of bar graphs showing biodistribution studies in B6 wild type mice demonstrate different pharmacokinetics between $^{64}$Cu-DOTA-ECL1i and $^{64}$CuAuNCs-ECL1i.

CCR2 Imaging in Acute Lung Reperfusion Injury (See e.g., FIG. 6A).

Primary graft dysfunction PGD) is a significant cause of post lung transplant morbidity and is associated elevated CCL2 levels in BAL fluid[27,28]. PGD presents as respiratory failure immediately post-transplant, posing a broad differential diagnosis. Current therapy is non-specific—to intensify immunosuppression. It was shown that CCR2 is required for mobilization of inflammatory (CD11b$^+$ Ly6C$^{hi}$) monocytes and accumulation in lung allographs using a mouse model of lung transplantation[29]. We used $^{64}$Cu-DOTA-ECL1i to image this biology in the mouse transplant model. Transplantation of a wild type left lung into wild type mice resulted in intense signal in the left lung, consistent with CCR2-associated reperfusion injury (see e.g., FIG. 6A, red circle left). Whereas, a wild type lung transplanted into a CCR2$^{-/-}$ mouse shows minimal PET signal, suggesting abrogation of the reperfusion injury (see e.g., FIG. 6A, left) and that $^{64}$Cu-DOTA-ECL1i is specific for the detection of CCR2$^+$ inflammation in this model.

Summary of Data.

Figures 16A, 16B, 16C, 16D:
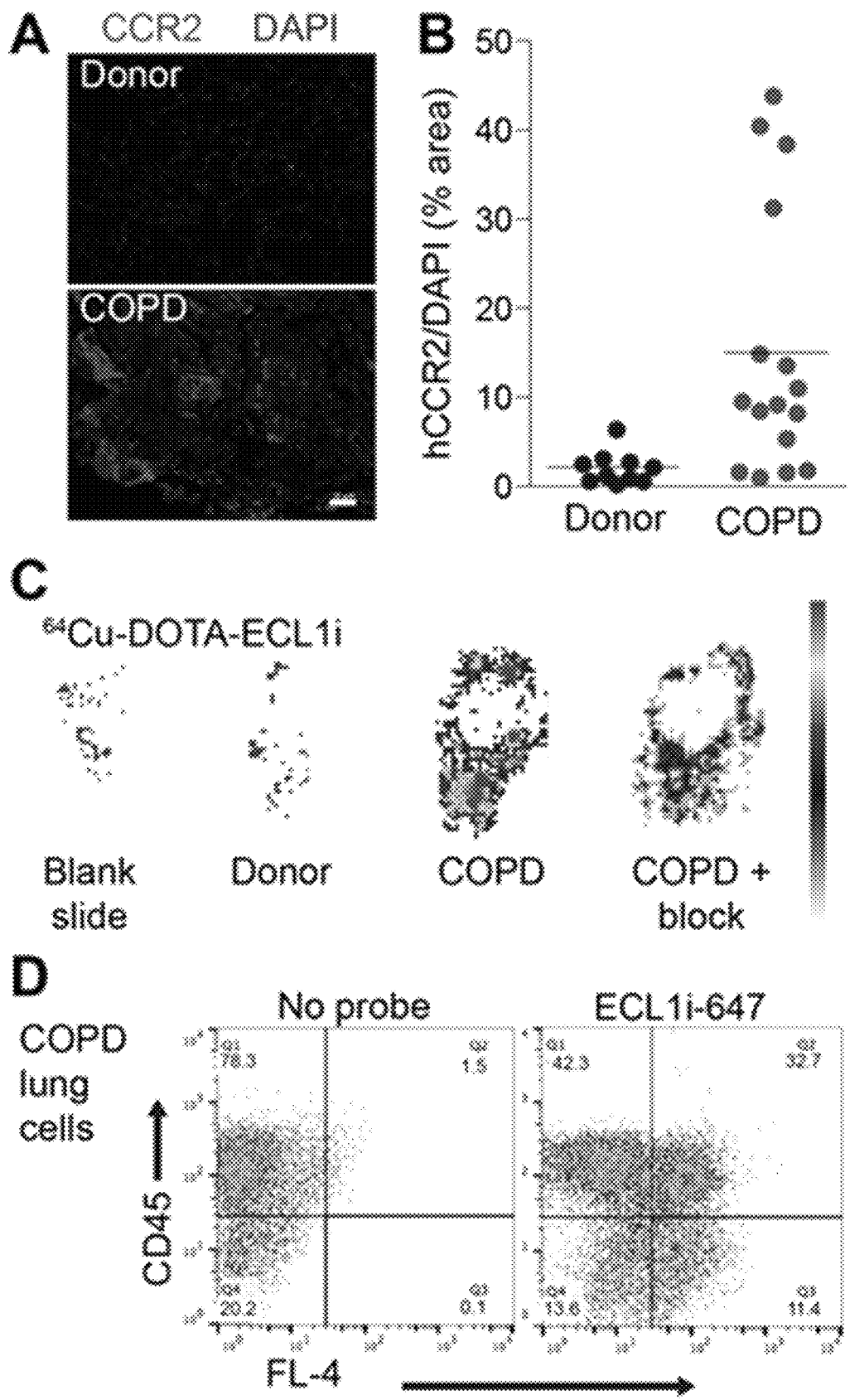
FIG. 16A-FIG. 16D is a series of images and plots showing CCR2 detection in lung tissue from subjects with COPD.

We demonstrate that: (1) peptide ECL1i is specific for CCR2 in vitro; (2) In an acute LPS lung injury model, $^{64}$Cu-DOTA-ECL1i PET imaging is sensitive to low dose injury, and specific, since it does not signal in CCR2$^{-/-}$ mice after LPS or acute reperfusion injury; a marked $^{64}$Cu-DOTA-ECL1i lung signal is extinguished by CCR2 antibody depletion. Moreover, in Example 4, we show data that ECL1i binds immune cells from human lung, ex vivo (see e.g., FIG. 16).

Example 4: Characterize the Sensitivity, Specificity and Stability of $^{64}$Cu-DOTA-ECL1i to Detect CCR2 in Mice Example 4.A. assesses $^{64}$Cu-DOTA-ECL1i sensitivity to detect CCR2 in mouse models of lung injury. Example 4.B. assesses $^{64}$Cu-DOTA-ECL1i specificity to detect CCR2 in mouse models of lung injury. Example 4.C. assesses CCR2 probe stability in target organs in an acute lung injury.

A. Rationale and Experimental Design.

Here, the relationship between the $^{64}$Cu-DOTA-ECL1i PET signal and the CCR2$^+$ cell burden in the lung will be determined by detection using flow cytometry. We will define a true positive (sensitivity)[90] as the presence of a PET signal when the burden of CCR2$^+$ cells is above a "normal" baseline (naïve mice). Our data suggests that $^{64}$Cu-DOTA-ECL1i PET can detect differences in naïve and inflammation induced by LPS doses that differed 5-fold (low vs. intermediate, FIG. 15D), but we have not quantified CCR2$^+$ cells. We will use acute and chronic lung inflammation models. Intratracheal LPS will serve as a reductionist model of acute injury, as there is no ideal mouse model of ARDS[83]. Paramyxovirus (Sendai) infection will serve as the chronic model. This is not intended as a model of COPD or asthma, despite shared features of chronic airway inflammation and mucous cell hyperplasia[87-89]. The experimental design will utilize the CCR2$^{RFP}$ reporter mice (C57BL/6, from D. Kreisel) to facilitate detection of CCR2$^+$ cells[91] and avoid underestimating CCR2$^+$ cells after transient receptor endocytosis[92]. These mice are heterozygous for CCR2 and have intact CCR2 responses[91]. We generated ECL1i-647 (Alexa Fluor 647) for co-detection of CCR2-RFP and to minimize autofluorescence in flow cytometry (see e.g., FIG. 16D, below). Image analysis will be optimized for lung volume and density by Drs. Chen and Shoghi as described[72,77,78,93,94]. The reproducibility of $^{64}$Cu-DOTA-ECL1i imaging in a single animal will be tested in the Paramyxovirus model using next-day studies. To visualize ECL1i-647 CCR2$^+$ cell localization and interactions, we will use 2-photon microscopy, performed by M. Miller (see letter) and D. Kreisel, who have previously imaged CCR2$^{RFP/+}$ mice[29,95].

A. Experimental Procedures (TABLE 3).

Shared control studies in examples 4.A. and 4.B. will minimize the number of PET/CT scans. For the acute lung injury studies, a naïve mouse will be studied and LPS dose titrated. Paramyxovirus will be provided with UV inactivated virus as a control[87-89]. Histology and gene expression studies will confirm inflammatory burden. Time points for evaluation are based on prior publications[25,85,89,96-98]. Flow cytometry will use standard surface markers to identify cell types, with expertise provided by immunologists Kreisel and Byers. PET images will read blind to the condition. For examples 4.A. and 4.B., at least 3-5 mice will be studied at each time point, means will be compared by t-test and ANOVA or with non-parametric testing as required. The percentage and type of CCR2$^+$/CCR2$^-$ cells and PET signal intensity will be analyzed by regression.

TABLE 3

Example 4A Experimental Design: ECL1i tracer sensitivity studies

| Mouse Strain | Injury Model | Tracer | Assay | Time-points | Example 4A: Goals |
|---|---|---|---|---|---|
| Wild type and CCR2$^{RFP/+}$ | Acute: naive vs. PBS vs. LPS | $^{64}$Cu-ECL1i; Fluor-ECL1i | PET, flow cytometry, histology | 2, 8, 24, 48, 144 h | Relationship between PET signal and lung CCR2+ cell burden in acute lung injury |
| Wild type and CCR2$^{RFP/+}$ | Chronic: inactivated SeV vs. SeV | $^{64}$Cu-ECL1i; Fluor-ECL1i | PET, flow cytometry, histology | 5, 12, 21, 49 d | Relationship between PET signal and lung CCR2+ cell burden in chronic lung injury, reproducibility of PET |
| CCR2$^{RFP/+}$ | naive vs. LPS | Fluor-ECL1i | 2-Photon microscopy | 2, 24 h | Localization of CCR2+/ECL1i+ cells |

B. Rationale and Experimental Design.

Figure 17:
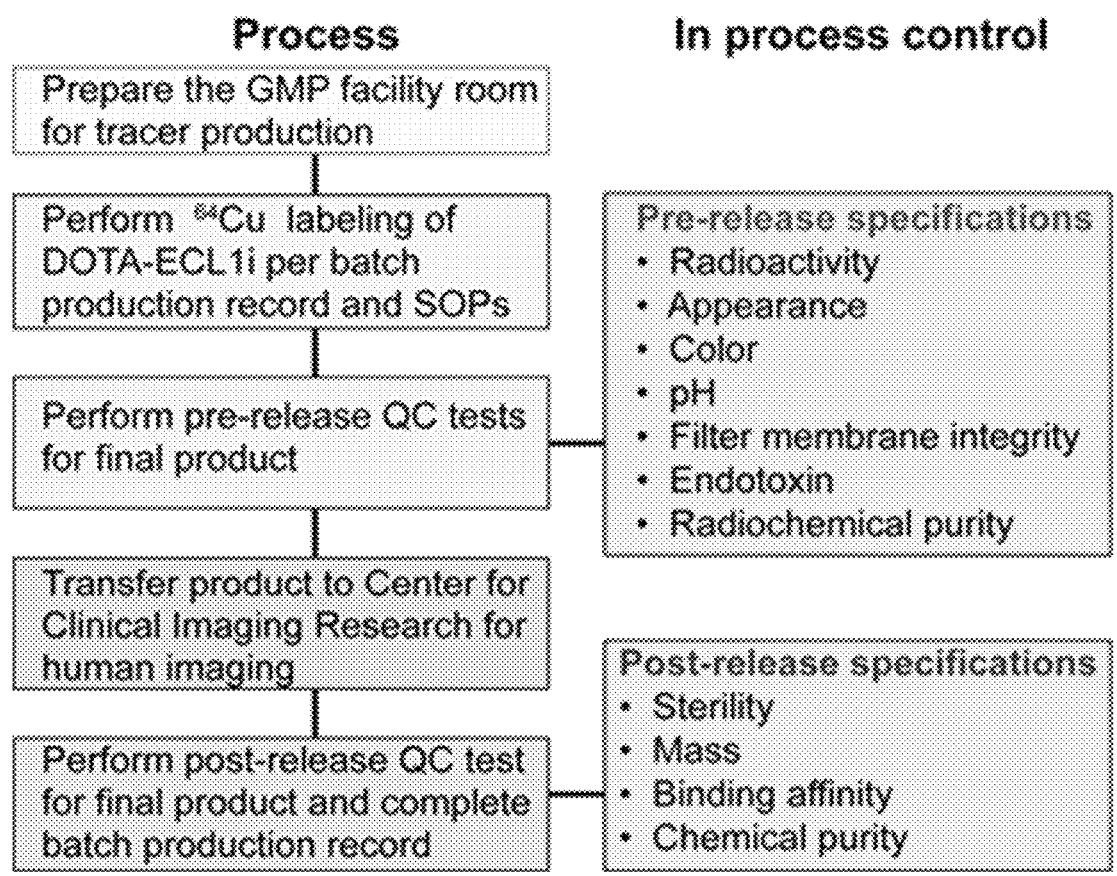
FIG. 17 is a flow chart showing the GMP preparation of $^{64}$Cu-DOTA-ECL1i.

Example 4.B. will determine the specificity of the $^{64}$Cu-DOTA-ECL1i PET signal to detect a CCR2$^+$ cell burden in the lung. Our data suggests that the ECL1i peptide specifically binds to CCR2 and we see an absence of $^{64}$Cu-DOTA-ECL1i PET signal in lungs of CCR2$^{-/-}$ mice subjected to LPS or reperfusion injury (see e.g., FIG. 15C, FIG. 17A). We propose three additional studies. First, we will test a scrambled ECL1i sequence in the radiolabeled and optical tracers (FKLTLCG; tested by C. Combadiere in vitro, not shown). Second, to monitor CCR2 molecular therapy we will study CCR2 antagonist our acute and chronic injury models, using RS504393 (Tocris), based efficacy in LPS lung injury and other models[26,99,100]. Third, since monocytes are often a dominant CCR2-expressing cell type and modulators of acute and chronic immune responses, we will determine the effect of monocyte depletion on imaging. We will use the MaFIA (macrophage Fas-induced apoptosis) transgenic mouse system[101] based on the Kreisel lab experience (data not shown) and reports of monocyte depletion in mouse lung disease and other models[34,101]. The transgene contains a Fas gene domain and eGFP reporter gene, driven by the colony stimulating factor promoter and activated by the drug AP20187. To image monocyte depletion, the LPS and lung transplant reperfusion injury models will be used, which have known monocyte responses[25,29,85].

B. Experimental Procedures (TABLE 4).

The magnitude of the $^{64}$Cu-DOTA-ECL1i/PET signal after the delivery of intratracheal recombinant mouse CCL2 (50 µg/mouse)[25] relative to the burden of CCR2$^+$ cells will first be identified by flow cytometry assay and compared in scrambled ECL1i studies. For CCR2 antagonist studies, we determine the effect of antagonist pre-treatment (LPS only) and post-injury treatment (LPS and chronic virus models) on PET signal. To follow monocyte depletion the MaFIA mouse will be bred with the CCR2RFP/+ mouse to take advantage of the reporters in each strain. Efficacy of monocyte/macrophage deletion will be confirmed using the GFP-YFP reporter in the transgenic cells and flow cytometry.

TABLE 4

Example 4B Experimental Design: tracer sensitivity studies.

| Mouse Strain | Injury Model | Tracer | Assay | Time-points | Example 4B: Goals |
|---|---|---|---|---|---|
| CCR2$^{RFP/+}$ | Naïve vs. CCL2 | $^{64}$Cu-ECL1i; Fluor-ECL1i | PET, flow cytometry, histology | 8, 24 h | Specificity of CCL2-stimulated CCR2 activity |
| Wild type and CCR2$^{RFP/+}$ | Naïve vs. CCL2, PBS vs. LPS | $^{64}$Cu-ECL1i; Fluor-ECL1i vs. scrambled | PET, flow cytometry, histology | 8, 24 h | Effect of scrambled ECL1i peptide on PET vs. CCR2$^+$ cells |
| Wild type and CCR2$^{RFP/+}$ | Acute PBS vs. LPS ± Antagonist | $^{64}$Cu-ECL1i; Fluor-ECL1i | PET, flow cytometry, histology | 2, 8, 24, 48, 144 h | Effect of pre/post antag. Rx on PET vs. CCR2$^+$ cells in acute inj. |
| MaFIA × CCR2$^{RFP/+}$ | naive vs. LPS and Lung Tx | $^{64}$Cu-ECL1i; Fluor-ECL1i | PET, flow cytometry, histology | 2, 24 h | Effect of monocyte depletion on PET vs. CCR2$^+$ cells |

C. Rationale, Experimental Design and Procedure.

We have demonstrated that the $^{64}$Cu-DOTA-ECL1i compound is stable for 1 h after incubation in mouse serum at 37° C. and in vivo in blood and lung after injected into a naïve mouse. However, it is possible that local lung and systemic inflammation may alter stability. Stability of Cu-DOTA-ECL1i during lung injury will be assessed in the LPS model with analysis of target organs (lung, liver, kidney and bone marrow) by HPLC and mass spectrometry. The stability of $^{64}$Cu-DOTA-ECL1i generated using GMP conditions will be tested in human serum.

Anticipated Results, Potential Problems, and Alternative Approaches.

These experiments will provide the strength of the relationship between the $^{64}$Cu-DOTA-ECL1i PET signal and the CCR2 cell burden. We expect to find that the tracer is relatively sensitive and very specific. One issue will to be to determine the lowest CCR2+ population detected by PET, and relate that to a CCR2$^+$ cell burden. To augment this determination we can measure CCL2 by ELISA. We expect that there will be a "false negative" condition i.e., a likelihood abnormal levels of CCR2$^+$ cells present when the PET signal is absent. To determine the pathologic effect of the CCR2 cell burden in this condition, we will examine histology and cytokine levels. Low PET signal may be due to the inability of the intravenously delivered tracer to access all CCR2$^+$ cells, including airspaces[25,26,85]. We will test this by BAL using γ-counting) and with parallel cell flow cytometry as we have done previously[102]. We expect that the level of CCR2$^+$ cells will track with lung inflammation in general, however, the cell type bearing CCR2 will likely differ between the acute and chronic models.

Evidence that DOTA-ECL1i-647 binds CCR2$^{RFP/+}$ cells or co-localizes with CCR2 antibodies will provide evidence of tracer specificity. We expect that peptide specificity will also be validated by use of a scrambled ECL1i, a CCR2 antagonist and monocyte depletion. The antagonist study is of interest as a therapy model. Failure to see an effect with RS504393 will lead trials of alternative antagonists (e.g., BMS CCR2 28) or CCR2 antibodies[25,85]. We expect that monocyte depletion will nearly abolish PET signals but have chosen only acute models that are known to be CCR2+ monocyte dominant. To study chronic inflammation in future studies we could apply use the MaFIA mice in the Paramyxovirus model. Difficulties with the MaFIA transgenic mice will lead us to use liposomal clodronate[103] or diphtheria toxin transgenic mice[104] for monocyte depletion.

Regarding stability, radiotracer degradation in the mouse injury models is not anticipated given the reproducible signal in mouse models. Peptide screening for predicted enzyme targets (ExPASy.org) showed rare enzyme cleavage sites (e.g., pepsin). If degradation is observed, we will generate the predicted products as HPLC standards to identify degraded forms, then alter target cleavage sites.

For the radiotracers that meet the criteria for success we will assess radiolabeling the peptide with $^{68}$Ga, a positron emitter with desirable nuclear properties ($t_{1/2}$=68 min, $β^{+}$% 89%, $E_{β+max}$: 1.92 MeV) produced by commercial available $^{68}$Ge/$^{68}$Ga generator, to expand the translation potential. Imaging with this radiotracer will be compared to $^{64}$Cu-DOTA-ECL1i in the mouse lung injury models. If ultimately human safety studies are satisfactory $^{68}$Ga-DOTA-ECL1i and resolution is retained with $^{68}$Ga, the lower radiation exposure and availability of the radionuclide may allow repeated scans in patients with ongoing symptoms to test therapeutic responses.

Example 5: Assess $^{64}$Cu-DOTA-ECL1i Binding to hCCR2 and Quantify CCR2 Activity in Human Lung Tissues Example 5.A. determines the sensitivity, specificity, and stability of $^{64}$Cu-DOTA-ECL1i to bind hCCR2 in cells. Example 5.B. evaluates the ability of ECL1i-based probes to detect CCR2 in human lung cells and tissues. Example 5.C. describes a Phase 0/Early Phase 1 trial to determine $^{64}$Cu-DOTA-ECL1i safety and dosimetry in healthy volunteers.

A. Rationale and Experimental Design.

The goal of this example is to assess the performance of the ECL1i tracer in human cells. The amino acid sequence of the CCR2 in the region of the extracellular loop 1 used to design ECL1i is >95% conserved in the mouse and human. Our data using autoradiography suggest that $^{64}$Cu-DOTA-ECL1i binds human CCR2 in tissues (see e.g., FIG. 16C, below). To measure the specific binding of ECL1i to human CCR2 we have produced a human CCR2 expression plasmid to generate a stable cell line in human HEK293 cells. The approach has been used our group to study ligand binding for PET radiotracers[105] and will be used to develop an affinity binding assay for both experimental and post-release quality control (QC) of $^{64}$Cu-DOTA-ECL1i. As in mice, we will test the specificity using the scrambled ECL1i sequence and the stability using HPLC and mass spectroscopy to characterize the performance of $^{64}$Cu-DOTA-ECL1i in human cells.

A. Experimental Procedures.

A HEK293-hCCR2 stable cell line will be validated at the RNA and protein levels, compared to a control cell line transfected with an empty vector. We will generate a set of HEK293 cells expressing additional human chemokine receptors (e.g., CCR1, CCR5, CXCR4) or obtain these from C. Combadiere[106]. For the affinity binding assays $^{64}$Cu-DOTA-ECL1i (vs. the scrambled version) will be incubated with the cells in a range of concentrations in the absence or presence of excess non-radiolabeled Cu-DOTA-ECL1i and counted in a □-counter to calculate an $IC_{50}$. An SOP will be developed and the assay applied as a QC measure for $^{64}$Cu-DOTA-ECL1i production. Parallel studies will be performed with and ECL1i-647. Stability studies of $^{64}$Cu-DOTA-ECL1i will be performed in human serum as described in Example 4C.

B. Rationale and Experimental Design.

The goal of this example is to characterize the binding of $^{64}$Cu-DOTA-ECL1i in normal and diseased lung tissues. Studies will also validate CCR2 in a lung disease population. We will determine the capacity of $^{64}$Cu-DOTA-ECL1i and ECL1i-647 to bind hCCR2 using autoradiography, flow cytometry and two-photon microscopy. We take advantage of a substantial, established tissue biorepository previously used for COPD studies[33,87,88,107]. We have chosen COPD tissues this and other reasons: (1) CCL2/CCR2 is present in BAL of subjects with asthma[34,108,109], but to validate CCR2 expression in interstitial tissues by transbronchial biopsy is potentially risky for this population. (2) Levels of CCL2/CCR2 are also high in PGD post-lung transplantation, but despite routine bronchoscopy in this group, an unstable status is not ideal for tissue validation studies. (3) Elevated CCL2/CCR2 in COPD BAL and in tissues resected for lung cancer[30-32], suggested we could use a similar approach.

ECL1i Binds hCCR2 in Lungs from Subjects with COPD.

We found that tissues from lungs explanted from subjects with severe COPD (removed for lung transplantation) have a mean increase in levels of CCR2 expression, compared to normal donated lungs ("donor"), by immunostaining (see e.g., FIG. 16A, FIG. 16B) and a similar pattern in RNA samples (not shown). There were three CCR2 phenotypes (high, intermediate, normal), with implications for future therapies. Importantly, autoradiography of lung sections on slides using $^{64}$Cu-DOTA-ECL1i showed marked increased binding in COPD samples compared to normal donor (see e.g., FIG. 16C). Our tissue bank also includes cells digested from lung for flow cytometry studies. In the reported studies, we found that ECL1i bound a population of CD45$^+$ immune cells in COPD lung (see e.g., FIG. 16C). We obtain approximately 6-8 explanted lungs per year from COPD subjects. We propose to also examine lung tissue incubated with ECL1i-647 and cells specific antibodies using two-photon microscopy to localize ECL1i.

B. Experimental Procedures.

We will use explanted lung samples available from over 30 unique subjects with advanced COPD that underwent lung transplantation and 15 tissues from non-COPD subjects donated for transplantation. Immunostaining with CCR2 and standard antibodies will identify the location and extent of CCR2$^+$ classical monocytes. Parallel samples of flow cytometry using antibodies and DOTA-ECL1i-647 will quantify and characterize CCR2-expressing cells (as in FIG. 3C, FIG. 15, FIG. 16D). At least 4 different regions from each lung are banked for analysis to assess for intra-organ variability. Parallel samples will be used for $^{64}$Cu-DOTA-ECL1i autoradiograph and binding then quantified. These will be correlated with antibody-based data. For 2-photon microscopy, we will incubate fresh human COPD lung tissue with ECL1i-647 and cell-type specific antibodies to complement binding observe by autoradiographs and immunostaining[110].

Anticipated Results, Potential Problems and Alternative Approaches.

Receptor binding assays rely on adequate levels of cell surface CCR2 expression. If levels are low, we will generate and select cell clones with high levels and confirm surface binding using CCR2 antibodies. Primary peripheral blood human monocytes have high surface CCR2 expression and may serve as an alternative to cell lines for assays[111,112].

In studies of tissue from COPD subjects, we expect to find a CCR2 expression within the interstitial compartment (out of reach of bronchoscopy or sputum sampling) on multiple cell types. We also predict that expression will vary among different samples of the same lung, confirming the overall approach that we are taking and highlighting the problem inherent in sampling. The variation in levels of CCR2 expression and $^{64}$Cu-DOTA-ECL1i binding will support the importance of using PET imaging as a diagnostic test. The tissue bank also includes lung samples from a range of COPD (GOLD 0-IV), making it possible to determine if the CCR2 levels are related to disease severity. Moreover, a large number of samples from subjects with idiopathic pulmonary fibrosis (IPF) are also available. Increased numbers of CCR2 cells are reported in IPF[18,39-41], which may serve as an alternative population for testing the ECL1i tracer in human tissue.

Example 6: Translate $^{64}$Cu-DOTA-ECL1i in a Phase 0/Early Phase 1 Trial

Example 6.A performs animal toxicology and dosimetry studies of $^{64}$Cu-DOTA-ECL1i. Example 6.B. develops chemistry, manufacturing, and controls (CMC) and standard operating procedures (SOPs) for $^{64}$Cu-DOTA-ECL1i production, and submit an eIND application.

A. Rationale and Experimental Design.

This example will generate toxicology and dosimetry studies required for an eIND application. We will conduct the toxicology study in mice as previously performed. Dosimetry will be performed using standard protocols and analyzed by our investigator with specific expertise in this area, R. Laforest[70-74]. Our group has extensive experience in performing such studies and a core with dedicated personnel and equipment to perform dosimetry studies in a routine fashion.

A. Experimental Procedures.

Rodent toxicity studies. For toxicology studies, non-radioactive copper labeled Cu-DOTA-ECL1i will be produced following the protocol for $^{64}$Cu labeled production. A single i.v. injection of 100-times the expected human dose per body surface area will be used. Mice, 8-10 weeks of age of both sexes will evaluated over 14 days to determine the systemic toxicity and organ toxicity by gross necropsy and histology, hematology, blood for clinical pathology analysis, urine analysis and weight loss analysis. Detailed analysis of the data will be provided for an eIND application.

Animal dosimetry and estimation for humans. Animal biodistribution will be designed according to our previous experience using $^{64}$Cu-labeled agents with fast renal clearance and performed to determine the percent injected dose per gram of tissue (% ID/g) in major organs (>20) at multiple time points after $^{64}$Cu-DOTA-ECL1i injection[74, 75]. The results will be scaled to human by the relative organ weight method[112]. Time-activity curves will be created and radiotracer uptake or clearance functions will be analyzed. Integration of those functions will provide organ residence times. An additional group of animals will be kept in metabolic cages to determine the excretion.

Human radiation dose estimates. This will be calculated from the mouse dosimetry data, residence times and for the standard human male model using OLINDA-EXE (version 1.1) as described[113].

B. Rationale and Experimental Design.

The purpose of this example is to develop protocols for production of the radiotracer and complete the chemistry manufacturing and controls (CMC) and standard operating procedures (SOPs) for an eIND application for human use. We will take advantage of our extensive experience in this regard and the use of our ISO 7 GMP facility, nuclear pharmacy and cyclotron production facility (see Resources). Members of the Liu lab will work closely with investigator S. Schwarz to develop new SOPs and for scale-up production to prepare eIND documents, together with toxicology and dosimetry data from Example 6.A.

B. Experimental Procedures.

The production of DOTA-ECL1i following SOPs under cGMP conditions will be scaled up and full QC characterization will be performed. Stability of DOTA-ECL1i as raw material will be monitored to provide guidance about the expiration of the probe. Validation runs of $^{64}$Cu labeling with full process and quality control will be performed in the cGMP facility following batch production record and SOPs for eIND submission.

C. Rationale and Experimental Design.

The goals of this example are to determine human safety, biodistribution and radiation dosimetry of $^{64}$Cu-DOTA-ECL1i. This study will be a single center, open-label baseline controlled imaging study. Planned recruitment will be for 18 subjects with a final goal to study 12 for dosimetry determination based on our prior studies[70,72-74]. We will include non-smokers and cigarette smokers with normal pulmonary function (spirometry) to determine if systemic inflammation that is well known in smokers[113,114] alters dosimetry[115,116]. Potential study populations with acute and chronic lung disease are often cigarette smokers.

C. Experimental Procedures.

Regulatory approval: The second 6 months of year 2 will be devoted obtaining FDA approval via the eIND mechanism and IRB and RDRC approvals at Washington University.

Research subjects. The safety and dosimetry of $^{64}$Cu-DOTA-ECL1i will be tested in 12 healthy volunteer subjects using a single intravenous dosage. Non-smoking (6) and tobacco smoking, with normal lung spirometry (6) will be included. A total of 18 subjects will be recruited with an expect non-completion rate of 20%. Our research coordinator will recruit subjects with assistance from the Volunteers for Health Program at the School of Medicine (https://vfh.wustl.edu/), an approach that has been successful over the past 15 years. Subjects will be contacted by telephone and interviewed for suitability and inclusion/exclusion criteria. These will be as follows: Inclusion: Healthy man or woman, any race or ethnicity, age 21-45 years old; screening FEV1 and FVC>90% of predicted in smokers; capable of lying still, supine within the PET/CT scanner for ~1.5 hours and following instructions for breathing protocol during the CT portion; a BMI<35 and able and willing to give informed consent. Exclusion: Pregnancy (confirmed by serum hCG test); lactation; active menstruation; active symptoms or history of cardiopulmonary, diabetes, hepatic or renal disease; current use of prescription medications; history of illicit drug use within the past year; enrollment in another research study of an investigational drug.

Figure 18:
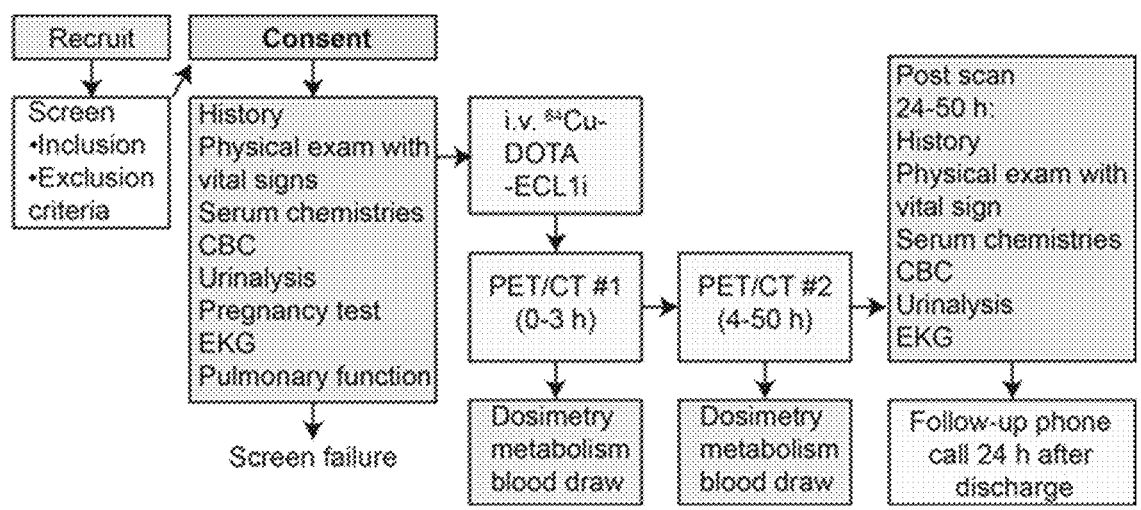
FIG. 18 is a flow chart showing the Phase 0/Early Phase 1 safety and dosimetry study.

General protocol (see e.g., FIG. 18). Once recruited, consent forms will be provided the subjects for review at least 24 h prior to the studies. Subjects will be met in the Center for Clinical Imagining and Research (CCIR), within Barnes-Jewish Hospital. Consent will be obtained and a history and physical exam performed by a physician investigator. For safety analysis subjects will undergo vital sign measurement and testing as in FIG. 18. Results of laboratory tests (complete blood count, comprehensive metabolic panel, and urinalysis, plus pregnancy test for women and spirometry for cigarette smokers) will be obtained prior to injection. Subjects with abnormal tests will be withdrawn and compensated.

$^{64}$Cu-DOTA-ECL1i injection and imaging protocol. The radiotracer will be prepared in the GMP facility as described in Example 6B. A pre-dosimetry dose estimate is 0.7 µg/kg. A peripheral intravenous catheter will be place. Vital signs will be obtained pre-injection (within 30 min prior to injection of $^{64}$Cu-DOTA-ECL1i), 10-15 min post injection; and at completion of each imaging cycle. Volunteers will be undergo whole-body PET/CT imaging at a paired times between 0 and 50 h post injection to calculate human dosimetry based on biodistribution of this $^{64}$Cu-based, peptide containing radiotracer. Four groups (G1-4) of 3 patients each will sample the 50 h post injection period with 2 scans each: G1 0-3 h and 4-6 h; G2 0-3 h and 22-28 h; G3 4-6 h and 22-28 h G4 1-3 h and 46-50 h. Although allergic or other immediate adverse reactions are not anticipated, subjects will be monitored for at least one-hour post injection in an area where emergency equipment is available. The study will terminate if subjects experience any sign of toxicity or tracer-associated discomfort. Subjects will remain in the imaging unit for serial exams or return for subsequent scan, post-scan testing, and compensation. Subject status will be determined in a follow-up phone call at one day after the last scan.

PET/CT image acquisition. PET/CT acquisition will include a CT scan for attenuation correction with the patient supine after intravenous administration of $^{64}$Cu-DOTA-ECL1i. The CT will consist of a 10-20 second topogram for determining correct anatomical positioning followed by a spiral CT at 50 mAs (or Caredose calculated dose if less than 50 mAs) and 120 kVp. Average CT scan time is 15-30 seconds to acquire a 5-mm-slices. Immediately after the attenuation CT scan, emission images from the top of the skull through the upper thighs will be obtained (1-10 min per bed position).

Image analysis, calculation of biodistribution and radiation dosimetry: Organ activity concentration will be measured on the most visible organs on the PET images. The average activity concentration measured in organs will be converted to percent injected dose[117]. Time activity curves combining the percent-injected dose for all subjects will then be created. Activity residence times for each observed organ will then be calculated and corrected for radioactive decay. The urinary bladder excretion is calculated using an established model[118] Radiation doses estimates will then be calculated using the OLINDA/EXM (version 1.1)[113] in the standard human male model.

Anticipated Results, Potential Problems and Alternative Approaches.

Pre-clinical studies are expected to have minimal adverse effects, although toxicity is unpredictable. If significant toxicity is observed in mice, we will attempt to isolate the source of toxicity. One source of peptide toxicity may be charge. Change will be reduced by N-acetylation and C-amidation of the ECL1i peptide, (which will not affect DOTA conjugation). Also, acetylation may reduce toxicity as a closer mimic of native protein, since 85% of human proteins are acetylated[117].

Because the manufacturing methods are well established, we do not expect problems with scale up production and radiolabeling. Based on prior experience, we anticipate an approximate 10% failure rate in $^{64}$Cu or 64Cu-DOTA-ECL1i production. If this is the case, we have included reimbursement funds for recruited subjects who are unable to complete the study due to this technical issue.

We will design our human dosimetry protocol based on mouse dosimetry. We expect that the kidney or bladder wall will be the radiation dose-limiting organ. Given we will be administering <100 μg of product, in accordance with eIND guidelines, we do not expect to observe serious toxic effects but are aware of potential CCR2 antagonism of ECL1i. Consequently, subjects will be monitored for at least one-hour post injection in an area where emergency equipment is available. In the event of higher than expected radiation dose to the kidneys or bladder wall, dose reduction strategy in humans will include appropriate patient hydration and regular bladder voiding. We will immediately halt the study if there are any significantly symptoms or laboratory abnormalities and notify the FDA and IRB.

Future Directions: Proposed Phase 1 $^{64}$Cu-DOTA-ECL1i Safety Studies in Subjects with Lung Inflammation.

Once our early Phase 1 trial confirms safety in healthy volunteers, we will evaluate the performance of $^{64}$Cu-DOTA-ECL1i in target populations for later Phase 1 studies, where knowing the inflammatory burden will aid in clinical decision making. We are considering two potential study populations for safety assessment. First, $^{64}$Cu-DOTA-ECL1i PET imaging following segmental endotoxin challenge delivered by bronchoscopy[76-78]. Post-endotoxin bronchoscopy and BAL permits potential assessment of CCR2$^+$ cells in the airspace. A second consideration are individuals with severe COPD awaiting lung transplantation, who offer the potential to assay the CCR2$^+$ cell burden in explanted lungs for comparison to the intensity of PET image. Subjects with COPD undergoing surgery for lung nodules may also provide tissue for assessing CCR2$^+$ cell status, though CCR2$^+$ macrophage may infiltrate the tumor[119]. The unstable nature of patients with respiratory failure groups such as those with ARDS and resolving vs. persistent inflammation or the post lung transplant patient with PGD may be too high risk for phase 1 studies.

REFERENCES FOR EXAMPLES 3-6

1. Byers D E, Holtzman M J. Alternatively activated macrophages and airway disease. Chest. 2011; 140(3):768-74. PMCID: PMC3168852.
2. Deshane J S, Redden D T, Zeng M, Spell M L, Zmijewski J W, Anderson J T, Deshane R J, Gaggar A, Siegal G P, Abraham E, Dransfield M T, Chaplin D D. Subsets of airway myeloid-derived regulatory cells distinguish mild asthma from chronic obstructive pulmonary disease. J Allergy Clin Immunol. 2015; 135(2):413-24 e15. PMCID: PMC4323991.
3. Lambrecht B N, Hammad H. The immunology of asthma. Nat Immunol. 2015; 16(1):45-56.
4. McAleer J P, Kolls J K. Directing traffic: IL-17 and IL-22 coordinate pulmonary immune defense. Immunol Rev. 2014; 260(1):129-44. PMCID: PMC4066195.
5. Charo I F, Ransohoff R M. The many roles of chemokines and chemokine receptors in inflammation. N Engl J Med. 2006; 354(6):610-21.
6. Tomankova T, Kriegova E, Liu M. Chemokine receptors and their therapeutic opportunities in diseased lung: far beyond leukocyte trafficking. Am J Physiol Lung Cell Mol Physiol. 2015; 308(7):L603-18.
7. Tsou C L, Peters W, Si Y, Slaymaker S, Aslanian A M, Weisberg S P, Mack M, Charo I F. Critical roles for CCR2 and MCP-3 in monocyte mobilization from bone marrow and recruitment to inflammatory sites. J Clin Invest. 2007; 117(4):902-9. PMCID: PMC1810572.
8. Robays L J, Maes T, Lebecque S, Lira S A, Kuziel W A, Brusselle G G, Joos G F, Vermaelen K V. Chemokine receptor CCR2 but not CCR5 or CCR6 mediates the increase in pulmonary dendritic cells during allergic airway inflammation. J Immunol. 2007; 178(8):5305-11.
9. Charo I F, Peters W. Chemokine receptor 2 (CCR2) in atherosclerosis, infectious diseases, and regulation of T-cell polarization. Microcirculation. 2003; 10(3-4):259-64.
10. Rose C E, Jr., Sung S S, Fu S M. Significant involvement of CCL2 (MCP-1) in inflammatory disorders of the lung. Microcirculation. 2003; 10(3-4):273-88.
11. Christensen P J, Du M, Moore B, Morris S, Toews G B, Paine R, 3rd. Expression and functional implications of CCR2 expression on murine alveolar epithelial cells. Am J Physiol Lung Cell Mol Physiol. 2004; 286(1):L68-72.
12. Lundien M C, Mohammed K A, Nasreen N, Tepper R S, Hardwick J A, Sanders K L, Van Horn R D, Antony V B. Induction of MCP-1 expression in airway epithelial cells: role of CCR2 receptor in airway epithelial injury. J Clin Immunol. 2002; 22(3):144-52.
13. Serbina N V, Pamer E G. Monocyte emigration from bone marrow during bacterial infection requires signals mediated by chemokine receptor CCR2. Nat Immunol. 2006; 7(3):311-7.
14. Tacke F, Randolph G J. Migratory fate and differentiation of blood monocyte subsets. Immunobiology. 2006; 211(6-8):609-18.
15. Murray P J, Wynn T A. Protective and pathogenic functions of macrophage subsets. Nat Rev Immunol. 2011; 11(11):723-37. PMCID: PMC3422549.
16. Geissmann F, Manz M G, Jung S, Sieweke M H, Merad M, Ley K. Development of monocytes, macrophages, and dendritic cells. Science. 2010; 327(5966):656-61. PMCID: PMC2887389.
17. Lin K L, Suzuki Y, Nakano H, Ramsburg E, Gunn M D. CCR2+ monocyte-derived dendritic cells and exudate macrophages produce influenza-induced pulmonary immune pathology and mortality. J Immunol. 2008; 180(4):2562-72.
18. Okuma T, Terasaki Y, Kaikita K, Kobayashi H, Kuziel W A, Kawasuji M, Takeya M. C-C chemokine receptor 2 (CCR2) deficiency improves bleomycin-induced pulmonary fibrosis by attenuation of both macrophage infiltration and production of macrophage-derived matrix metalloproteinases. J Pathol. 2004; 204(5):594-604.
19. Hildebrandt G C, Duffner U A, Olkiewicz K M, Corrion L A, Willmarth N E, Williams D L, Clouthier S G, Hogaboam C M, Reddy P R, Moore B B, Kuziel W A, Liu C, Yanik G, Cooke K R. A critical role for CCR2/MCP-1 interactions in the development of idiopathic pneumonia syndrome after allogeneic bone marrow transplantation. Blood. 2004; 103(6):2417-26.
20. Rosseau S, Hammerl P, Maus U, Walmrath H D, Schutte H, Grimminger F, Seeger W, Lohmeyer J. Phenotypic characterization of alveolar monocyte recruitment in acute respiratory distress syndrome. Am J Physiol Lung Cell Mol Physiol. 2000; 279(1):L25-35.
21. Bhatia M, Zemans R L, Jeyaseelan S. Role of chemokines in the pathogenesis of acute lung injury. Am J Respir Cell Mol Biol. 2012; 46(5):566-72. PMCID: PMC3361356.
22. Shen Y, Wang D, Wang X. Role of CCR2 and IL-8 in acute lung injury: a new mechanism and therapeutic target. Expert Rev Respir Med. 2011; 5(1):107-14.
23. Steinmuller M, Srivastava M, Kuziel W A, Christman J W, Seeger W, Welte T, Lohmeyer J, Maus U A. Endotoxin induced peritonitis elicits monocyte immigration into the lung: implications on alveolar space inflammatory responsiveness. Respir Res. 2006; 7:30. PMCID: PMC1388208.
24. Speyer C L, Gao H, Rancilio N J, Neff T A, Huffnagle G B, Sarma J V, Ward P A. Novel chemokine responsiveness and mobilization of neutrophils during sepsis. Am J Pathol. 2004; 165(6):2187-96. PMCID: PMC1618724.
25. Maus U, von Grote K, Kuziel W A, Mack M, Miller E J, Cihak J, Stangassinger M, Maus R, Schlondorff D, Seeger W, Lohmeyer J. The role of CC chemokine receptor 2 in alveolar monocyte and neutrophil immigration in intact mice. Am J Respir Crit Care Med. 2002; 166(3): 268-73.
26. Yang D, Tong L, Wang D, Wang Y, Wang X, Bai C. Roles of CC chemokine receptors (CCRs) on lipopolysaccharide-induced acute lung injury. Respir Physiol Neurobiol. 2010; 170(3):253-9.
27. Meloni F, Cascina A, Paschetto E, Marone Bianco A, Morosini M, Pellegrini C, Fietta A, Vitulo P, Pozzi E, Vigano M. Monocyte chemoattractant protein-1 levels in bronchioalveolar lavage fluid of lung-transplanted patients treated with tacrolimus as rescue treatment for refractory acute rejection. Transplant Proc. 2003; 35(4): 1523-6.
28. Belperio J A, Keane M P, Burdick M D, Lynch J P, 3rd, Xue Y Y, Berlin A, Ross D J, Kunkel S L, Charo I F, Strieter R M. Critical role for the chemokine MCP-1/CCR2 in the pathogenesis of bronchiolitis obliterans syndrome. J Clin Invest. 2001; 108(4):547-56. PMCID: PMC209398.
29. Gelman A E, Okazaki M, Sugimoto S, Li W, Kornfeld C G, Lai J, Richardson S B, Kreisel F H, Huang H J, Tietjens J R, Zinselmeyer B H, Patterson G A, Miller M J, Krupnick A S, Kreisel D. CCR2 regulates monocyte recruitment as well as CD4 T1 allorecognition after lung transplantation. Am J Transplant. 2010; 10(5):1189-99. PMCID: PMC3746750.
30. Capelli A, Di Stefano A, Gnemmi I, Balbo P, Cerutti C G, Balbi B, Lusuardi M, Donner C F. Increased MCP-1 and MIP-1beta in bronchioalveolar lavage fluid of chronic bronchitis. Eur Respir J. 1999; 14(1):160-5.
31. de Boer W I, Sont J K, van Schadewijk A, Stolk J, van Krieken J H, Hiemstra P S. Monocyte chemoattractant protein 1, interleukin 8, and chronic airways inflammation in COPD. J Pathol. 2000; 190(5):619-26.
32. Traves S L, Culpitt S V, Russell R E, Barnes P J, Donnelly L E. Increased levels of the chemokines GROalpha and MCP-1 in sputum samples from patients with COPD. Thorax. 2002; 57(7):590-5. PMCID: PMC1746378.
33. Barrow A D, Palarasah Y, Bugatti M, Holehouse A S, Byers D E, Holtzman M J, Vermi W, Skjodt K, Crouch E, Colonna M. OSCAR Is a Receptor for Surfactant Protein D That Activates TNF-alpha Release from Human CCR2+ Inflammatory Monocytes. J Immunol. 2015; 194 (7):3317-26. PMCID: PMC4369396.
34. Lee Y G, Jeong J J, Nyenhuis S, Berdyshev E, Chung S, Ranjan R, Karpurapu M, Deng J, Qian F, Kelly E A, Jarjour N N, Ackerman S J, Natarajan V, Christman J W, Park G Y. Recruited Alveolar Macrophages, in Response to Airway Epithelial-derived MCP-1/CCL2, Regulate Airway Inflammation and Remodeling in Allergic Asthma. Am J Respir Cell Mol Biol. 2014.
35. Kim J, Kim W, Le H T, Moon U J, Tran V G, Kim H J, Jung S, Nguyen Q T, Kim B S, Jun J B, Cho H R, Kwon B. IL-33-induced hematopoietic stem and progenitor cell mobilization depends upon CCR2. J Immunol. 2014; 193(7):3792-802.
36. Prado R Q, Bertolini T B, Pineros Alvarez A R, Gembre A F, Ramos S G, Silva C L, Borges M C, Bonato V L. Attenuation of experimental asthma by mycobacterial protein combined with CpG requires a TLR9-dependent IFN-gamma-CCR2 signaling circuit. Clin Exp Allergy. 2015.
37. Gonzalo J A, Lloyd C M, Wen D, Albar J P, Wells T N, Proudfoot A, Martinez A C, Dorf M, Bjerke T, Coyle A J, Gutierrez-Ramos J C. The coordinated action of CC chemokines in the lung orchestrates allergic inflammation and airway hyperresponsiveness. J Exp Med. 1998; 188 (1):157-67. PMCID: PMC2525544.
38. Stafford S, Li H, Forsythe P A, Ryan M, Bravo R, Alam R. Monocyte chemotactic protein-3 (MCP-3)/fibroblast-induced cytokine (FIC) in eosinophilic inflammation of the airways and the inhibitory effects of an anti-MCP-3/FIC antibody. J Immunol. 1997; 158(10):4953-60.
39. Sun L, Louie M C, Vannella K M, Wilke C A, LeVine A M, Moore B B, Shanley T P. New concepts of IL-10-induced lung fibrosis: fibrocyte recruitment and M2 activation in a CCL2/CCR2 axis. Am J Physiol Lung Cell Mol Physiol. 2011; 300(3):L341-53. PMCID: PMC3064283.
40. Moore B B, Kolodsick J E, Thannickal V J, Cooke K, Moore T A, Hogaboam C, Wilke C A, Toews G B. CCR2-mediated recruitment of fibrocytes to the alveolar space after fibrotic injury. Am J Pathol. 2005; 166(3):675-84. PMCID: PMC1780139.
41. Emad A, Emad V. Elevated levels of MCP-1, MIP-alpha and MIP-1 beta in the bronchioalveolar lavage (BAL) fluid of patients with mustard gas-induced pulmonary fibrosis. Toxicology. 2007; 240(1-2):60-9.
42. Martinu T, Gowdy K M, Nugent J L, Sun J, Kinnier C V, Nelson M E, Lyes M A, Kelly F L, Foster W M, Gunn M D, Palmer S M. Role of C-C motif ligand 2 and C-C motif receptor 2 in murine pulmonary graft-versus-host disease after lipopolysaccharide inhalations. Am J Respir Cell Mol Biol. 2014; 51(6):810-21. PMCID: PMC4291544.
43. Osterholzer J J, Curtis J L, Polak T, Ames T, Chen G H, McDonald R, Huffnagle G B, Toews G B. CCR2 mediates conventional dendritic cell recruitment and the formation of bronchovascular mononuclear cell infiltrates in the lungs of mice infected with *Cryptococcus neoformans*. J Immunol. 2008; 181(1):610-20. PMCID: PMC2735104.
44. Boring L, Gosling J, Cleary M, Charo I F. Decreased lesion formation in CCR2−/− mice reveals a role for chemokines in the initiation of atherosclerosis. Nature. 1998; 394(6696):894-7.
45. Kaikita K, Hayasaki T, Okuma T, Kuziel W A, Ogawa H, Takeya M. Targeted deletion of CC chemokine receptor 2 attenuates left ventricular remodeling after experimental myocardial infarction. Am J Pathol. 2004; 165(2): 439-47. PMCID: PMC1618584.
46. Abdi R, Means T K, Ito T, Smith R N, Najafian N, Jurewicz M, Tchipachvili V, Charo I, Auchincloss H, Jr., Sayegh M H, Luster A D. Differential role of CCR2 in islet and heart allograft rejection: tissue specificity of chemokine/chemokine receptor function in vivo. J Immunol. 2004; 172(2):767-75.
47. Lu X, Kang Y. Chemokine (C-C motif) ligand 2 engages CCR2+ stromal cells of monocytic origin to promote breast cancer metastasis to lung and bone. J Biol Chem. 2009; 284(42):29087-96. PMCID: PMC2781454.
48. Leuschner F, Dutta P, Gorbatov R, Novobrantseva T I, Donahoe J S, Courties G, Lee K M, Kim J I, Markmann J F, Marinelli B, Panizzi P, Lee W W, Iwamoto Y, Milstein S, Epstein-Barash H, Cantley W, Wong J, Cortez-Retamozo V, Newton A, Love K, Libby P, Pittet M J, Swirski F K, Koteliansky V, Langer R, Weissleder R, Anderson D G, Nahrendorf M. Therapeutic siRNA silencing in inflammatory monocytes in mice. Nat Biotechnol. 2011; 29(11): 1005-10. PMCID: PMC3212614.
49. Izikson L, Klein R S, Charo I F, Weiner H L, Luster A D. Resistance to experimental autoimmune encephalomyelitis in mice lacking the CC chemokine receptor (CCR)2. J Exp Med. 2000; 192(7):1075-80. PMCID: PMC2193310.
50. Sullivan T, Miao Z, Dairaghi D J, Krasinski A, Wang Y, Zhao B N, Baumgart T, Ertl L S, Pennell A, Seitz L, Powers J, Zhao R, Ungashe S, Wei Z, Boring L, Tsou C L, Charo I, Berahovich R D, Schall T J, Jaen J C. CCR2 antagonist CCX140-B provides renal and glycemic benefits in diabetic transgenic human CCR2 knockin mice. Am J Physiol Renal Physiol. 2013; 305(9):F1288-97. PMCID: PMC4073927.
51. Kapoor A, Thiemermann C. Targeting CCR2: a novel therapeutic strategy for septic shock? Am J Respir Crit Care Med. 2011; 183(2):150-1.
52. Struthers M, Pasternak A. CCR2 antagonists. Curr Top Med Chem. 2010; 10(13):1278-98.
53. Carter P H. Progress in the discovery of CC chemokine receptor 2 antagonists, 2009-2012. Expert Opin Ther Pat. 2013; 23(5):549-68.
54. Cherney R J, Mo R, Meyer D T, Nelson D J, Lo Y C, Yang G, Scherle P A, Mandlekar S, Wasserman Z R, Jezak H, Solomon K A, Tebben A J, Carter P H, Decicco C P. Discovery of disubstituted cyclohexanes as a new class of CC chemokine receptor 2 antagonists. J Med Chem. 2008; 51(4):721-4.
55. Kredel S, Wolff M, Hobbie S, Bieler M, Gierschik P, Heilker R. High-content analysis of CCR2 antagonists on human primary monocytes. J Biomol Screen. 2011; 16(7): 683-93.
56. Mirzadegan T, Diehl F, Ebi B, Bhakta S, Polsky I, McCarley D, Mulkins M, Weatherhead G S, Lapierre J M, Dankwardt J, Morgans D, Jr., Wilhelm R, Jarnagin K. Identification of the binding site for a novel class of CCR2b chemokine receptor antagonists: binding to a common chemokine receptor motif within the helical bundle. J Biol Chem. 2000; 275(33):25562-71.
57. Hanefeld M, Schell E, Gouni-Berthold I, Melichar M, Vesela I, Johnson D, Miao S, Sullivan T, Jaen J, Schall T, Bekker P, Group tC-BDS. Orally-administered chemokine receptor CCR2 antagonist CCX140-B in type 2 diabetes: a pilot double-blind, randomized clinical trial. J Diabetes Metab. 2012; 3:1-8.
58. Pajares V, Puzo C, Castillo D, Lerma E, Montero M A, Ramos-Barbon D, Amor-Carro O, Gil de Bernabe A, Franquet T, Plaza V, Hetzel J, Sanchis J, Torrego A. Diagnostic yield of transbronchial cryobiopsy in interstitial lung disease: a randomized trial. Respirology. 2014; 19(6):900-6.
59. Richmond I, Booth H, Ward C, Walters E H. Intrasubject variability in airway inflammation in biopsies in mild to moderate stable asthma. Am J Respir Crit Care Med. 1996; 153(3):899-903.
60. Weiss I D, Jacobson O. Molecular imaging of chemokine receptor CXCR4. Theranostics. 2013; 3(1):76-84. PMCID: PMC3563082.
61. Jacobson O, Weiss I D. CXCR4 chemokine receptor overview: biology, pathology and applications in imaging and therapy. Theranostics. 2013; 3(1):1-2. PMCID: PMC3563074.
62. Wester H J, Keller U, Schottelius M, Beer A, Philipp-Abbrederis K, Hoffmann F, Simecek J, Gerngross C, Lassmann M, Herrmann K, Pellegata N, Rudelius M, Kessler H, Schwaiger M. Disclosing the CXCR4 expression in lymphoproliferative diseases by targeted molecular imaging. Theranostics. 2015; 5(6):618-30. PMCID: PMC4377730.
63. Philipp-Abbrederis K, Herrmann K, Knop S, Schottelius M, Eiber M, Luckerath K, Pietschmann E, Habringer S, Gerngross C, Franke K, Rudelius M, Schirbel A, Lapa C, Schwamborn K, Steidle S, Hartmann E, Rosenwald A, Kropf S, Beer A J, Peschel C, Einsele H, Buck A K, Schwaiger M, Gotze K, Wester H J, Keller U. In vivo molecular imaging of chemokine receptor CXCR4 expression in patients with advanced multiple myeloma. EMBO Mol Med. 2015; 7(4):477-87. PMCID: PMC4403048.
64. Schwarz S W, Oyama R. The role of exploratory investigational new drugs for translating radiopharmaceuticals into first-in-human studies. J Nucl Med. 2015; 56(4):497-500.
65. Schwarz S, Norenberg J, Berridge M, Dragotakes S, Hung J, Link J, Mason N S, Mattmuller S, Nickel R A, Packard A, Paolino J, Petry N, Ponto J, Quinton T M, Seifert K L, Swanson D, Weiner R E, Zigler S. The future of USP monographs for PET drugs. J Nucl Med. 2013; 54(3):472-5.
66. Norenberg J P, Schwarz S, VanBrocklin H. FDA cGMP requirements for PET drugs. J Nucl Med. 2011; 52(5): 16N.
67. Schwarz S W, Dick D, VanBrocklin H F, Hoffman J M. Regulatory Requirements for PET Drug Production. J Nucl Med. 2014; 55(7):1132-7.
68. Decristoforo C, Schwarz S W. Radiopharmacy: regulations and legislations in relation to human applications. Drug Discov Today Technol. 2011; 8(2-4):e71-7.
69. Liu Y, Abendschein D, Woodard G E, Rossin R, McCommis K, Zheng J, Welch M J, Woodard P K. Molecular imaging of atherosclerotic plaque with (64)Cu-labeled natriuretic peptide and PET. J Nucl Med. 2010; 51(1):85-91. PMCID: PMC4410353.
70. Anderson C J, Dehdashti F, Cutler P D, Schwarz S W, Laforest R, Bass L A, Lewis J S, McCarthy D W. 64Cu-TETA-octreotide as a PET imaging agent for patients with neuroendocrine tumors. J Nucl Med. 2001; 42(2):213-21.
71. Dehdashti F, Laforest R, Gao F, Shoghi K I, Aft R L, Nussenbaum B, Kreisel F H, Bartlett N L, Cashen A, Wagner-Johnston N, Mach R H. Assessment of cellular proliferation in tumors by PET using 18F-ISO-1. J Nucl Med. 2013; 54(3):350-7. PMCID: PMC3694753.

72. Herrero P, Laforest R, Shoghi K, Zhou D, Ewald G, Pfeifer J, Duncavage E, Krupp K, Mach R, Gropler R. Feasibility and dosimetry studies for 18F-NOS as a potential PET radiopharmaceutical for inducible nitric oxide synthase in humans. J Nucl Med. 2012; 53(6):994-1001.
73. Dehdashti F, Laforest R, Gao F, Aft R L, Dence C S, Zhou D, Shoghi K I, Siegel B A, Katzenellenbogen J A, Welch M J. Assessment of progesterone receptors in breast carcinoma by PET with 21-18F-fluoro-16alpha, 17alpha-[(R)-(1'-alpha-furylmethylidene)dioxy]-19-norpregn-4-ene-3,20-dione. J Nucl Med. 2012; 53(3):363-70. PMCID: PMC3595048.
74. Laforest R, Dehdashti F, Lewis J S, Schwarz S W. Dosimetry of 60/61/62/64Cu-ATSM: a hypoxia imaging agent for PET. Eur J Nucl Med Mol Imaging. 2005; 32(7):764-70.
75. Lewis J S, Laforest R, Lewis M R, Anderson C J. Comparative dosimetry of copper-64 and yttrium-90-labeled somatostatin analogs in a tumor-bearing rat model. Cancer Biother Radiopharm. 2000; 15(6):593-604.
76. Huang H J, Isakow W, Byers D E, Engle J T, Griffin E A, Kemp D, Brody S L, Gropler R J, Miller J P, Chu W, Zhou D, Pierce R A, Castro M, Mach R H, Chen D L. Imaging pulmonary inducible nitric oxide synthase expression with PET. J Nucl Med. 2015; 56(1):76-81.
77. Chen D L, Bedient T J, Kozlowski J, Rosenbluth D B, Isakow W, Ferkol T W, Thomas B, Mintun M A, Schuster D P, Walter M J. [18F]fluorodeoxyglucose positron emission tomography for lung antiinflammatory response evaluation. Am J Respir Crit Care Med. 2009; 180(6): 533-9. PMCID: PMC2742744.
78. Chen D L, Rosenbluth D B, Mintun M A, Schuster D P. FDG-PET imaging of pulmonary inflammation in healthy volunteers after airway instillation of endotoxin. J Appl Physiol (1985). 2006; 100(5):1602-9.
79. Anderson C J, Ferdani R. Copper-64 radiopharmaceuticals for PET imaging of cancer: advances in preclinical and clinical research. Cancer Biother Radiopharm. 2009; 24(4):379-93. PMCID: PMC2794299.
80. Kledal T N, Rosenkilde M M, Coulin F, Simmons G, Johnsen A H, Alouani S, Power C A, Luttichau H R, Gerstoft J, Clapham P R, Clark-Lewis I, Wells T N, Schwartz T W. A broad-spectrum chemokine antagonist encoded by Kaposi's sarcoma-associated herpesvirus. Science. 1997; 277(5332):1656-9.
81. Luttichau H R, Stine J, Boesen T P, Johnsen A H, Chantry D, Gerstoft J, Schwartz T W. A highly selective C C chemokine receptor (CCR)8 antagonist encoded by the poxvirus molluscum contagiosum. J Exp Med. 2000; 191(1):171-80. PMCID: PMC2195798.
82. Liu Y, Pierce R, Luehmann H P, Sharp T L, Welch M J. PET imaging of chemokine receptors in vascular injury-accelerated atherosclerosis. J Nucl Med. 2013; 54(7): 1135-41. PMCID: PMC4251467.
83. Matute-Bello G, Frevert C W, Martin T R. Animal models of acute lung injury. Am J Physiol Lung Cell Mol Physiol. 2008; 295(3):L379-99. PMCID: PMC2536793.
84. Gamble L, Bagby G J, Quinton L J, Happel K I, Mizgerd J P, Zhang P, Nelson S. The systemic and pulmonary LPS binding protein response to intratracheal lipopolysaccharide. Shock. 2009; 31(2):212-7.
85. Maus U A, Wellmann S, Hampl C, Kuziel W A, Srivastava M, Mack M, Everhart M B, Blackwell T S, Christman J W, Schlondorff D, Bohle R M, Seeger W, Lohmeyer J. CCR2-positive monocytes recruited to inflamed lungs downregulate local CCL2 chemokine levels. Am J Physiol Lung Cell Mol Physiol. 2005; 288(2): L350-8.
86. Gavrilin M A, Gulina I V, Kawano T, Dragan S, Chakravarti L, Kolattukudy P E. Site-directed mutagenesis of CCR2 identified amino acid residues in transmembrane helices 1, 2, and 7 important for MCP-1 binding and biological functions. Biochem Biophys Res Commun. 2005; 327(2):533-40.
87. Byers D E, Alexander-Brett J, Patel A C, Agapov E, Dang-Vu G, Jin X, Wu K, You Y, Alevy Y, Girard J P, Stappenbeck T S, Patterson G A, Pierce R A, Brody S L, Holtzman M J. Long-term IL-33-producing epithelial progenitor cells in chronic obstructive lung disease. J Clin Invest. 2013; 123(9):3967-82. PMCID: PMC3754239.
88. Kim E Y, Battaile J T, Patel A C, You Y, Agapov E, Grayson M H, Benoit L A, Byers D E, Alevy Y, Tucker J, Swanson S, Tidwell R, Tyner J W, Morton J D, Castro M, Polineni D, Patterson G A, Schwendener R A, Allard J D, Peltz G, Holtzman M J. Persistent activation of an innate immune response translates respiratory viral infection into chronic lung disease. Nat Med. 2008; 14(6):633-40. PMCID: PMC2575848.
89. Walter M J, Kajiwara N, Karanja P, Castro M, Holtzman M J. Interleukin 12 p40 production by barrier epithelial cells during airway inflammation. J Exp Med. 2001; 193(3):339-51. PMCID: PMC2195918.
90. Boyko E J. Ruling out or ruling in disease with the most sensitive or specific diagnostic test: shortcut or wrong turn? Med Decis Making. 1994; 14(2):175-9.
91. Saederup N, Cardona A E, Croft K, Mizutani M, Cotleur A C, Tsou C L, Ransohoff R M, Charo I F. Selective chemokine receptor usage by central nervous system myeloid cells in CCR2-red fluorescent protein knock-in mice. PLoS One. 2010; 5(10):e13693. PMCID: PMC2965160.
92. Volpe S, Cameroni E, Moepps B, Thelen S, Apuzzo T, Thelen M. CCR2 acts as scavenger for CCL2 during monocyte chemotaxis. PLoS One. 2012; 7(5):e37208. PMCID: PMC3355119.
93. Su Y, Shoghi K I. Single-input-dual-output modeling of image-based input function estimation. Mol Imaging Biol. 2010; 12(3):286-94. PMCID: PMC4286178.
94. Su Y, Shoghi K I. Wavelet denoising in voxel-based parametric estimation of small animal PET images: a systematic evaluation of spatial constraints and noise reduction algorithms. Phys Med Biol. 2008; 53(21):5899-915. PMCID: PMC4283464.
95. Wang B, Zinselmeyer B H, Runnels H A, LaBranche T P, Morton P A, Kreisel D, Mack M, Nickerson-Nutter C, Allen P M, Miller M J. In vivo imaging implicates CCR2(+) monocytes as regulators of neutrophil recruitment during arthritis. Cell Immunol. 2012; 278(1-2):103-12. PMCID: PMC3760198.
96. Herold S, Tabar T S, Janssen H, Hoegner K, Cabanski M, Lewe-Schlosser P, Albrecht J, Driever F, Vadasz I, Seeger W, Steinmueller M, Lohmeyer J. Exudate macrophages attenuate lung injury by the release of IL-1 receptor antagonist in gram-negative pneumonia. Am J Respir Crit Care Med. 2011; 183(10):1380-90.
97. Look D C, Walter M J, Williamson M R, Pang L, You Y, Sreshta J N, Johnson J E, Zander D S, Brody S L. Effects of paramyxoviral infection on airway epithelial cell Foxj1 expression, ciliogenesis, and mucociliary function. Am J Pathol. 2001; 159(6):2055-69. PMCID: PMC1850590.

98. Tyner J W, Kim E Y, Ide K, Pelletier M R, Roswit W T, Morton J D, Battaile J T, Patel A C, Patterson G A, Castro M, Spoor M S, You Y, Brody S L, Holtzman M J. Blocking airway mucous cell metaplasia by inhibiting EGFR antiapoptosis and IL-13 transdifferentiation signals. J Clin Invest. 2006; 116(2):309-21. PMCID: PMC1359039.

99. Carmo A A, Costa B R, Vago J P, de Oliveira L C, Tavares L P, Nogueira C R, Ribeiro A L, Garcia C C, Barbosa A S, Brasil B S, Dusse L M, Barcelos L S, Bonjardim C A, Teixeira M M, Sousa L P. Plasmin induces in vivo monocyte recruitment through protease-activated receptor-1-, MEK/ERK-, and CCR2-mediated signaling. J Immunol. 2014; 193(7):3654-63.

100. Awad A S, Kinsey G R, Khutsishvili K, Gao T, Bolton W K, Okusa M D. Monocyte/macrophage chemokine receptor CCR2 mediates diabetic renal injury. Am J Physiol Renal Physiol. 2011; 301(6):F1358-66. PMCID: PMC3233863.

101. Burnett S H, Kershen E J, Zhang J, Zeng L, Straley S C, Kaplan A M, Cohen D A. Conditional macrophage ablation in transgenic mice expressing a Fas-based suicide gene. J Leukoc Biol. 2004; 75(4):612-23.

102. Liu Y, Ibricevic A, Cohen J A, Cohen J L, Gunsten S P, Frechet J M, Walter M J, Welch M J, Brody S L. Impact of hydrogel nanoparticle size and functionalization on in vivo behavior for lung imaging and therapeutics. Mol Pharm. 2009; 6(6):1891-902. PMCID: PMC2804872.

103. Van Rooijen N, Sanders A. Liposome mediated depletion of macrophages: mechanism of action, preparation of liposomes and applications. J Immunol Methods. 1994; 174(1-2):83-93.

104. Landsman L, Jung S. Lung macrophages serve as obligatory intermediate between blood monocytes and alveolar macrophages. J Immunol. 2007; 179(6):3488-94.

105. Rogers B E, Bigott H M, McCarthy D W, Della Manna D, Kim J, Sharp T L, Welch M J. MicroPET imaging of a gastrin-releasing peptide receptor-positive tumor in a mouse model of human prostate cancer using a 64Cu-labeled bombesin analogue. Bioconjug Chem. 2003; 14(4):756-63.

106. Combadiere C, Ahuja S K, Van Damme J, Tiffany H L, Gao J L, Murphy P M. Monocyte chemoattractant protein-3 is a functional ligand for CC chemokine receptors 1 and 2B. J Biol Chem. 1995; 270(50):29671-5.

107. Alanis D M, Chang D R, Akiyama H, Krasnow M A, Chen J. Two nested developmental waves demarcate a compartment boundary in the mouse lung. Nat Commun. 2014; 5:3923.

108. Sousa A R, Lane S J, Nakhosteen J A, Yoshimura T, Lee T H, Poston R N. Increased expression of the monocyte chemoattractant protein-1 in bronchial tissue from asthmatic subjects. Am J Respir Cell Mol Biol. 1994; 10(2):142-7.

109. Alam R, York J, Boyars M, Stafford S, Grant J A, Lee J, Forsythe P, Sim T, Ida N. Increased MCP-1, RANTES, and MIP-1alpha in bronchioalveolar lavage fluid of allergic asthmatic patients. Am J Respir Crit Care Med. 1996; 153(4 Pt 1):1398-404.

110. Nava R G, Li W, Gelman A E, Krupnick A S, Miller M J, Kreisel D. Two-photon microscopy in pulmonary research. Semin Immunopathol. 2010; 32(3):297-304. PMCID: PMC4411633.

111. Jalbert E, Shikuma C M, Ndhlovu L C, Barbour J D. Sequential staining improves detection of CCR2 and CX3CR1 on monocytes when simultaneously evaluating CCR5 by multicolor flow cytometry. Cytometry A. 2013; 83(3):280-6.

112. Penton-Rol G, Cota M, Polentarutti N, Luini W, Bernasconi S, Borsatti A, Sica A, LaRosa G J, Sozzani S, Poli G, Mantovani A. Up-regulation of CCR2 chemokine receptor expression and increased susceptibility to the multitropic HIV strain 89.6 in monocytes exposed to glucocorticoid hormones. J Immunol. 1999; 163(6):3524-9.

113. Kruger K, Dischereit G, Seimetz M, Wilhelm J, Weissmann N, Mooren F C. Time course of cigarette smoke-induced changes of systemic inflammation and muscle structure. Am J Physiol Lung Cell Mol Physiol. 2015: ajplung 00074 2015.

114. Shiels M S, Katki H A, Freedman N D, Purdue M P, Wentzensen N, Trabert B, Kitahara C M, Furr M, Li Y, Kemp T J, Goedert J J, Chang C M, Engels E A, Caporaso N E, Pinto L A, Hildesheim A, Chaturvedi A K. Cigarette smoking and variations in systemic immune and inflammation markers. J Natl Cancer Inst. 2014; 106(11). PMCID: PMC4200029.

115. Valenca S S, Lima E A, Dire G F, Bernardo-Filho M, Porto L C. Sodium pertechnetate (Na99mTcO4) biodistribution in mice exposed to cigarette smoke. BMC Nucl Med. 2005; 5(1):1. PMCID: PMC1090589.

116. Hayashida K, Nishimura T, Imakita S, Uehara T. Favorable biodistribution of 99mTc-ECD for brain SPECT comparing with 123I-IMP using alternative body scan. Ann Nucl Med. 1992; 6(4):229-33.

117. Arispe N, Diaz J C, Flora M. Efficiency of histidine-associating compounds for blocking the alzheimer's Abeta channel activity and cytotoxicity. Biophys J. 2008; 95(10):4879-89. PMCID: PMC2576403.

118. Thomas S R, Stabin M G, Chen C T, Samaratunga R C. MIRD Pamphlet No. 14 revised: A dynamic urinary bladder model for radiation dose calculations. Task Group of the MIRD Committee, Society of Nuclear Medicine. J Nucl Med. 1999; 40(4):102S-23S.

119. Schmall A, AI-Tamari H M, Herold S, Kampschulte M, Weigert A, Wietelmann A, Vipotnik N, Grimminger F, Seeger W, Pullamsetti S S, Savai R. Macrophage and cancer cell cross-talk via CCR2 and CX3CR1 is a fundamental mechanism driving lung cancer. Am J Respir Crit Care Med. 2015; 191(4):437-47.

The invention claimed is:

1. A method of detecting CCR2 receptors in a subject having lung disease, the method comprising:
   administering a CCR2-specific imaging agent to the subject; and
   detecting a first signal from the CCR2-specific imaging agent at a first timepoint,
   wherein
      the CCR2-specific imaging agent comprises a CCR2 binding peptide comprising a TFLK sequence, a radiolabel, and a chelator;
      the CCR2 binding peptide is no more than 200 amino acids in length;
      the CCR2-specific imaging agent specifically binds CCR2$^+$ cells;
      the chelator is conjugated to the CCR2 binding peptide; and
      the radiolabel is bound to the chelator.

2. The method of claim 1, wherein the CCR2$^+$ cells are CCR2$^+$ monocytes and macrophages.

3. The method of claim 1, wherein the first signal detected from the CCR2-specific imaging agent is greater in a tissue comprising CCR2 receptors compared to a tissue not comprising CCR2 receptors.

4. The method of claim 1, the method further comprising:
   administering the CCR2-specific imaging agent to the subject at a second timepoint and detecting a second signal, wherein
   the second signal is greater than the first signal indicates the lung disease has progressed;
   the second signal is equal to the first signal indicates the lung disease has not progressed; or
   the second signal is less than the first signal indicates the lung disease has not progressed.

5. The method of claim 1, wherein all or a portion of the amino acids of the CCR2 binding peptide are in L configuration or in D configuration.

6. The method of claim 1, wherein the CCR2 binding peptide is no more than 50 amino acids in length.

7. The method of claim 1, wherein the CCR2 binding peptide is no more than 18 amino acids in length.

8. The method of claim 1, wherein the CCR2 binding peptide comprises an amino acid sequence, X1-TFLKC-X2 (SEQ ID NO: 2), wherein X1 is absent, is glycine, or represents an amino acid sequence selected from the group consisting of AG, LG, YLG, and HYLG; and X2 independently is absent, methionine, or represents an amino acid sequence selected from the group consisting of MA, MAN, MANG, MANGF, MANGFV, MANGFVW, MANGFVWE, and MANGFVWEN.

9. The method of claim 1, wherein the CCR2 binding peptide comprises an amino acid sequence, X1-TFLK-X3 (SEQ ID NO: 18), wherein X1 is absent, is glycine, or represents an amino acid sequence selected from the group consisting of AG, LG, YLG, and HYLG; and X3 independently is absent or is alanine.

10. The method of claim 1, wherein the CCR2 binding peptide is selected from the group consisting of:

| | |
|---|---|
| LGTFLKC; | (SEQ ID NO: 3) |
| HYLGTFLKCMA; | (SEQ ID NO: 4) |
| LGTFLKCMA; | (SEQ ID NO: 5) |
| HYLGTFLKC; | (SEQ ID NO: 6) |
| GTFLKCMANGF; | (SEQ ID NO: 7) |
| TFLKCMANGFV; | (SEQ ID NO: 8) |
| HYLGTFLKCMANGFVWEN; | (SEQ ID NO: 9) |
| LGTFLK; | (SEQ ID NO: 19) |
| AGTFLKC; | (SEQ ID NO: 20) |
| LGTFLKA; | (SEQ ID NO: 21) |
| GTFLK; and | (SEQ ID NO: 22) |
| AGTFLKA. | (SEQ ID NO: 23) |

11. The method of claim 1, wherein the CCR2 binding peptide comprises LGTFLKC (SEQ ID NO: 3).

12. The method of claim 1, wherein the CCR2 binding peptide comprises an amino acid sequence, Thr-Phe-Leu-Lys (SEQ ID NO: 17).

13. The method of claim 1, wherein the CCR2 binding peptide comprises an amino acid sequence, Thr-Phe-Leu-Lys-Cys (SEQ ID NO: 1).

14. The method of claim 1, wherein the CCR2 binding peptide comprises a linear ECL1i peptide or a cyclized ECL1i peptide.

15. The method of claim 1, wherein the radiolabel is selected from the group consisting of $^2$H (D or deuterium), $^3$H (T or tritium), $^{11}$C, $^{13}$C, $^{14}$C, $^{64}$Cu, $^{67}$Cu, $^{177}$Lu, $^{13}$N, $^{15}$N, $^{15}$O, $^{17}$O, $^{18}$O, $^{18}$F, $^{89}$Sr, $^{35}$S, $^{153}$Sm, $^{36}$Cl, $^{82}$Br, $^{75}$Br, $^{76}$Br, $^{77}$Br, $^{123}$I, $^{124}$I, $^{125}$I, $^{131}$I, $^{111}$In, $^{67}$Ga, $^{68}$Ga, $^{177}$Lu, $^{186}$Re, $^{188}$Re, $^{201}$Tl, $^{99m}$Tc, $^{90}$Y, $^{89}$Zr, and combinations thereof.

16. The method of claim 1, wherein the radiolabel is $^{64}$Cu.

17. The method of claim 1, wherein the radiolabel is selected from the group consisting of oxygen-15 water, nitrogen-13 ammonia, [$^{82}$Rb] rubidium-82 chloride, [$^{11}$C], [$^{11}$C] 25B-NBOMe, [$^{18}$F] Altanserin, [$^{11}$C] Carfentanil, [$^{11}$C] DASB, [$^{11}$C] DTBZ, [$^{18}$F]Fluoropropyl-DTBZ, [$^{11}$C] ((S)-1-(3-hydroxy-4-([11C]methylamino)butyl)-3-phenyl-1,3-dihydrobenzo[c][1,2,5]thiadiazole,2,2-dioxide ([$^{11}$C] ME@HAPTHI), [$^{18}$F] Fallypride, [$^{18}$F] Florbetaben, [$^{18}$F] Flubatine, [$^{18}$F] Fluspidine, [$^{18}$F] Florbetapir, [$^{11}$C] Flumazenil, [$^{18}$F] Flutemetamol, [$^{18}$F] Fluorodopa, [$^{18}$F] Desmethoxyfallypride, [$^{18}$F] Mefway, [$^{18}$F] MPPF, [$^{18}$F] Nifene, Pittsburgh compound B, [$^{11}$C] Raclopride, [$^{18}$F] Setoperone, [$^{18}$F] or [$^{11}$C] N-Methylspiperone, [$^{11}$C] Verapamil, [$^{11}$C] Martinostat, Fludeoxyglucose ($^{18}$F)(FDG)-glucose, [$^{11}$C] Acetate, [$^{11}$C] Methionine, [$^{11}$C] Choline, [$^{18}$F] Fluciclovine, [$^{18}$F] Fluorocholine, [$^{18}$F] FET, [$^{18}$F] FMISO, [$^{18}$F] 3'-fluoro-3'-deoxythymidine, [$^{68}$Ga] DOTA, [$^{68}$Ga] PSMA, [$^{18}$F] Fluorodeoxysorbitol (FDS), and combinations thereof.

18. The method of claim 1, wherein the chelator is selected from the group consisting of NHS-MAG3, MAG3, DTPA, 3p-C-NE3TA, NOTA, 3p-C-NOTA, 3p-C-DE4TA, ATSM, a tetraazamacrocyclic ligand, DOTA (1,4,7,10-tetraazacyclododecane-1,4,7,10-tetraacetic acid), DOTA-NHS, pSCN-Bn-DOTA, pNH2-Bn-DOTA, TETA (1,4,8,11-tetraazacyclotetradecane-1,4,8,11-tetraacetic acid, TETA-octreotide (OC), hexaazamacrobicyclic cage-type ligands, Sarcophogine chelators, cross-bridged tetraamine ligands, CB-TE2A (4,11-bis(carboxymethyl)-1,4,8,11-tetraazabicyclo[6.6.2]hexadecane), 6-Hydrazinopridine-3-carboxylic acid (Hynic), NHS-Hynic, 2,2',2"-(10-(2-((2-(2,5-dioxo-2,5-dihydro-1 H-pyrrol-1-yl)ethyl)amino)-2-oxoethyl)-1,4,7,10-tetraazacyclododecane-1,4,7-triyl)triacetic acid (Maleimido-mono-amide-DOTA), and combinations thereof.

19. The method of claim 1, wherein the chelator comprises a tetraazamacrocyclic ligand; NOTA; DOTA; TETA; or 2,2',2"-(10-(2-((2-(2,5-dioxo-2,5-dihydro-1H-pyrrol-1-yl)ethyl)amino)-2-oxoethyl)-1,4,7,10-tetraazacyclododecane-1,4,7-triyl)triacetic acid (Maleimido-mono-am ide-DOTA).

20. The method of claim 1, wherein the radiolabel is $^{64}$Cu, the CCR2 binding peptide is ECL1i, and the chelator is DOTA.

21. The method of claim 1, wherein the CCR2-specific imaging agent further comprises a linker, the linker selected from the group consisting of a chemical or physical bond, PEG, TA-PEG-Maleimide, TA-PEG-OMe, TA-PEG, an isothiocyanate group, a carboxylic acid or carboxylate groups, a dendrimer, a dendron, Fmoc-protected-2,3-diaminopropanoic acid, ascorbic acid, a silane linker, minopropyltrimethoxysilane (APTMS), dopamine, 2 thiol groups, 2 primary amines, a carboxylic acid and primary amine, maleimide and thiol, hydrazide and aldehyde, or a primary amine and aldehyde, an amide, a thioether, a disulfide, an acetyl-hydrazone group, a polycyclic group, a click chemistry (CC) group, and combinations thereof.

22. The method of claim 1, wherein detecting the CCR2-specific imaging agent is detected via positron emission tomography (PET) imaging, single photon emission computed tomography (SPECT) imaging, mass spectrometry, gamma imaging, magnetic resonance imaging (MRI), magnetic resonance spectroscopy, fluorescence spectroscopy, CT, ultrasound, or X-ray.

23. The method of claim 22, wherein detecting the CCR2-specific imaging agent is detected via positron emission tomography (PET) imaging or single photon emission computed tomography (SPECT) imaging.

24. The method of claim 1, wherein CCR2 signal detection is indicative of atherosclerotic plaques or CCR2+ monocytes and macrophages in atherosclerotic plaques.

* * * * *